US012807968B2

(12) United States Patent
Liu et al.

(10) Patent No.: US 12,807,968 B2
(45) Date of Patent: Nov. 24, 2026

(54) AAV VECTORS AND METHODS AND USES THEREOF

(71) Applicant: REGENXBIO Inc., Rockville, MD (US)

(72) Inventors: Ye Liu, Clarksville, MD (US); Andrew Mercer, Poolesville, MD (US); Chunping Qiao, Rockville, MD (US); April R. Tepe, Laurel, MD (US); Nicolas Buss, Rockville, MD (US)

(73) Assignee: REGENXBIO Inc., Rockville, MD (US)

( * ) Notice: Subject to any disclaimer, the term of this patent is extended or adjusted under 35 U.S.C. 154(b) by 414 days.

(21) Appl. No.: 18/558,495

(22) PCT Filed: May 3, 2022

(86) PCT No.: PCT/US2022/027390

§ 371 (c)(1),
(2) Date: Nov. 1, 2023

(87) PCT Pub. No.: WO2022/235614

PCT Pub. Date: Nov. 10, 2022

(65) Prior Publication Data

US 2024/0218397 A1 Jul. 4, 2024

Related U.S. Application Data

(60) Provisional application No. 63/183,999, filed on May 4, 2021.

(51) Int. Cl.
*C12N 15/86* (2006.01)

(52) U.S. Cl.
CPC .... *C12N 15/86* (2013.01); *C12N 2750/14143* (2013.01); *C12N 2830/38* (2013.01)

(58) Field of Classification Search
CPC .......... C12N 15/86; C12N 2750/14143; C12N 2830/38
See application file for complete search history.

(56) References Cited

U.S. PATENT DOCUMENTS

2016/0108373 A1* 4/2016 Bennett .................. C12N 15/86
435/235.1

FOREIGN PATENT DOCUMENTS

| | | | |
|---|---|---|---|
| EP | 2870237 | | 5/2015 |
| WO | 2014007858 | A1 | 1/2014 |
| WO | 2016210170 | A1 | 12/2016 |
| WO | 2022011262 | A1 | 1/2022 |

OTHER PUBLICATIONS

International Search Report for PCT/US2022/027390 dated Nov. 4, 2022, 8 pages.
Written Opinion of the ISA for PCT/US2022/027390 dated Nov. 4, 2022, 9 pages.

* cited by examiner

*Primary Examiner* — Fereydoun G Sajjadi
*Assistant Examiner* — Alexander W Nicol
(74) *Attorney, Agent, or Firm* — Nixon & Vanderhye, PC

(57) ABSTRACT

The present invention relates to nucleic acid expression cassettes that are engineered to include polynucleotide sequences useful as inert stuffer (or filler) sequences in expression cassettes, particularly useful for transgene expression delivered as viral vectors, incorporating the engineered expression cassettes described herein, including rAAVs, for use in therapy.

7 Claims, 4 Drawing Sheets

Specification includes a Sequence Listing.

SEQUENCE LISTING

```
<160> NUMBER OF SEQ ID NOS: 44

<210> SEQ ID NO 1
<211> LENGTH: 1602
<212> TYPE: DNA
<213> ORGANISM: Artificial Sequence
<220> FEATURE:
<223> OTHER INFORMATION: recombinant polynucleotide

<400> SEQUENCE: 1

atagtctatc caggttgagc atcctgctgg tggttacaag aaactgtttg aaactgtgga     60

ggaactgtcc tcgccgctca cagctcatgt aacaggcagg atccccctct ggctcaccgg    120

cagtctcctt cgatgtgggc caggactctt tgaagttgga tctgagccat tttaccacct    180

gtttgatggg caagccctcc tgcacaagtt tgactttaaa gaaggacatg tcacatacca    240

cagaaggttc atccgcactg atgcttacgt acgggcaatg actgagaaaa ggatcgtcat    300

aacagaattt ggcacctgtg ctttcccaga tccctgcaag aatatatttt ccaggttttt    360

ttcttacttt cgaggagtag aggttactga caattgccct tgttaatgtc tacccagtgg    420

gggaagatta ctacgcttgc acagagacca actttattac aaagattaat ccagagacct    480

tggagacaat taagcaggtt gatctttgca actaagtctc tgtcaatggg gccactgctc    540

acccccacat tgaaaatgat ggaaccgttt acaatattgg taattgcttt ggaaaaaatt    600

tttcaattgc ctacaacatt gtaaagatcc caccactgca agcagacaag gaagatccaa    660

taagcaagtc agagatcgtt gtacaattcc cctgcagtga ccgattcaag ccatcttacg    720

ttcatagttt tggtctgact cccaactata tcgtttttgt ggagacacca gtcaaaatta    780

acctgttcaa gttcctttct tcatggagtc tttggggagc caactacatg gattgttttg    840

agtccaatga aaccatgggg tttggcttca tattgctgac aaaaaaagga aaaagtacct    900

caataataaa tacagaactt ctcctttcaa cctcttccat cacatcaaca cctatgaaga    960

caatgggttt ctgattgtgg atctctgctg ctggaaagga tttgagtttg tttataatta   1020
```

```
cttatattta gccaatttac gtgagaactg ggaagaggtg aaaaaaaatg ccagaaaggc   1080

tccccaacct gaagttagga gatatgtact tcctttgaat attgacaagg ctgacacagg   1140

caagaattta gtcagctccc caatacaact gccactgcaa ttctgtgcag tgacgagact   1200

atctggctgg agcctgaagt tctcttttca gggcctcgtc aagcatttga gtttcctcaa   1260

atcaattacc agaagtattg tgggaaacct tacacatatg cgtatggact tggcttgaat   1320

cactttgttc cagataggct ctgtaagctg aatgtcaaaa ctaaagaaac ttgggtttgg   1380

caagagcctg attcataccc atcagaaccc atctttgttt ctcacccaga tgccttggaa   1440

gaagatgatg gtgtagttct gagtgtggtg gtgagcccag gagcaggaca aaagcctgct   1500

tatctcctga ttctgaatgc caaggactta agtgaagttg cccgggctga agtggagatt   1560

aacatccctg tcacctttca tggactgttc aaaaaatctt ga                      1602
```

<210> SEQ ID NO 2
<211> LENGTH: 596
<212> TYPE: DNA
<213> ORGANISM: Artificial Sequence
<220> FEATURE:
<223> OTHER INFORMATION: recombinant polynucleotide

<400> SEQUENCE: 2

```
cgagtttaat tggtttatag aactcttcaa acaaattaaa ccaaaaattt caatgccaag     60

aaagggtctt taaaacgaaa ttacagaagg accaaatgat aaggaagaaa aatgcagaga    120

taaaagtaat atcaattagg atcataagct acttattatc aatgaaaagt aacagaaaca    180

tagatgctgc agaaatcttc tgaggagtag cttcaacgcc tcagggtgtg gacaatgtat    240

tcagcataga ggtccctgta atggggatat cagaatccag agttgcttta atgttacaaa    300

ctaaaaaaga tgtaagagag tttggttctt gataaagaaa cagaggctta cattgagtac    360

tggatagctt caaccgcaga ctcagatggc agaaaatcat tcactgcaac ttccttgttc    420

tcgtttttct tgtctgtaag atattagagt taaagggaaa aactaatact tgttgagaga    480

tcaatagaga tgaataagga ggaacactga agaaaaagga tacagtcttc gaagaaacga    540

cggatttcag agagacggtg aggaggaagt tctttgatgt cagtgtagtg cttata        596
```

<210> SEQ ID NO 3
<211> LENGTH: 1096
<212> TYPE: DNA
<213> ORGANISM: Artificial Sequence
<220> FEATURE:
<223> OTHER INFORMATION: recombinant polynucleotide

<400> SEQUENCE: 3

```
cgagtttaat tggtttatag aactcttcaa acaaattaaa ccaaaaattt caatgccaag     60

aaagggtctt taaaacgaaa ttacagaagg accaaatgat aaggaagaaa aatgcagaga    120

taaaagtaat atcaattagg atcataagct acttattatc aatgaaaagt aacagaaaca    180

tagatgctgc agaaatcttc tgaggagtag cttcaacgcc tcagggtgtg gacaatgtat    240

tcagcataga ggtccctgta atggggatat cagaatccag agttgcttta atgttacaaa    300

ctaaaaaaga tgtaagagag tttggttctt gataaagaaa cagaggctta cattgagtac    360

tggatagctt caaccgcaga ctcagatggc agaaaatcat tcactgcaac ttccttgttc    420

tcgtttttct tgtctgtaag atattagagt taaagggaaa aactaatact tgttgagaga    480

tcaatagaga tgaataagga ggaacactga agaaaaagga tacagtcttc gaagaaacga    540

cggatttcag agagacggtg aggaggaagt tctttgatgt cagtgtagtg cttatattca    600
```

```
ggatcatcaa cacacactgc aatgatcttg tcatcttttt caccctaaaa ttacagcgcc    660

aaaaatacaa gattggagta caagaccatt taaactgacc taaaggatta gagtaagaga    720

aaaaaaaaac agagtctttt cattgatcaa gtttaggttt tacctggtca atcataggca    780

ttaatccaat ggctctggca cgcagaaaac aacccggaag cacaggttcc tacacaaaga    840

taataatata tatttgaaat acaaaaaatt ggtgcaaata gtatagggat aatatgagaa    900

agaaagaaag agtaatacct gcatgatgac taagacatca atggggtcat tgtcttcaca    960

caatgtgcga ggaacaaaac catagttgtg agggtacaca actgatgagt agagaatacg   1020

atcaacctga atgagagata tcaaacttgt tgagattgat tttgctataa gaaaaccatt   1080

catataaaaa ataaaa                                                   1096
```

<210> SEQ ID NO 4
<211> LENGTH: 1596
<212> TYPE: DNA
<213> ORGANISM: Artificial Sequence
<220> FEATURE:
<223> OTHER INFORMATION: recombinant polynucleotide

<400> SEQUENCE: 4

```
cgagtttaat tggtttatag aactcttcaa acaaattaaa ccaaaaattt caatgccaag     60

aaagggtctt taaaacgaaa ttacagaagg accaaatgat aaggaagaaa aatgcagaga    120

taaaagtaat atcaattagg atcataagct acttattatc aatgaaaagt aacagaaaca    180

tagatgctgc agaaatcttc tgaggagtag cttcaacgcc tcagggtgtg gacaatgtat    240

tcagcataga ggtccctgta atggggatat cagaatccag agttgcttta atgttacaaa    300

ctaaaaaaga tgtaagagag tttggttctt gataaagaaa cagaggctta cattgagtac    360

tggatagctt caaccgcaga ctcagatggc agaaaatcat tcactgcaac ttccttgttc    420

tcgtttttct tgtctgtaag atattagagt taaagggaaa aactaatact tgttgagaga    480

tcaatagaga tgaataagga ggaacactga agaaaaagga tacagtcttc gaagaaacga    540

cggatttcag agagacggtg aggaggaagt tctttgatgt cagtgtagtg cttatattca    600

ggatcatcaa cacacactgc aatgatcttg tcatcttttt caccctaaaa ttacagcgcc    660

aaaaatacaa gattggagta caagaccatt taaactgacc taaaggatta gagtaagaga    720

aaaaaaaaac agagtctttt cattgatcaa gtttaggttt tacctggtca atcataggca    780

ttaatccaat ggctctggca cgcagaaaac aacccggaag cacaggttcc tacacaaaga    840

taataatata tatttgaaat acaaaaaatt ggtgcaaata gtatagggat aatatgagaa    900

agaaagaaag agtaatacct gcatgatgac taagacatca atggggtcat tgtcttcaca    960

caatgtgcga ggaacaaaac catagttgtg agggtacaca actgatgagt agagaatacg   1020

atcaacctga atgagagata tcaaacttgt tgagattgat tttgctataa gaaaaccatt   1080

catataaaaa ataaactttg ttctcatcta accttgatga gtcctgtctt tttgtcaagc   1140

tcgtatttga ccttgcttcc tttagtgatc tcaacaacct aataatcatc caaagataaa   1200

atgattagag aatctaataa caacatactc tgtttagaac aaagagtagg aaaaaactta   1260

ccacattgaa aatctgtgga gctccaggtc ctagatagat tatccagact tatgatttag   1320

taacagaata caaaagtatg aaatcaaaaa gtagcatgtt tagaatgatt tatataccaa   1380

tctcaagatc atgccatgga tgagcagcta cggatcttct tgacaaggat gagagaatcc   1440

tctcgttaag acgaggagct ggtcgctgca gcctctggtt atctttagtt tcttcactca   1500
```

```
tctgtcaaaa tcagaacgtt tcatcactca ttgatattga ctgaatctaa catcataacc   1560

ctaattggca gagagagaat caatcgaatc aagaga                              1596


<210> SEQ ID NO 5
<211> LENGTH: 2002
<212> TYPE: DNA
<213> ORGANISM: Artificial Sequence
<220> FEATURE:
<223> OTHER INFORMATION: recombinant polynucleotide

<400> SEQUENCE: 5

cgagtttaat tggtttatag aactcttcaa acaaattaaa ccaaaaattt caatgccaag     60

aaagggtctt taaaacgaaa ttacagaagg accaaatgat aaggaagaaa aatgcagaga    120

taaaagtaat atcaattagg atcataagct acttattatc aatgaaaagt aacagaaaca    180

tagatgctgc agaaatcttc tgaggagtag cttcaacgcc tcagggtgtg gacaatgtat    240

tcagcataga ggtccctgta atggggatat cagaatccag agttgcttta atgttacaaa    300

ctaaaaaaga tgtaagagag tttggttctt gataaagaaa cagaggctta cattgagtac    360

tggatagctt caaccgcaga ctcagatggc agaaaatcat tcactgcaac ttccttgttc    420

tcgtttttct tgtctgtaag atattagagt taaagggaaa aactaatact tgttgagaga    480

tcaatagaga tgaataagga ggaacactga agaaaaagga tacagtcttc gaagaaacga    540

cggatttcag agagacggtg aggaggaagt tctttgatgt cagtgtagtg cttatattca    600

ggatcatcaa cacacactgc aatgatcttg tcatcttttt caccctaaaa ttacagcgcc    660

aaaaatacaa gattggagta caagaccatt taaactgacc taaaggatta gagtaagaga    720

aaaaaaaaac agagtctttt cattgatcaa gtttaggttt tacctggtca atcataggca    780

ttaatccaat ggctctggca cgcagaaaac aacccggaag cacaggttcc tacacaaaga    840

taataatata tatttgaaat acaaaaaatt ggtgcaaata gtatagggat aatatgagaa    900

agaaagaaag agtaatacct gcatgatgac taagacatca atggggtcat tgtcttcaca    960

caatgtgcga ggaacaaaac catagttgtg agggtacaca actgatgagt agagaatacg   1020

atcaacctga atgagagata tcaaacttgt tgagattgat tttgctataa gaaaaccatt   1080

catataaaaa ataaactttg ttctcatcta accttgatga gtcctgtctt tttgtcaagc   1140

tcgtatttga ccttgcttcc tttagtgatc tcaacaacct aataatcatc caaagataaa   1200

atgattagag aatctaataa caacatactc tgtttagaac aaagagtagg aaaaaactta   1260

ccacattgaa aatctgtgga gctccaggtc ctagatagat tatccagact tatgatttag   1320

taacagaata caaaagtatg aaatcaaaaa gtagcatgtt tagaatgatt tatataccaa   1380

tctcaagatc atgccatgga tgagcagcta cggatcttct tgacaaggat gagagaatcc   1440

tctcgttaag acgaggagct ggtcgctgca gcctctggtt atctttagtt tcttcactca   1500

tctgtcaaaa tcagaacgtt tcatcactca ttgatattga ctgaatctaa catcataacc   1560

ctaattggca gagagagaat caatcgaatc aagagtatta aatggaaaaa gcgaatcaag   1620

accccacaag ggaaaacaat ccttaaagca gacttgagat cgatcatacc caaattatgg   1680

attcatatat tgttaacgta tcgattactg aaaagatgta taccaaatct gttcactttt   1740

tctctataga ctcgatggat gattgagatt tgaagcaaca aaatacccag aagattaaac   1800

atggaaaagc atcaaacttt gatgatctta gaacgatgac aaaagaaaaa aaaacgtacc   1860

tttggatcga aacgaaacag ccgattgttg ttttctttat cgcaaggatg atgaagaaac   1920

tttgggagag aaacaagtga agcccgttgg tctagcaagt gattgtaaaa tgtatatatg   1980
```

agtcaccacc gagatatacg ga 2002

<210> SEQ ID NO 6
<211> LENGTH: 1676
<212> TYPE: DNA
<213> ORGANISM: Artificial Sequence
<220> FEATURE:
<223> OTHER INFORMATION: recombinant polynucleotide

<400> SEQUENCE: 6
gacattgatt attgactagt tattaatagt aatcaattac ggggtcatta gttcatagcc 60
catatatgga gttccgcgtt acataactta cggtaaatgg cccgcctggc tgaccgccca 120
acgacccccg cccattgacg tcaataatga cgtatgttcc catagtaacg ccaataggga 180
ctttccattg acgtcaatgg gtggagtatt tacggtaaac tgcccacttg gcagtacatc 240
aagtgtatca tatgccaagt acgcccccta ttgacgtcaa tgacggtaaa tggcccgcct 300
ggcattatgc ccagtacatg accttatggg actttcctac ttggcagtac atctacgtat 360
tagtcatcgc tattaccatg gtcgaggtga gccccacgtt ctgcttcact ctccccatct 420 ccccccccctc cccaccccca attttgtatt tatttatttt ttaattattt tgtgcagcga 480
tgggggcggg gggggggggg gggcgcgcgc caggcggggc ggggcggggc gaggggcggg 540
gcggggcgag gcggagaggt gcggcggcag ccaatcagag cggcgcgctc cgaaagtttc 600
cttttatggc gaggcggcgg cggcggcggc cctataaaaa gcgaagcgcg cggcgggcgg 660
gagtcgctgc gcgctgcctt cgccccgtgc cccgctccgc cgccgcctcg cgccgcccgc 720
cccggctctg actgaccgcg ttactcccac aggtgagcgg gcgggacggc ccttctcctc 780
cgggctgtaa ttagcgcttg gtttaatgac ggcttgtttc ttttctgtgg ctgcgtgaaa 840
gccttgaggg gctccgggag ggccctttgt gcggggggag cggctcgggg ggtgcgtgcg 900
tgtgtgtgtg cgtggggagc gccgcgtgcg gctccgcgct gcccggcggc tgtgagcgct 960
gcgggcgcgg cgcggggctt tgtgcgctcc gcagtgtgcg cgaggggagc gcggccgggg 1020
gcggtgcccc gcggtgcggg gggggctgcg aggggaacaa aggctgcgtg cggggtgtgt 1080
gcgtgggggg gtgagcaggg ggtgtgggcg cgtcggtcgg gctgcaaccc cccctgcacc 1140
cccctccccg agttgctgag cacggcccgg cttcgggtgc ggggctccgt acggggcgtg 1200
gcgcggggct cgccgtgccg ggcggggggt ggcggcaggt gggggtgccg ggcggggcgg 1260
ggccgcctcg ggccggggag ggctcggggg aggggcgcgg cggcccccgg agcgccggcg 1320
gctgtcgagg cgcggcgagc cgcagccatt gccttttatg gtaatcgtgc gagagggcgc 1380
agggacttcc tttgtcccaa atctgtgcgg agccgaaatc tgggaggcgc cgccgcaccc 1440
cctctagcgg gcgcggggcg aagcggtgcg gcgccggcag gaaggaaatg ggcggggagg 1500
gccttcgtgc gtcgccgcgc cgccgtcccc ttctccctct ccagcctcgg ggctgtccgc 1560
ggggggacgg ctgccttcgg gggggacggg gcagggcggg gttcggcttc tggcgtgtga 1620
ccggcggctc tagagcctct gctaaccatg ttcatgcctt cttctttttc ctacag 1676

<210> SEQ ID NO 7
<211> LENGTH: 433
<212> TYPE: DNA
<213> ORGANISM: Artificial Sequence
<220> FEATURE:
<223> OTHER INFORMATION: recombinant polynucleotide

<400> SEQUENCE: 7

-continued ccctgcatgc gaagatcttc gaacaaggct gtgggggact gagggcaggc tgtaacaggc 60
ttgggggcca gggcttatac gtgcctggga ctcccaaagt attactgttc catgttcccg 120
gcgaagggcc agctgtcccc cgccagctag actcagcact tagtttagga accagtgagc 180
aagtcagccc ttggggcagc ccatacaagg ccatggggct gggcaagctg cacgcctggg 240
tccggggtgg gcacggtgcc cgggcaacga gctgaaagct catctgctct caggggcccc 300
tccctgggga cagcccctcc tggctagtca caccctgtag gctcctctat ataacccagg 360
ggcacagggg ctgccctcat tctaccacca cctccacagc acagacagac actcaggagc 420
cagccagcgt cga 433

<210> SEQ ID NO 8
<211> LENGTH: 328
<212> TYPE: DNA
<213> ORGANISM: Artificial Sequence
<220> FEATURE:
<223> OTHER INFORMATION: recombinant polynucleotide

<400> SEQUENCE: 8
ggccgtccgc cctcggcacc atcctcacga cacccaaata tggcgacggg tgaggaatgg 60
tggggagtta tttttagagc ggtgaggaag gtgggcaggc agcaggtgtt ggcgctctaa 120
aaataactcc cgggagttat ttttagagcg gaggaatggt ggacacccaa atatggcgac 180
ggttcctcac ccgtcgccat atttgggtgt ccgccctcgg ccggggccgc attcctgggg 240
gccgggcggt gctcccgccc gcctcgataa aaggctccgg ggccggcggc ggcccacgag 300
ctacccggag gagcgggagg cgccaagc 328

<210> SEQ ID NO 9
<211> LENGTH: 174
<212> TYPE: DNA
<213> ORGANISM: Artificial Sequence
<220> FEATURE:
<223> OTHER INFORMATION: recombinant polynucleotide

<400> SEQUENCE: 9
gaatggtgga cacccaaata tggcgacggt tcctcacccg tcgccatatt tgggtgtccg 60
ccctcggccg gggccgcatt cctgggggcc gggcggtgct cccgcccgcc tcgataaaag 120
gctccggggc cggcggcggc ccacgagcta cccggaggag cgggaggcgc caag 174

<210> SEQ ID NO 10
<211> LENGTH: 865
<212> TYPE: DNA
<213> ORGANISM: Artificial Sequence
<220> FEATURE:
<223> OTHER INFORMATION: recombinant polynucleotide

<400> SEQUENCE: 10
ccactacggg tttaggctgc ccatgtaagg aggcaaggcc tggggacacc cgagatgcct 60
ggttataatt aacccagaca tgtggctgcc cccccccccc ccaacacctg ctgcctctaa 120
aaataaccct gtccctggtg gatcccacta cgggtttagg ctgcccatgt aaggaggcaa 180
ggcctgggga cacccgagat gcctggttat aattaaccca gacatgtggc tgcccccccc 240
ccccccaaca cctgctgcct ctaaaaataa ccctgtccct ggtggatccc actacgggtt 300
taggctgccc atgtaaggag gcaaggcctg gggacacccg agatgcctgg ttataattaa 360
cccagacatg tggctgcccc cccccccccc aacacctgct gcctctaaaa ataaccctgt 420
ccctggtgga tcccctgcat gcgaagatct tcgaacaagg ctgtggggga ctgagggcag 480
gctgtaacag gcttgggggc cagggcttat acgtgcctgg gactcccaaa gtattactgt 540
tccatgttcc cggcgaaggg ccagctgtcc cccgccagct agactcagca cttagtttag 600
gaaccagtga gcaagtcagc ccttggggca gcccatacaa ggccatgggg ctgggcaagc 660
tgcacgcctg ggtccggggt gggcacggtg cccgggcaac gagctgaaag ctcatctgct 720
ctcaggggcc cctccctggg gacagcccct cctggctagt cacaccctgt aggctcctct 780
atataaccca ggggcacagg ggctgccctc attctaccac cacctccaca gcacagacag 840
acactcagga gccagccagc gtcga 865

<210> SEQ ID NO 11
<211> LENGTH: 251
<212> TYPE: DNA
<213> ORGANISM: Artificial Sequence
<220> FEATURE:
<223> OTHER INFORMATION: recombinant polynucleotide

<400> SEQUENCE: 11
atggaggcgg tactatgtag atgagaattc aggagcaaac tgggaaaagc aactgcttcc 60
aaatatttgt gatttttaca gtgtagtttt ggaaaaactc ttagcctacc aattcttcta 120
agtgttttaa aatgtgggag ccagtacaca tgaagttata gagtgtttta atgaggctta 180
aatatttacc gtaactatga aatgctacgc atatcatgct gttcaggctc cgtggccacg 240
caactcatac t 251

<210> SEQ ID NO 12
<211> LENGTH: 212
<212> TYPE: DNA
<213> ORGANISM: Artificial Sequence
<220> FEATURE:
<223> OTHER INFORMATION: recombinant polynucleotide

<400> SEQUENCE: 12
gggcagagcg cacatcgccc acagtccccg agaagttggg gggaggggtc ggcaattgaa 60
cgggtgccta gagaaggtgg cgcggggtaa actgggaaag tgatgtcgtg tactggctcc 120
gcctttttcc cgagggtggg ggagaaccgt atataagtgc agtagtcgcc gtgaacgttc 180
tttttcgcaa cgggtttgcc gccagaacac ag 212

<210> SEQ ID NO 13
<211> LENGTH: 240
<212> TYPE: DNA
<213> ORGANISM: Artificial Sequence
<220> FEATURE:
<223> OTHER INFORMATION: recombinant polynucleotide

<400> SEQUENCE: 13
ctgcagacat gcttgctgcc tgccctggcg tgccctggcg aggcttgccg tcacaggacc 60
cccgctggct gactcagggg cgcaggctct tgcgggggag ctggcctccc gcccccacgg 120
ccacgggccc tttcctggca ggacagcggg atcttgcagc tgtcagggga ggggatgacg 180
ggggactgat gtcaggaggg gatacaaata gtgccgaaca aggaccggat tagatctacc 240

<210> SEQ ID NO 14
<211> LENGTH: 792
<212> TYPE: DNA
<213> ORGANISM: Artificial Sequence
<220> FEATURE:
<223> OTHER INFORMATION: recombinant polynucleotide

<400> SEQUENCE: 14
aagcttgcat gtctaagcta gacccttcag attaaaaata actgaggtaa gggcctgggt 60
aggggaggtg gtgtgagacg ctcctgtctc tcctctatct gcccatcggc cctttgggga 120
ggaggaatgt gcccaaggac taaaaaaagg ccatggagcc agaggggcga gggcaacaga 180
cctttcatgg gcaaaccttg gggccctgct gtctagcatg ccccactacg ggtctaggct 240
gcccatgtaa ggaggcaagg cctggggaca cccgagatgc ctggttataa ttaacccaga 300
catgtggctg cccccccccc cccaacacct gctgcctcta aaaataaccc tgtccctggt 360
ggatcccctg catgcgaaga tcttcgaaca aggctgtggg ggactgaggg caggctgtaa 420
caggcttggg ggccagggct tatacgtgcc tgggactccc aaagtattac tgttccatgt 480
tcccggcgaa gggccagctg tcccccgcca gctagactca gcacttagtt taggaaccag 540
tgagcaagtc agcccttggg gcagcccata caaggccatg gggctgggca agctgcacgc 600
ctgggtccgg ggtgggcacg gtgcccgggc aacgagctga aagctcatct gctctcaggg 660
gcccctccct ggggacagcc cctcctggct agtcacaccc tgtaggctcc tctatataac 720
ccaggggcac aggggctgcc ctcattctac caccacctcc acagcacaga cagacactca 780
ggagcagcca gc 792

<210> SEQ ID NO 15
<211> LENGTH: 448
<212> TYPE: DNA
<213> ORGANISM: Artificial Sequence
<220> FEATURE:
<223> OTHER INFORMATION: recombinant polynucleotide

<400> SEQUENCE: 15
agtgcaagtg ggttttagga ccaggatgag gcggggtggg ggtgcctacc tgacgaccga 60
ccccgaccca ctggacaagc acccaacccc cattccccaa attgcgcatc ccctatcaga 120
gagggggagg ggaaacagga tgcggcgagg cgcgtgcgca ctgccagctt cagcaccgcg 180
gacagtgcct tcgcccccgc ctggcggcgc gcgccaccgc cgcctcagca ctgaaggcgc 240
gctgacgtca ctcgccggtc ccccgcaaac tccccttccc ggccaccttg gtcgcgtccg 300
cgccgccgcc ggcccagccg gaccgcacca cgcgaggcgc gagatagggg ggcacgggcg 360
cgaccatctg cgctgcggcg ccggcgactc agcgctgcct cagtctgcgg tgggcagcgg 420
aggagtcgtg tcgtgcctga gagcgcag 448

<210> SEQ ID NO 16
<211> LENGTH: 229
<212> TYPE: DNA
<213> ORGANISM: Artificial Sequence
<220> FEATURE:
<223> OTHER INFORMATION: recombinant polynucleotide

<400> SEQUENCE: 16
agctgaatgg ggtccgcctc ttttccctgc ctaaacagac aggaactcct gccaattgag 60
ggcgtcaccg ctaaggctcc gccccagcct gggctccaca accaatgaag ggtaatctcg 120
acaaagagca aggggtgggg cgcgggcgcg caggtgcagc agcacacagg ctggtcggga 180
gggcggggcg cgacgtctgc cgtgcggggt cccggcatcg gttgcgcgc 229

<210> SEQ ID NO 17
<211> LENGTH: 1675
<212> TYPE: DNA
<213> ORGANISM: Artificial Sequence
<220> FEATURE:
<223> OTHER INFORMATION: recombinant polynucleotide

<400> SEQUENCE: 17
gtctgcaagc agacctggca gcattgggct ggccgccccc cagggcctcc tcttcatgcc 60
cagtgaatga ctcaccttgg cacagacaca atgttcgggg tgggcacagt gcctgcttcc 120
cgccgcaccc cagcccccct caaatgcctt ccgagaagcc cattgagtag ggggcttgca 180
ttgcacccca gcctgacagc ctggcatctt gggataaaag cagcacagcc ccctaggggc 240
tgcccttgct gtgtggcgcc accggcggtg gagaacaagg ctctattcag cctgtgccca 300
ggaaagggga tcaggggatg cccaggcatg gacagtgggt ggcagggggg gagaggaggg 360
ctgtctgctt cccagaagtc caaggacaca aatgggtgag gggactgggc agggttctga 420
ccctgtggga ccagagtgga gggcgtagat ggacctgaag tctccaggga caacagggcc 480
caggtctcag gctcctagtt gggcccagtg gctccagcgt ttccaaaccc atccatcccc 540
agaggttctt cccatctctc caggctgatg tgtgggaact cgaggaaata aatctccagt 600
gggagacgga ggggtggcca gggaaacggg gcgctgcagg aataaagacg agccagcaca 660
gccagctcat gcgtaacggc tttgtggagc tgtcaaggcc tggtctctgg gagagaggca 720
cagggaggcc agacaaggaa ggggtgacct ggagggacag atccaggggc taaagtcctg 780
ataaggcaag agagtgccgg ccccctcttg ccctatcagg acctccactg ccacatagag 840
gccatgattg acccttagac aaagggctgg tgtccaatcc cagcccccag ccccagaact 900
ccagggaatg aatgggcaga gagcaggaat gtgggacatc tgtgttcaag ggaaggactc 960
caggagtctg ctgggaatga ggcctagtag gaaatgaggt ggcccttgag ggtacagaac 1020
aggttcattc ttcgccaaat tcccagcacc ttgcaggcac ttacagctga gtgagataat 1080
gcctgggtta tgaaatcaaa aagttggaaa gcaggtcaga ggtcatctgg tacagccctt 1140
ccttcccttt tttttttttt tttttttttg tgagacaagg tctctctctg ttgcccaggc 1200
tggagtggcg caaacacagc tcactgcagc ctcaacctac tgggctcaag caatcctcca 1260
gcctcagcct cccaaagtgc tgggattaca agcatgagcc accccactca gccctttcct 1320
tcctttttaa ttgatgcata ataattgtaa gtattcatca tggtccaacc aacccttttct 1380 tgacccacct tcctagagag agggtcctct tgattcagcg gtcagggccc cagacccatg 1440
gtctggctcc aggtaccacc tgcctcatgc aggagttggc gtgcccagga agctctgcct 1500
ctgggcacag tgacctcagt ggggtgaggg gagctctccc catagctggg ctgcggccca 1560
accccacccc ctcaggctat gccagggggt gttgccaggg gcacccgggc atcgccagtc 1620
tagcccactc cttcataaag ccctcgcatc ccaggagcga gcagagccag agcat 1675

<210> SEQ ID NO 18
<211> LENGTH: 60
<212> TYPE: DNA
<213> ORGANISM: Artificial Sequence
<220> FEATURE:
<223> OTHER INFORMATION: recombinant polynucleotide

<400> SEQUENCE: 18
gaggaggagg agagagaccg ggagggcgcc cgggaggcag ggcgcgcgca cactccgagg 60

<210> SEQ ID NO 19
<211> LENGTH: 60
<212> TYPE: DNA
<213> ORGANISM: Artificial Sequence
<220> FEATURE:

<223> OTHER INFORMATION: recombinant polynucleotide

<400> SEQUENCE: 19
gatgctgacg aaggctcgcg aggctgtgag cagccacagt gccctgctca gaagccccgg 60

<210> SEQ ID NO 20
<211> LENGTH: 969
<212> TYPE: DNA
<213> ORGANISM: Artificial Sequence
<220> FEATURE:
<223> OTHER INFORMATION: recombinant polynucleotide

<400> SEQUENCE: 20
aggttaattt ttaaaaagca gtcaaaagtc caagtggccc ttggcagcat ttactctctc 60
tgtttgctct ggttaataat ctcaggagca caaacattcc agatccaggt taatttttaa 120
aaagcagtca aaagtccaag tggcccttgg cagcatttac tctctctgtt tgctctggtt 180
aataatctca ggagcacaaa cattccagat ccggcgcgcc agggctggaa gctacctttg 240
tctagaaggc tcagaggcac acaggagttt ctgggctcac cctgccccct tccaacccct 300
cagttcccat cctccagcag ctgtttgtgt gctgcctctg aagtccacac tgaacaaact 360
tcagcctact catgtcccta aaatgggcaa acattgcaag cagcaaacag caaacacaca 420
gccctccctg cctgctgacc ttggagctgg ggcagaggtc agagacctct ctgggcccat 480
gccacctcca acatccactc gaccccttgg aatttcggtg gagaggagca gaggttgtcc 540
tggcgtggtt taggtagtgt gagaggggta cccggggatc ttgctaccag tggaacagcc 600
actaaggatt ctgcagtgag agcagagggc cagctaagtg gtactctccc agagactgtc 660
tgactcacgc caccccctcc accttggaca caggacgctg tggtttctga gccaggtaca 720
atgactcctt tcggtaagtg cagtggaagc tgtacactgc ccaggcaaag cgtccgggca 780
gcgtaggcgg gcgactcaga tcccagccag tggacttagc cctgtttgc tcctccgata 840 actggggtga ccttggttaa tattcaccag cagcctcccc cgttgcccct ctggatccac 900
tgcttaaata cggacgagga cagggccctg tctcctcagc ttcaggcacc accactgacc 960
tgggacagt 969

<210> SEQ ID NO 21
<211> LENGTH: 1050
<212> TYPE: DNA
<213> ORGANISM: Artificial Sequence
<220> FEATURE:
<223> OTHER INFORMATION: recombinant polynucleotide

<400> SEQUENCE: 21
aggctcagag gcacacagga gtttctgggc tcaccctgcc cccttccaac ccctcagttc 60
ccatcctcca gcagctgttt gtgtgctgcc tctgaagtcc acactgaaca aacttcagcc 120
tactcatgtc cctaaaatgg gcaaacattg caagcagcaa acagcaaaca cacagccctc 180
cctgcctgct gaccttggag ctggggcaga ggtcagagac ctctctgggc ccatgccacc 240
tccaacatcc actcgacccc ttggaatttc ggtggagagg agcagaggtt gtcctggcgt 300
ggtttaggta gtgtgagagg gtctagaagg ctcagaggca cacaggagtt tctgggctca 360
ccctgccccc ttccaacccc tcagttccca tcctccagca gctgtttgtg tgctgcctct 420
gaagtccaca ctgaacaaac ttcagcctac tcatgtccct aaaatgggca aacattgcaa 480
gcagcaaaca gcaaacacac agccctccct gcctgctgac cttggagctg gggcagaggt 540
cagagacctc tctgggccca tgccacctcc aacatccact cgaccccttg gaatttcggt 600
ggagaggagc agaggttgtc ctggcgtggt ttaggtagtg tgagaggggt acccggggat 660
cttgctacca gtggaacagc cactaaggat tctgcagtga gagcagaggg ccagctaagt 720
ggtactctcc cagagactgt ctgactcacg ccaccccctc caccttggac acaggacgct 780
gtggtttctg agccaggtac aatgactcct ttcggtaagt gcagtggaag ctgtacactg 840
cccaggcaaa gcgtccgggc agcgtaggcg ggcgactcag atcccagcca gtggacttag 900
cccctgtttg ctcctccgat aactggggtg accttggtta atattcacca gcagcctccc 960
ccgttgcccc tctggatcca ctgcttaaat acggacgagg acagggccct gtctcctcag 1020
cttcaggcac caccactgac ctgggacagt 1050

<210> SEQ ID NO 22
<211> LENGTH: 1089
<212> TYPE: DNA
<213> ORGANISM: Artificial Sequence
<220> FEATURE:
<223> OTHER INFORMATION: recombinant polynucleotide

<400> SEQUENCE: 22
aggttaattt ttaaaaagca gtcaaaagtc caagtggccc ttggcagcat ttactctctc 60
tgtttgctct ggttaataat ctcaggagca caaacattcc agatccaggt taatttttaa 120
aaagcagtca aaagtccaag tggcccttgg cagcatttac tctctctgtt tgctctggtt 180
aataatctca ggagcacaaa cattccagat ccggcgcgcc agggctggaa gctacctttg 240
acatcatttc ctctgcgaat gcatgtataa tttctacaga acctattaga aaggatcacc 300
cagcctctgc ttttgtacaa ctttccctta aaaaactgcc aattccactg ctgtttggcc 360
caatagtgag aactttttcc tgctgcctct tggtgctttt gcctatggcc cctattctgc 420
ctgctgaaga cactcttgcc agcatggact taaacccctc cagctctgac aatcctcttt 480
ctcttttgtt ttacatgaag ggtctggcag ccaaagcaat cactcaaagt tcaaacctta 540 tcatttttttg ctttgttcct cttggccttg gttttgtaca tcagctttga aaataccatc 600
ccagggttaa tgctggggtt aatttataac taagagtgct ctagttttgc aatacaggac 660
atgctataaa aatggaaaga tgttgctttc tgagaggatc ttgctaccag tggaacagcc 720
actaaggatt ctgcagtgag agcagagggc cagctaagtg gtactctccc agagactgtc 780
tgactcacgc caccccctcc accttggaca caggacgctg tggtttctga gccaggtaca 840
gtgactcctt tcggtaagtg cagtggaagc tgtacactgc ccaggcaaag cgtccgggca 900
gcgtaggcgg gcgactcaga tcccagccag tggacttagc ccctgtttgc tcctccgata 960
actggggtga ccttggttaa tattcaccag cagcctcccc cgttgcccct ctggatccac 1020
tgcttaaata cggacgagga cagggccctg tctcctcagc ttcaggcacc accactgacc 1080
tgggacagt 1089

<210> SEQ ID NO 23
<211> LENGTH: 1430
<212> TYPE: DNA
<213> ORGANISM: Artificial Sequence
<220> FEATURE:
<223> OTHER INFORMATION: recombinant polynucleotide

<400> SEQUENCE: 23
aggctcagag gcacacagga gtttctgggc tcaccctgcc cccttccaac ccctcagttc 60
ccatcctcca gcagctgttt gtgtgctgcc tctgaagtcc acactgaaca aacttcagcc 120

```
tactcatgtc cctaaaatgg gcaaacattg caagcagcaa acagcaaaca cacagccctc    180
cctgcctgct gaccttggag ctggggcaga ggtcagagac ctctctgggc ccatgccacc    240
tccaacatcc actcgacccc ttggaatttc ggtggagagg agcagaggtt gtcctggcgt    300
ggtttaggta gtgtgagagg gtctagagcc cttaagctag caggttaatt tttaaaaagc    360
agtcaaaagt ccaagtggcc cttggcagca tttactctct ctgtttgctc tggttaataa    420
tctcaggagc acaaacattc cagatccagg ttaattttta aaaagcagtc aaaagtccaa    480
gtggcccttg gcagcattta ctctctctgt ttgctctggt taataatctc aggagcacaa    540
acattccaga tccggcgcgc cagggctgga agctaccttt gacatcattt cctctgcgaa    600
tgcatgtata atttctacag aacctattag aaaggatcac ccagcctctg cttttgtaca    660
actttccctt aaaaaactgc caattccact gctgtttggc ccaatagtga gaactttttc    720
ctgctgcctc ttggtgcttt tgcctatggc ccctattctg cctgctgaag acactcttgc    780
cagcatggac ttaaacccct ccagctctga caatcctctt tctcttttgt tttacatgaa    840
gggtctggca gccaaagcaa tcactcaaag ttcaaacctt atcatttttt gctttgttcc    900
tcttggcctt ggttttgtac atcagctttg aaaataccat cccagggtta atgctggggt    960
taatttataa ctaagagtgc tctagttttg caatacagga catgctataa aaatggaaag   1020
atgttgcttt ctgagaggat cttgctacca gtggaacagc cactaaggat tctgcagtga   1080
gagcagaggg ccagctaagt ggtactctcc cagagactgt ctgactcacg ccaccccctc   1140
caccttggac acaggacgct gtggtttctg agccaggtac agtgactcct ttcggtaagt   1200
gcagtggaag ctgtacactg cccaggcaaa gcgtccgggc agcgtaggcg ggcgactcag   1260
atcccagcca gtggacttag cccctgtttg ctcctccgat aactggggtg accttggtta   1320
atattcacca gcagcctccc ccgttgcccc tctggatcca ctgcttaaat acggacgagg   1380
acagggccct gtctcctcag cttcaggcac caccactgac ctgggacagt              1430
```

<210> SEQ ID NO 24
<211> LENGTH: 1318
<212> TYPE: DNA
<213> ORGANISM: Artificial Sequence
<220> FEATURE:
<223> OTHER INFORMATION: recombinant polynucleotide

<400> SEQUENCE: 24

```
aggttaattt ttaaaaagca gtcaaaagtc caagtggccc ttggcagcat ttactctctc     60
tgtttgctct ggttaataat ctcaggagca caaacattcc agatccaggt taatttttaa    120
aaagcagtca aaagtccaag tggcccttgg cagcatttac tctctctgtt tgctctggtt    180
aataatctca ggagcacaaa cattccagat ccggcgcgcc agggctggaa gctacctttg    240
acatcatttc ctctgcgaat gcatgtataa tttctacaga acctattaga aaggatcacc    300
cagcctctgc ttttgtacaa ctttccctta aaaaactgcc aattccactg ctgtttggcc    360
caatagtgag aactttttcc tgctgcctct tggtgctttt gcctatggcc cctattctgc    420
ctgctgaaga cactcttgcc agcatggact taaacccctc cagctctgac aatcctcttt    480
ctcttttgtt ttacatgaag ggtctggcag ccaaagcaat cactcaaagt tcaaacctta    540
tcattttttg ctttgttcct cttggccttg gttttgtaca tcagctttga aaataccatc    600
ccagggttaa tgctggggtt aatttataac taagagtgct ctagttttgc aatacaggac    660
atgctataaa aatggaaaga tgttgctttc tgagaggatc ttgctaccag tggaacagcc    720
actaaggatt ctgcagtgag agcagagggc cagctaagtg gtactctccc agagactgtc    780
```

```
tgactcacgc cacccccctcc accttggaca caggacgctg tggtttctga gccaggtaca    840

gtgactcctt tcggtaagtg cagtggaagc tgtacactgc ccaggcaaag cgtccgggca    900

gcgtaggcgg gcgactcaga tcccagccag tggacttagc cctgtttgc tcctccgata    960

actggggtga ccttggttaa tattcaccag cagcctcccc cgttgcccct ctggatccac   1020

tgcttaaata cggacgagga cagggccctg tctcctcagc ttcaggcacc accactgacc   1080

tgggacagta aaacaggtaa gtccgctgtt tgtgtgctgc ctctgaagtc cacactgaac   1140

aaacttcagc ctactcatgt ccctaaaatg ggcaaacatt gcaagcagca aacagcaaac   1200

acacagccct ccctgcctgc tgaccttgga gctggggcag aggtcagaga cctctctggc   1260

ctctactaac catgttcatg ttttcttttt ttttctacag gtcctgggtg acgaacag     1318
```

```
<210> SEQ ID NO 25
<211> LENGTH: 1579
<212> TYPE: DNA
<213> ORGANISM: Artificial Sequence
<220> FEATURE:
<223> OTHER INFORMATION: recombinant polynucleotide

<400> SEQUENCE: 25
```

```
aggctcagag gcacacagga gtttctgggc tcaccctgcc cccttccaac ccctcagttc     60

ccatcctcca gcagctgttt gtgtgctgcc tctgaagtcc acactgaaca aacttcagcc    120

tactcatgtc cctaaaatgg gcaaacattg caagcagcaa acagcaaaca cacagccctc    180

cctgcctgct gaccttggag ctggggcaga ggtcagagac ctctctgggc ccatgccacc    240

tccaacatcc actcgacccc ttggaatttc ggtggagagg agcagaggtt gtcctggcgt    300

ggtttaggta gtgtgagagg gccactacgg gtttaggctg cccatgtaag gaggcaaggc    360

ctggggacac ccgagatgcc tggttataat taacccagac atgtggctgc cccccccccc    420

cccaacacct gctgcctcta aaaataaccc tgtccctggt ggatcccact acgggtttag    480

gctgcccatg taaggaggca aggcctgggg acacccgaga tgcctggtta taattaaccc    540

agacatgtgg ctgccccccc cccccccaac acctgctgcc tctaaaaata accctgtccc    600

tggtggatcc cactacgggt ttaggctgcc catgtaagga ggcaaggcct ggggacaccc    660

gagatgcctg gttataatta acccagacat gtggctgccc cccccccccc caacacctgc    720

tgcctctaaa aataaccctg tccctggtgg atcccctgca tgcgaagatc ttcgaacaag    780

gctgtggggg actgagggca ggctgtaaca ggcttggggg ccagggctta tacgtgcctg    840

ggactcccaa agtattactg ttccatgttc ccggcgaagg gccagctgtc ccccgccagc    900

tagactcagc acttagttta ggaaccagtg agcaagtcag cccttggggc agcccataca    960

aggccatggg gctgggcaag ctgcacgcct gggtccgggg tgggcacggt gcccgggcaa   1020

cgagctgaaa gctcatctgc tctcaggggc ccctccctgg ggacagcccc tcctggctag   1080

tcacaccctg taggctcctc tatataaccc aggggcacag gggctgccct cattctacca   1140

ccacctccac agcacagaca gacactcagg agccagccag cgtcgagatc ttgctaccag   1200

tggaacagcc actaaggatt ctgcagtgag agcagagggc cagctaagtg gtactctccc   1260

agagactgtc tgactcacgc cacccccctcc accttggaca caggacgctg tggtttctga   1320

gccaggtaca gtgactcctt tcggtaagtg cagtggaagc tgtacactgc ccaggcaaag   1380

cgtccgggca gcgtaggcgg gcgactcaga tcccagccag tggacttagc cctgtttgc    1440

tcctccgata actggggtga ccttggttaa tattcaccag cagcctcccc cgttgcccct   1500
```

ctggatccac tgcttaaata cggacgagga cagggccctg tctcctcagc ttcaggcacc 1560
accactgacc tgggacagt 1579

<210> SEQ ID NO 26
<211> LENGTH: 100
<212> TYPE: DNA
<213> ORGANISM: Artificial Sequence
<220> FEATURE:
<223> OTHER INFORMATION: recombinant polynucleotide

<400> SEQUENCE: 26
aggttaattt ttaaaaagca gtcaaaagtc caagtggccc ttggcagcat ttactctctc 60
tgtttgctct ggttaataat ctcaggagca caaacattcc 100

<210> SEQ ID NO 27
<211> LENGTH: 100
<212> TYPE: DNA
<213> ORGANISM: Artificial Sequence
<220> FEATURE:
<223> OTHER INFORMATION: recombinant polynucleotide

<400> SEQUENCE: 27
aggttaattt ttaaaaagca gtcaaaagtc caagtggccc ttggcagcat ttactctctc 60
tgtttgctct ggttaataat ctcaggagca caaacattcc 100

<210> SEQ ID NO 28
<211> LENGTH: 321
<212> TYPE: DNA
<213> ORGANISM: Artificial Sequence
<220> FEATURE:
<223> OTHER INFORMATION: recombinant polynucleotide

<400> SEQUENCE: 28
aggctcagag gcacacagga gtttctgggc tcaccctgcc cccttccaac ccctcagttc 60
ccatcctcca gcagctgttt gtgtgctgcc tctgaagtcc acactgaaca aacttcagcc 120
tactcatgtc cctaaaatgg gcaaacattg caagcagcaa acagcaaaca cacagccctc 180
cctgcctgct gaccttggag ctggggcaga ggtcagagac ctctctgggc ccatgccacc 240
tccaacatcc actcgacccc ttggaatttc ggtggagagg agcagaggtt gtcctggcgt 300
ggtttaggta gtgtgagagg g 321

<210> SEQ ID NO 29
<211> LENGTH: 554
<212> TYPE: DNA
<213> ORGANISM: Artificial Sequence
<220> FEATURE:
<223> OTHER INFORMATION: recombinant polynucleotide

<400> SEQUENCE: 29
aggctcagag gcacacagga gtttctgggc tcaccctgcc cccttccaac ccctcagttc 60
ccatcctcca gcagctgttt gtgtgctgcc tctgaagtcc acactgaaca aacttcagcc 120
tactcatgtc cctaaaatgg gcaaacattg caagcagcaa acagcaaaca cacagccctc 180
cctgcctgct gaccttggag ctggggcaga ggtcagagac ctctctgggc ccatgccacc 240
tccaacatcc actcgacccc ttggaatttc ggtggagagg agcagaggtt gtcctggcgt 300
ggtttaggta gtgtgagagg gtctagaagg ctcagaggca cacaggagtt tctgggctca 360
ccctgccccc ttccaacccc tcagttccca tcctccagca gctgtttgtg tgctgcctct 420
gaagtccaca ctgaacaaac ttcagcctac tcatgtccct aaaatgggca aacattgcaa 480
gcagcaaaca gcaaacacac agccctccct gcctgctgac cttggagctg gggcagaggt 540
cagagacctc tctg 554

<210> SEQ ID NO 30
<211> LENGTH: 460
<212> TYPE: DNA
<213> ORGANISM: Artificial Sequence
<220> FEATURE:
<223> OTHER INFORMATION: recombinant polynucleotide

<400> SEQUENCE: 30
gggctggaag ctacctttga catcatttcc tctgcgaatg catgtataat ttctacagaa 60
cctattagaa aggatcaccc agcctctgct tttgtacaac tttcccttaa aaaactgcca 120
attccactgc tgtttggccc aatagtgaga actttttcct gctgcctctt ggtgcttttg 180
cctatggccc ctattctgcc tgctgaagac actcttgcca gcatggactt aaacccctcc 240
agctctgaca atcctctttc tcttttgttt tacatgaagg gtctggcagc caaagcaatc 300
actcaaagtt caaaccttat catttttgc tttgttcctc ttggccttgg ttttgtacat 360
cagctttgaa aataccatcc cagggttaat gctggggtta atttataact aagagtgctc 420
tagttttgca atacaggaca tgctataaaa atggaaagat 460

<210> SEQ ID NO 31
<211> LENGTH: 393
<212> TYPE: DNA
<213> ORGANISM: Artificial Sequence
<220> FEATURE:
<223> OTHER INFORMATION: recombinant polynucleotide

<400> SEQUENCE: 31
gatcttgcta ccagtggaac agccactaag gattctgcag tgagagcaga gggccagcta 60
agtggtactc tcccagagac tgtctgactc acgccacccc ctccaccttg gacacaggac 120
gctgtggttt ctgagccagg tacaatgact cctttcggta agtgcagtgg aagctgtaca 180
ctgcccaggc aaagcgtccg ggcagcgtag gcgggcgact cagatcccag ccagtggact 240
tagcccctgt ttgctcctcc gataactggg gtgaccttgg ttaatattca ccagcagcct 300
cccccgttgc ccctctggat ccactgctta aatacggacg aggacagggc cctgtctcct 360
cagcttcagg caccaccact gacctgggac agt 393

<210> SEQ ID NO 32
<211> LENGTH: 144
<212> TYPE: DNA
<213> ORGANISM: Artificial Sequence
<220> FEATURE:
<223> OTHER INFORMATION: recombinant polynucleotide

<400> SEQUENCE: 32
ccactacggg tttaggctgc ccatgtaagg aggcaaggcc tggggacacc cgagatgcct 60
ggttataatt aacccagaca tgtggctgcc cccccccccc ccaacacctg ctgcctctaa 120
aaataaccct gtccctggtg gatc 144

<210> SEQ ID NO 33
<211> LENGTH: 288
<212> TYPE: DNA
<213> ORGANISM: Artificial Sequence
<220> FEATURE:
<223> OTHER INFORMATION: recombinant polynucleotide

<400> SEQUENCE: 33
ccactacggg tttaggctgc ccatgtaagg aggcaaggcc tggggacacc cgagatgcct 60
ggttataatt aacccagaca tgtggctgcc cccccccccc ccaacacctg ctgcctctaa 120
aaataaccct gtccctggtg gatcccacta cgggtttagg ctgcccatgt aaggaggcaa 180
ggcctgggga cacccgagat gcctggttat aattaaccca gacatgtggc tgcccccccc 240
ccccccaaca cctgctgcct ctaaaaataa ccctgtccct ggtggatc 288

<210> SEQ ID NO 34
<211> LENGTH: 432
<212> TYPE: DNA
<213> ORGANISM: Artificial Sequence
<220> FEATURE:
<223> OTHER INFORMATION: recombinant polynucleotide

<400> SEQUENCE: 34
ccactacggg tttaggctgc ccatgtaagg aggcaaggcc tggggacacc cgagatgcct 60
ggttataatt aacccagaca tgtggctgcc cccccccccc ccaacacctg ctgcctctaa 120
aaataaccct gtccctggtg gatcccacta cgggtttagg ctgcccatgt aaggaggcaa 180
ggcctgggga cacccgagat gcctggttat aattaaccca gacatgtggc tgcccccccc 240
ccccccaaca cctgctgcct ctaaaaataa ccctgtccct ggtggatccc actacgggtt 300
taggctgccc atgtaaggag gcaaggcctg gggacacccg agatgcctgg ttataattaa 360
cccagacatg tggctgcccc cccccccccc aacacctgct gcctctaaaa ataaccctgt 420
ccctggtgga tc 432

<210> SEQ ID NO 35
<211> LENGTH: 837
<212> TYPE: DNA
<213> ORGANISM: Artificial Sequence
<220> FEATURE:
<223> OTHER INFORMATION: recombinant polynucleotide

<400> SEQUENCE: 35
gtgagcggcg gatgcccttc tcctctggct gtaattagtc ttggtttact tgtttctttt 60
ctgtggctgt tgaaagcctt gaggggctct ggagggccct ttgtgtgggg gagtgcttgg 120
gggtgttgtt gtgtgtgtgt tggggagtct ttgtgctctt ctgcctgtgc tgtgagtctg 180
tggttgttgg gctttgtgtc tctcagtgtg ttaggggagt tgctggggtg tgcccttgtg 240 tggggggct gtaggggaac aaaggctgtt gtgggtgtgt gttgggggg tgagcagggg 300 gtgtgggttt tgttggctgc aacccccct gcaccccct ccctagttgc tgagcatgcc 360
tgctttggtg tgggctctta tgggttggtt gggcttcttg ctggtgggg tggtgcaggt 420 gggggtgctg gtgggtgggc tccttggctg ggagggcttg gggaggggtt gtgcccctga 480
gtctgtgctg ttaggttgta gctcagccat tgcctttttt gtagagggtc agggacttcc 540
tttgtcccaa atctgtgtga gctaaatctg ggaggtctct cacccctct agtggttggg 600 taagtgtgtg tctgcaggaa ggaaagggtg ggagggcctt ttgtttcttc tcttcccctt 660
ctccctctcc agccttgggc tgtcttgggg gatgctgcct ttgggggat gggcagggtg 720 ggtttgcttc tggttgtgac tgtgctctag agcctctgct aacctgttct gccttcttct 780
ttttcctaca gctcctgggc aattgctggt tattgtgctg tctctatttt ggcaaag 837

<210> SEQ ID NO 36
<211> LENGTH: 82

<212> TYPE: DNA
<213> ORGANISM: Artificial Sequence
<220> FEATURE:
<223> OTHER INFORMATION: recombinant polynucleotide

<400> SEQUENCE: 36
gtgagtatct cagggatcca gacatgggga tatgggaggt gcctctgatc ccagggctca 60
ctgtgggtct ctctgttcac ag 82

<210> SEQ ID NO 37
<211> LENGTH: 133
<212> TYPE: DNA
<213> ORGANISM: Artificial Sequence
<220> FEATURE:
<223> OTHER INFORMATION: recombinant polynucleotide

<400> SEQUENCE: 37
gtaagtatca aggttacaag acaggtttaa ggagaccaat agaaactggg cttgtcgaga 60
cagagaagac tcttgcgttt ctgataggca cctattggtc ttactgacat ccactttgcc 120
tttctctcca cag 133

<210> SEQ ID NO 38
<211> LENGTH: 97
<212> TYPE: DNA
<213> ORGANISM: Artificial Sequence
<220> FEATURE:
<223> OTHER INFORMATION: recombinant polynucleotide

<400> SEQUENCE: 38
gtaagtttag tctttttgtc ttttatttca ggtcccggat ccggtggtgg tgcaaatcaa 60
agaactgctc ctcagtggat gttgccttta cttctag 97

<210> SEQ ID NO 39
<211> LENGTH: 125
<212> TYPE: DNA
<213> ORGANISM: Artificial Sequence
<220> FEATURE:
<223> OTHER INFORMATION: recombinant polynucleotide

<400> SEQUENCE: 39
gtaagtatca aggttacaag acaggtttaa ggagaccaat agaaactggg cttgtcgaga 60
cagagaagac tcttgcgttt ctgataggca cctattggtc ttactgacat ccactttgcc 120
tttct 125

<210> SEQ ID NO 40
<211> LENGTH: 127
<212> TYPE: DNA
<213> ORGANISM: Artificial Sequence
<220> FEATURE:
<223> OTHER INFORMATION: recombinant polynucleotide

<400> SEQUENCE: 40
gatctttttc cctctgccaa aaattatggg gacatcatga agccccttga gcatctgact 60
tctggctaat aaaggaaatt tattttcatt gcaatagtgt gttggaattt tttgtgtctc 120
tcactcg 127

<210> SEQ ID NO 41
<211> LENGTH: 50
<212> TYPE: DNA
<213> ORGANISM: Artificial Sequence
<220> FEATURE:

-continued

```
<223> OTHER INFORMATION: recombinant polynucleotide

<400> SEQUENCE: 41

aggcctaata aagagctcag atgcatcgat cagagtgtgt tggtttttg               50


<210> SEQ ID NO 42
<211> LENGTH: 129
<212> TYPE: DNA
<213> ORGANISM: Artificial Sequence
<220> FEATURE:
<223> OTHER INFORMATION: recombinant polynucleotide

<400> SEQUENCE: 42

cgcgcgctcg ctcgctcact gaggccgccc gggcaaagcc cgggcgtcgg gcgacctttg     60

gtcgcccggc ctcagtgagc gagcgagcgc gcagagaggg agtggccaac tccatcacta    120

ggggttcct                                                            129


<210> SEQ ID NO 43
<211> LENGTH: 130
<212> TYPE: DNA
<213> ORGANISM: Artificial Sequence
<220> FEATURE:
<223> OTHER INFORMATION: recombinant polynucleotide

<400> SEQUENCE: 43

aggaacccct agtgatggag ttggccactc cctctctgcg cgctcgctcg ctcactgagg     60

ccgggcgacc aaaggtcgcc cgacgcccgg gctttgcccg ggcggcctca gtgagcgagc    120

gagcgcgcag                                                           130


<210> SEQ ID NO 44
<211> LENGTH: 60
<212> TYPE: DNA
<213> ORGANISM: Artificial Sequence
<220> FEATURE:
<223> OTHER INFORMATION: recombinant polynucleotide

<400> SEQUENCE: 44

atgtacagaa tgcagctgct gctgctcatt gccctgtctc tggccctggt caccaattct     60
```

AAV VECTORS AND METHODS AND USES THEREOF

CROSS-REFERENCE TO RELATED APPLICATIONS

This application is the U.S. national phase of International Application No. PCT/US2022/027390 filed May 3, 2022, which designated the U.S. and claims the benefit of U.S. Application No. 63/183,999, filed May 4, 2021, the entire contents of each of which are incorporated herein by reference in their entirety.

REFERENCE TO SEQUENCE LISTING SUBMITTED ELECTRONICALLY

The content of the electronically submitted sequence listing (Name 6728-1310_Sequence_Listing.txt; Size: 41 KB; and Date of Creation: Nov. 1, 2023) is incorporated by reference in its entirety.

FIELD OF THE INVENTION

The present invention relates to stuffer polynucleotide sequences to enlarge genome sizes for packaging in adeno-associated virus (AAV) vectors.

BACKGROUND

Viral vector production is highly complex. AAV packaging capacity of <5 kb limits the size of the genome that can be encapsidated by recombinant viral capsid. The genome is flanked by inverted terminal repeats (ITRs) which are cis elements required for packaging the genome. Viral vector delivery of therapeutic genomes typically contain regulatory elements such as promoter regions to drive expression of a gene of interest and a polyA tail. It has been shown that the packaging of oversized genomes proved inefficient, with a majority of only partial AAV genomes being packaged (Wu, Z. et al. 2010 Mol Ther. 18(1):80-86, published online 10 Nov. 2009), whereas undersized genomes flanked by ITRs can present challenges to viral vector production and administration of gene therapies thus, requiring further engineering to maintain optimum vector (genome) sizes.

Stuffer or filler DNA sequences have found utility in minimizing process-related impurities, and improving infectivity and stability of AAV capsids, thereby improving the benefit of AAV gene therapies for a variety of therapeutic transgenes (Hauck, B., et al. 2009 Mol Ther. 17(1):144-152, published online 21 Oct. 2008; Horowitz, E. D. et al. 2013 J Virol 87(6):2994-3002). Transgenes delivered with AAV or other viral vectors aim to provide long-term gene expression, therefore methods to stabilize vectors in mammalian cells or tissue systems would be of benefit. As such, improved AAV systems for gene therapy would greatly benefit patients, thus, there remains a need for development of non-coding regions in vector-based therapies.

SUMMARY OF THE INVENTION

Provided are recombinant expression cassettes comprising a stuffer (or filler) polynucleotide sequence for extending the transgene size of any heterologous gene, for example a gene of Table 2. In some embodiments, a stuffer (or filler) polynucleotide sequence comprises SEQ ID NO: 1, or a fragment of SEQ ID NO:1 between 1-10, 10-20, 20-30, 30-40, 40-50, 50-60, 60-75, 75-100, 100-150, 150-200, 200-250, 250-300, 300-400, 400-500, 500-600, 600-750, 750-1,000, 1,000-1,500, 1,500-1,601, nucleotides in length. In other embodiments, a stuffer (or filler) polynucleotide sequence comprises SEQ ID NO:5, or a fragment of SEQ ID NO: 1 between 1-10, 10-20, 20-30, 30-40, 40-50, 50-60, 60-75, 75-100, 100-150, 150-200, 200-250, 250-300, 300-400, 400-500, 500-600, 600-750, 750-1,000, 1,000-1,500, 1,500-2001, nucleotides in length. In some embodiments, the stuffer polynucleotide sequence has a length that when combined with the heterologous gene sequence, the total combined length of the heterologous gene sequence and stuffer polynucleotide sequence is between about 2.4-5.2 kb, between about 3.1-4.7 kb, or between about 3.4-4.7 kb. The transgene may comprise any one of the genes or nucleic acids encoding a therapeutic gene listed in, but not limited to, Tables 3A-3C.

Provided are stuffer (or filler) polynucleotides comprising nucleic acid sequences SEQ ID NO:1, SEQ ID NO:2, SEQ ID NO:3, SEQ ID NO:4, or SEQ ID NO:5, or a fragment or fragments thereof.

Also provided are vectors comprising an expression cassette comprising SEQ ID NO:1, or one or more fragments of SEQ ID NO:1 between 1-10, 10-20, 20-30, 30-40, 40-50, 50-60, 60-75, 75-100, 100-150, 150-200, 200-250, 250-300, 300-400, 400-500, 500-600, 600-750, 750-1,000, 1,000-1,500, or 1,500-1601 nucleotides in length. In some embodiments, the expression cassette comprises SEQ ID NO:5, or one or more fragments of SEQ ID NO:5 between 1-10, 10-20, 20-30, 30-40, 40-50, 50-60, 60-75, 75-100, 100-150, 150-200, 200-250, 250-300, 300-400, 400-500, 500-600, 600-750, 750-1,000, 1,000-1,500, or 1,500-2001 nucleotides in length. In some embodiments, the expression cassette comprises SEQ ID NO:1, SEQ ID NO:2, SEQ ID NO:3, SEQ ID NO:4, or SEQ ID NO:5, or a fragment thereof. In some embodiments, the expression cassette comprises one or more nucleic acid sequences SEQ ID NO:1, SEQ ID NO:2, SEQ ID NO:3, SEQ ID NO:4, or SEQ ID NO:5, or a fragment or fragments thereof. In some embodiments, the expression cassette further comprises a nucleic acid sequence encoding a heterologous gene. In some embodiments, the expression cassette further comprises one or more promoters, and a polyA downstream of the gene coding sequence. In some embodiments, the expression cassette directs expression of the transgene in target tissues, e.g. comprising the gene listed in, but not limited to, Tables 3A-3C. In some embodiments, the vectors comprise a transgene operably linked to SEQ ID NO:1, SEQ ID NO:2, SEQ ID NO:3, SEQ ID NO:4, or SEQ ID NO:5, or a fragment or fragments thereof. In some embodiments, the vectors comprise a heterologous gene operably linked to SEQ ID NO:1, SEQ ID NO:2, SEQ ID NO:3, SEQ ID NO:4, or SEQ ID NO:5, or a fragment or fragments thereof. In some embodiments, the vectors comprise a heterologous gene encoding a microRNA (miRNA), a short hairpin RNA (shRNA), an antibody, an antigen-binding fragment, a Fc-fusion protein, or an enzyme.

Also provided are methods for enhancing expression of a transgene, comprising delivery of viral vectors comprising nucleic acid expression cassettes having a 5' to 3' arrangement of a 5'-ITR, promoter, optionally an enhancer or intron, a heterologous gene, a polyA, a stuffer (SEQ ID NO:1, SEQ ID NO:2, SEQ ID NO:3, SEQ ID NO:4, or SEQ ID NO:5, or a fragment or fragments thereof), and a 3'-ITR. In some embodiments, provided are viral vectors incorporating the engineered expression cassettes described herein, including rAAVs.

In another aspect, a method of treatment by delivery of rAAVs comprising the nucleic acid expression cassettes described herein are also provided. A method for treating a disease or disorder in a subject in need thereof comprising the administration of recombinant AAV particles comprising an expression cassette having a heterologous gene, a polyA, a stuffer polynucleotide comprising SEQ ID NO:1. SEQ ID NO:2, SEQ ID NO:3, SEQ ID NO:4, or SEQ ID NO:5, or a fragment or fragments thereof, is provided.

The invention is illustrated by way of examples infra describing the construction and function of gene cassettes engineered with stuffer polynucleotide sequences.

DETAILED DESCRIPTION

Figure 1:
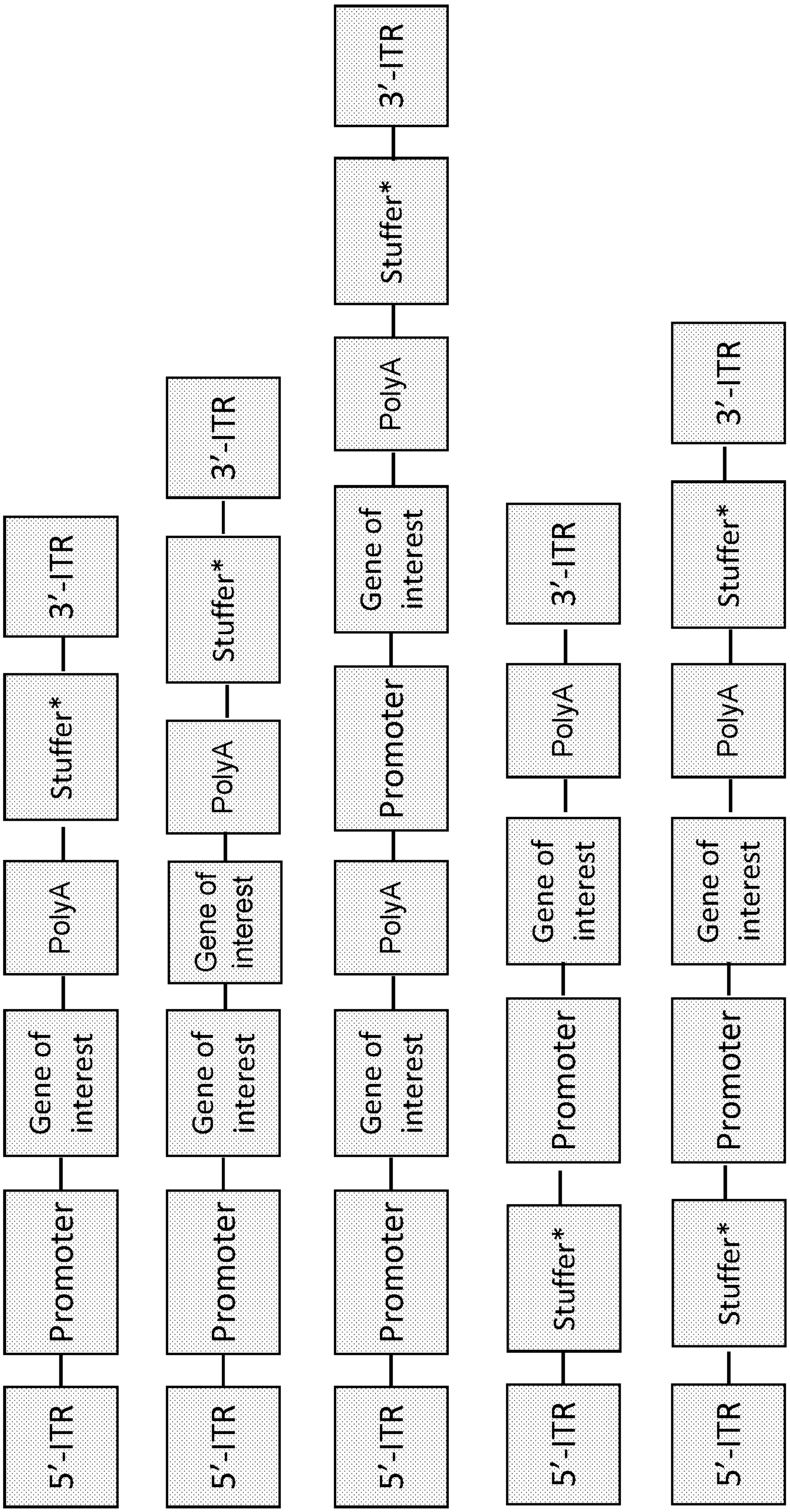
FIG. 1 depicts construction of recombinant nucleic acid expression cassettes, flanked by ITRs. Asterisk (*) indicates that stuffer sequence may comprise more than one polynucleotide stuffer sequence described herein or fragments of such polynucleotide stuffer sequences.

The inventors have provided, in part, unique polynucleotide sequences useful as inert stuffer (or filler) sequences in expression cassettes, particularly useful for transgene expression delivered as viral vectors, incorporating the engineered expression cassettes described herein, including rAAVs, for use in therapy. The novel nucleic acids were identified as inert, non-coding sequences (e.g. cDNA depleted of any translation or "initiation" sites). Ultimately, these designs may improve the manufacturing and therapeutic utility of gene transfer by enhancing transduction, improving stability, and limiting any cytotoxicity of gene transfer therapies.

Definitions

The term "AAV" or "adeno-associated virus" refers to a Dependoparvovirus within the Parvoviridae genus of viruses. The AAV can be an AAV derived from a naturally occurring "wild-type" virus, an AAV derived from a rAAV genome packaged into a capsid comprising capsid proteins encoded by a naturally occurring cap gene and/or from a rAAV genome packaged into a capsid comprising capsid proteins encoded by a non-naturally occurring capsid cap gene. An example of the latter includes a rAAV having a capsid protein comprising a peptide insertion into the amino acid sequence of the naturally-occurring capsid.

The term "rAAV" refers to a "recombinant AAV." In some embodiments, a recombinant AAV has an AAV genome in which part or all of the rep and cap genes have been replaced with heterologous sequences.

The term "regulatory element" or "nucleic acid regulatory element" are non-coding nucleic acid sequences that control the transcription of neighboring genes. Cis regulatory elements typically regulate gene transcription by binding to transcription factors.

The term "expression cassette" or "nucleic acid expression cassette" refers to nucleic acid molecules that include one or more transcriptional control elements including, but not limited to promoters, enhancers and/or regulatory elements, introns and polyadenylation sequences. The enhancers and promoters typically function to direct (trans)gene expression in one or more desired cell types, tissues or organs.

The term "operably linked" refers to that the nucleic acid sequences being linked are typically contiguous, or substantially contiguous. Where necessary, operably linked may refer to joining a coding region and a non-coding region, or two protein coding regions in a contiguous manner, e.g. in reading frame. In some instances, for example enhancers which may function when separated from the promoter by several kilobases, also intronic sequences and stuffer sequences may be of variable lengths, and may be operably linked while not directly contiguous with a downstream or upstream promoter and heterologous gene.

The term "rep-cap helper plasmid" refers to a plasmid that provides the viral rep and cap gene function and aids the production of AAVs from rAAV genomes lacking functional rep and/or the cap gene sequences.

The term "cap gene" refers to the nucleic acid sequences that encode capsid proteins that form or help form the capsid coat of the virus. For AAV, the capsid protein may be VP1, VP2, or VP3.

The term "rep gene" refers to the nucleic acid sequences that encode the non-structural protein needed for replication and production of virus.

The terms "nucleic acids" and "nucleotide sequences" include DNA molecules (e.g., cDNA or genomic DNA), RNA molecules (e.g., mRNA), combinations of DNA and RNA molecules or hybrid DNA/RNA molecules, and analogs of DNA or RNA molecules. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably is double-stranded DNA.

The terms "subject", "host", and "patient" are used interchangeably. As used herein, a subject is preferably a mammal such as a non-primate (e.g., cows, pigs, horses, cats, dogs, rats etc.) or a primate (e.g., monkey and human), most preferably a human.

The terms "therapeutic agent" or "therapeutic gene" refer to any agent which can be used in treating, managing, or ameliorating symptoms associated with a disease or disorder, where the disease or disorder is associated with a function to be provided by a transgene. As used herein, a "therapeutically effective amount" refers to the amount of agent, (e.g., an amount of product expressed by the transgene) that provides at least one therapeutic benefit in the treatment or management of the target disease or disorder, when administered to a subject suffering therefrom. Further, a therapeutically effective amount with respect to an agent of the invention means that amount of agent alone, or when in combination with other therapies, that provides at least one therapeutic benefit in the treatment or management of the disease or disorder.

Stuffer Polynucleotide Sequences

One aspect relater to nucleic acids comprising a stuffer (or filler) polynucleotide sequence for extending the transgene size of any heterologous gene, for example a gene of Table 3A-3C. In some embodiments, a stuffer (or filler) polynucleotide sequence comprises SEQ ID NO:1, or a fragment of SEQ ID NO:1 between 1-10, 10-20, 20-30, 30-40, 40-50, 50-60, 60-75, 75-100, 100-150, 150-200, 200-250, 250-300, 300-400, 400-500, 500-600, 600-750, 750-1,000, 1,000-1, 500, 1,500-1,601, nucleotides in length. In other embodiments, a stuffer (or filler) polynucleotide sequence comprises SEQ ID NO:5, or a fragment of SEQ ID NO:1 between 1-10, 10-20, 20-30, 30-40, 40-50, 50-60, 60-75, 75-100, 100-150, 150-200, 200-250, 250-300, 300-400, 400-500, 500-600, 600-750, 750-1,000, 1,000-1,500, 1,500-2001, nucleotides in length. In some embodiments, the stuffer polynucleotides comprise nucleic acid sequences SEQ ID NO:1, SEQ ID NO:2, SEQ ID NO:3, SEQ ID NO:4, or SEQ ID NO:5, or a fragment or fragments thereof.

In some embodiments, the stuffer polynucleotide sequence has a length that when combined with the heterologous gene sequence, the total combined length of the heterologous gene sequence and stuffer polynucleotide sequence is between about 2.4-5.2 kb, or between about 3.1-4.7 kb. The transgene may comprise any one of the genes or nucleic acids encoding a therapeutic gene listed in, but not limited to, Tables 2A-2D.

TABLE 1

| SEQ ID NO: | Non-coding Nucleotide sequences (stuffers) |
|---|---|
| 1 | atagtctatccaggttgagcatcctgctgg<br>tggttacaagaaactgtttgaaactgtgga<br>ggaactgtcctcgccgctcacagctcatgt<br>aacaggcaggatccccctctggctcaccgg<br>cagtctccttcgatgtgggccaggactctt<br>tgaagttggatctgagccattttaccacct<br>gtttgatgggcaagccctcctgcacaagtt<br>tgactttaaagaaggacatgtcacatacca<br>cagaaggttcatccgcactgatgcttacgt<br>acgggcaatgactgagaaaaggatcgtcat<br>aacagaatttggcacctgtgctttcccaga<br>tccctgcaagaatatattttccaggttttt<br>ttcttactttcgaggagtagaggttactga<br>caattgcccttgttaatgtctacccagtgg<br>gggaagattactacgcttgcacagagacca<br>actttattacaaagattaatccagagacct<br>tggagacaattaagcaggttgatctttgca<br>actaagtctctgtcaatggggccactgctc<br>acccccacattgaaaatgatggaaccgttt<br>acaatattggtaattgctttggaaaaaatt<br>tttcaattgcctacaacattgtaaagatcc<br>caccactgcaagcagacaaggaagatccaa<br>taagcaagtcagagatcgttgtacaattcc<br>cctgcagtgaccgattcaagccatcttacg<br>ttcatagttttggtctgactcccaactata<br>tcgtttttgtggagacaccagtcaaaatta<br>acctgttcaagttcctttcttcatggagtc<br>tttggggagccaactacatggattgttttg<br>agtccaatgaaaccatggggtttggcttca<br>tattgctgacaaaaaaaggaaaaagtacct<br>caataataaatacagaacttctcctttcaa<br>cctcttccatcacatcaacacctatgaaga<br>caatgggtttctgattgtggatctctgctg<br>ctggaaaggatttgagtttgtttataatta<br>cttatatttagccaatttacgtgagaactg<br>ggaagaggtgaaaaaaaatgccagaaaggc<br>tccccaacctgaagttaggagatatgtact<br>tcctttgaatattgacaaggctgacacagg<br>caagaatttagtcagctccccaatacaact<br>gccactgcaattctgtgcagtgacgagact<br>atctggctggagcctgaagttctcttttca |

TABLE 1-continued

| SEQ ID NO: | Non-coding Nucleotide sequences (stuffers) |
|---|---|
| | gggcctcgtcaagcatttgagtttcctcaa<br>atcaattaccagaagtattgtgggaaacct<br>tacacatatgcgtatggacttggcttgaat<br>cactttgttccagataggctctgtaagctg<br>aatgtcaaaactaaagaaacttgggtttgg<br>caagagcctgattcatacccatcagaaccc<br>atctttgtttctcacccagatgccttggaa<br>gaagatgatggtgtagttctgagtgtggtg<br>gtgagcccaggagcaggacaaaagcctgct<br>tatctcctgattctgaatgccaaggactta<br>agtgaagttgcccgggctgaagtggagatt<br>aacatccctgtcacctttcatggactgttc<br>aaaaaatcttga |
| 2 | cgagtttaattggtttatagaactcttcaa<br>acaaattaaaccaaaaatttcaatgccaag<br>aaagggtctttaaaacgaaattacagaagg<br>accaaatgataaggaagaaaaatgcagaga<br>taaaagtaatatcaattaggatcataagct<br>acttattatcaatgaaaagtaacagaaaca<br>tagatgctgcagaaatcttctgaggagtag<br>cttcaacgcctcagggtgtggacaatgtat<br>tcagcatagaggtccctgtaatggggatat<br>cagaatccagagttgctttaatgttacaaa<br>ctaaaaaagatgtaagagagtttggttctt<br>gataaagaaacagaggcttacattgagtac<br>tggatagcttcaaccgcagactcagatggc<br>agaaaatcattcactgcaacttccttgttc<br>tcgtttttcttgtctgtaagatattagagt<br>taaagggaaaaactaatacttgttgagaga<br>tcaatagagatgaataaggaggaacactga<br>agaaaaaggatacagtcttcgaagaaacga<br>cggatttcagagagacggtgaggaggaagt<br>tctttgatgtcagtgtagtgcttata |
| 3 | cgagtttaattggtttatagaactcttcaa<br>acaaattaaaccaaaaatttcaatgccaag<br>aaagggtctttaaaacgaaattacagaagg<br>accaaatgataaggaagaaaaatgcagaga<br>taaaagtaatatcaattaggatcataagct<br>acttattatcaatgaaaagtaacagaaaca<br>tagatgctgcagaaatcttctgaggagtag<br>cttcaacgcctcagggtgtggacaatgtat<br>tcagcatagaggtccctgtaatggggatat<br>cagaatccagagttgctttaatgttacaaa<br>ctaaaaaagatgtaagagagtttggttctt<br>gataaagaaacagaggcttacattgagtac<br>tggatagcttcaaccgcagactcagatggc<br>agaaaatcattcactgcaacttccttgttc<br>tcgtttttcttgtctgtaagatattagagt<br>taaagggaaaaactaatacttgttgagaga<br>tcaatagagatgaataaggaggaacactga<br>agaaaaaggatacagtcttcgaagaaacga<br>cggatttcagagagacggtgaggaggaagt<br>tctttgatgtcagtgtagtgcttatattca<br>ggatcatcaacacacactgcaatgatcttg<br>tcatctttttcaccctaaattacagcgcc<br>aaaaatacaagattggagtacaagaccatt<br>taaactgacctaaaggattagagtaagaga<br>aaaaaaaaacagagtcttttcattgatcaa<br>gtttaggttttacctggtcaatcataggca<br>ttaatccaatggctctggcacgcagaaaac<br>aacccggaagcacaggttcctacacaaaga<br>taataatatatatttgaaatacaaaaaatt<br>ggtgcaaatagtatagggataatatgagaa<br>agaaagaaagagtaatacctgcatgatgac<br>taagacatcaatggggtcattgtcttcaca<br>caatgtgcgaggaacaaaaccatagttgtg<br>agggtacacaactgatgagtagagaatacg<br>atcaacctgaatgagagatatcaaacttgt<br>tgagattgattttgctataagaaaaccatt<br>catataaaaaataaaa |
| 4 | cgagtttaattggtttatagaactcttcaa<br>acaaattaaaccaaaaatttcaatgccaag<br>aaagggtctttaaaacgaaattacagaagg |

TABLE 1-continued

| SEQ ID NO: | Non-coding Nucleotide sequences (stuffers) |
| --- | --- |
| | accaaatgataaggaagaaaaatgcagaga<br>taaaagtaatatcaattaggatcataagct<br>acttattatcaatgaaaagtaacagaaaca<br>tagatgctgcagaaatcttctgaggagtag<br>cttcaacgcctcagggtgtggacaatgtat<br>tcagcatagaggtccctgtaatggggatat<br>cagaatccagagttgctttaatgttacaaa<br>ctaaaaaagatgtaagagagtttggttctt<br>gataaagaaacagaggcttacattgagtac<br>tggatagcttcaaccgcagactcagatggc<br>agaaaatcattcactgcaacttccttgttc<br>tcgtttttcttgtctgtaagatattagagt<br>taaagggaaaaactaatacttgttgagaga<br>tcaatagagatgaataaggaggaacactga<br>agaaaaaggatacagtcttcgaagaaacga<br>cggatttcagagagacggtgaggaggaagt<br>tctttgatgtcagtgtagtgcttatattca<br>ggatcatcaacacacactgcaatgatcttg<br>tcatctttttcaccctaaaattacagcgcc<br>aaaaatacaagattggagtacaagaccatt<br>taaactgacctaaaggattagagtaagaga<br>aaaaaaaaacagagtcttttcattgatcaa<br>gtttaggttttacctggtcaatcataggca<br>ttaatccaatggctctggcacgcagaaaac<br>aacccggaagcacaggttcctacacaaaga<br>taataatatatatttgaaatacaaaaaatt<br>ggtgcaaatagtatagggataatatgagaa<br>agaaagaaagagtaatacctgcatgatgac<br>taagacatcaatggggtcattgtcttcaca<br>caatgtgcgaggaacaaaaccatagttgtg<br>agggtacacaactgatgagtagagaatacg<br>atcaacctgaatgagagatatcaaacttgt<br>tgagattgattttgctataagaaaaccatt<br>catataaaaaataaactttgttctcatcta<br>accttgatgagtcctgtctttttgtcaagc<br>tcgtatttgaccttgcttcctttagtgatc<br>tcaacaacctaataatcatccaaagataaa<br>atgattagagaatctaataacaacatactc<br>tgtttagaacaaagagtaggaaaaaactta<br>ccacattgaaaatctgtggagctccaggtc<br>ctagatagattatccagacttatgatttag<br>taacagaatacaaaagtatgaaatcaaaaa<br>gtagcatgtttagaatgatttatataccaa<br>tctcaagatcatgccatggatgagcagcta<br>cggatcttcttgacaaggatgagagaatcc<br>tctcgttaagacgaggagctggtcgctgca<br>gcctctggttatctttagtttcttcactca<br>tctgtcaaaatcagaacgtttcatcactca<br>ttgatattgactgaatctaacatcataacc<br>ctaattggcagagagagaatcaatcgaatc<br>aagaga |
| 5 | cgagtttaattggtttatagaactcttcaa<br>acaaattaaaccaaaaatttcaatgccaag<br>aaagggtctttaaaacgaaattacagaagg<br>accaaatgataaggaagaaaaatgcagaga<br>taaaagtaatatcaattaggatcataagct<br>acttattatcaatgaaaagtaacagaaaca<br>tagatgctgcagaaatcttctgaggagtag<br>cttcaacgcctcagggtgtggacaatgtat<br>tcagcatagaggtccctgtaatggggatat<br>cagaatccagagttgctttaatgttacaaa<br>ctaaaaaagatgtaagagagtttggttctt<br>gataaagaaacagaggcttacattgagtac<br>tggatagcttcaaccgcagactcagatggc<br>agaaaatcattcactgcaacttccttgttc<br>tcgtttttcttgtctgtaagatattagagt<br>taaagggaaaaactaatacttgttgagaga<br>tcaatagagatgaataaggaggaacactga<br>agaaaaaggatacagtcttcgaagaaacga<br>cggatttcagagagacggtgaggaggaagt<br>tctttgatgtcagtgtagtgcttatattca<br>ggatcatcaacacacactgcaatgatcttg<br>tcatctttttcaccctaaaattacagcgcc<br>aaaaatacaagattggagtacaagaccatt<br>taaactgacctaaaggattagagtaagaga<br>aaaaaaaaacagagtcttttcattgatcaa<br>gtttaggttttacctggtcaatcataggca<br>ttaatccaatggctctggcacgcagaaaac<br>aacccggaagcacaggttcctacacaaaga<br>taataatatatatttgaaatacaaaaaatt<br>ggtgcaaatagtatagggataatatgagaa<br>agaaagaaagagtaatacctgcatgatgac<br>taagacatcaatggggtcattgtcttcaca<br>caatgtgcgaggaacaaaaccatagttgtg<br>agggtacacaactgatgagtagagaatacg<br>atcaacctgaatgagagatatcaaacttgt<br>tgagattgattttgctataagaaaaccatt<br>catataaaaaataaactttgttctcatcta<br>accttgatgagtcctgtctttttgtcaagc<br>tcgtatttgaccttgcttcctttagtgatc<br>tcaacaacctaataatcatccaaagataaa<br>atgattagagaatctaataacaacatactc<br>tgtttagaacaaagagtaggaaaaaactta<br>ccacattgaaaatctgtggagctccaggtc<br>ctagatagattatccagacttatgatttag<br>taacagaatacaaaagtatgaaatcaaaaa<br>gtagcatgtttagaatgatttatataccaa<br>tctcaagatcatgccatggatgagcagcta<br>cggatcttcttgacaaggatgagagaatcc<br>tctcgttaagacgaggagctggtcgctgca<br>gcctctggttatctttagtttcttcactca<br>tctgtcaaaatcagaacgtttcatcactca<br>ttgatattgactgaatctaacatcataacc<br>ctaattggcagagagagaatcaatcgaatc<br>aagagtattaaatggaaaaagcgaatcaag<br>accccacaagggaaaacaatccttaaagca<br>gacttgagatcgatcatacccaaattatgg<br>attcatatattgttaacgtatcgattactg<br>aaaagatgtataccaaatctgttcactttt<br>tctctatagactcgatggatgattgagatt<br>tgaagcaacaaaatacccagaagattaaac<br>atggaaaagcatcaaactttgatgatctta<br>gaacgatgacaaaagaaaaaaaaacgtacc<br>tttggatcgaaacgaaacagccgattgttg<br>ttttctttatcgcaaggatgatgaagaaac<br>tttgggagagaaacaagtgaagcccgttgg<br>tctagcaagtgattgtaaaatgtatatatg<br>agtcaccaccgagatatacgga |

Expression Cassettes

One aspect relates to nucleic acids of the invention arranged in tandem with regulatory elements and one or more heterologous genes in a nucleic acid expression cassette. Regulatory elements, in general, function as recognition sites for transcription initiation or completion, coordination with cell-specific machinery to drive expression upon signalling, and to enhance expression of the heterologous gene, however transcription does not occur, or occurs infrequently or without deleterious effect from stuffer sequences. Stuffer sequences are considered “inert” or inactive, particularly with respect to recognition sites.

The recombinant expression cassettes may comprise a nucleic acid Also provided are vectors comprising an expression cassette comprising SEQ ID NO: 1, or one or more fragments of SEQ ID NO: 1 between 1-10, 10-20, 20-30, 30-40, 40-50, 50-60, 60-75, 75-100, 100-150, 150-200, 200-250, 250-300, 300-400, 400-500, 500-600, 600-750, 750-1,000, 1,000-1,500, or 1,500-1601 nucleotides in length. In some embodiments, the expression cassette comprises SEQ ID NO:5, or one or more fragments of SEQ ID NO:5 between 1-10, 10-20, 20-30, 30-40, 40-50, 50-60, 60-75, 75-100, 100-150, 150-200, 200-250, 250-300, 300-400, 400-500, 500-600, 600-750, 750-1,000, 1,000-1,500, or 1,500-2001 nucleotides in length. In some embodiments, the expression cassette comprises SEQ ID NO:1, SEQ ID NO:2, SEQ ID NO:3, SEQ ID NO:4, or SEQ ID NO:5, or a fragment thereof. In some embodiments, the expression cassette comprises one or more nucleic acid sequences SEQ ID NO:1. SEQ ID NO:2. SEQ ID NO:3, SEQ ID NO:4, or SEQ ID NO:5, or a fragment or fragments thereof. In some embodiments, the expression cassette further comprises a nucleic acid sequence encoding a heterologous gene. In some embodiments, the expression cassette further comprises one or more promoters, and a polyA downstream of the gene coding sequence. In some embodiments, the expression cassette directs expression of the transgene in target tissues, e.g. comprising the gene listed in, but not limited to, Tables 3A-3C. In some embodiments, the vectors comprise a transgene operably linked to SEQ ID NO:1. SEQ ID NO:2, SEQ ID NO:3, SEQ ID NO:4, or SEQ ID NO:5, or a fragment or fragments thereof. In some embodiments, the vectors comprise a heterologous gene operably linked to SEQ ID NO:1. SEQ ID NO:2, SEQ ID NO:3, SEQ ID NO:4, or SEQ ID NO:5, or a fragment or fragments thereof. In some embodiments, the vectors comprise a heterologous gene encoding a microRNA (miRNA), a short hairpin RNA (shRNA), an antibody, an antigen-binding fragment, a Fc-fusion protein, or an enzyme.

Provided are nucleic acid regulatory elements for enhancing gene expression human tissues comprising nucleic acid sequences SEQ ID NO:1, SEQ ID NO:2, SEQ ID NO:3, SEQ ID NO:4, SEQ ID NO:5 or SEQ ID NO:6.

In an aspect of the invention, exemplary regulatory elements and combinations of elements that may be utilized to design and generate nucleic acid expression cassettes, and are listed in, but not limited to those listed in Table 2.

TABLE 2

| Name | SEQ ID NO: | Nucleic Acid Sequence |
|---|---|---|
| CAG Promoter | 6 | GACATTGATTATTGACTAGTTATTAATAGTAATCAATTACGGGG<br>TCATTAGTTCATAGCCCATATATGGAGTTCCGCGTTACATAACT<br>TACGGTAAATGGCCCGCCTGGCTGACCGCCCAACGACCCCCGCC<br>CATTGACGTCAATAATGACGTATGTTCCCATAGTAACGCCAATA<br>GGGACTTTCCATTGACGTCAATGGGTGGAGTATTTACGGTAAAC<br>TGCCCACTTGGCAGTACATCAAGTGTATCATATGCCAAGTACGC<br>CCCCTATTGACGTCAATGACGGTAAATGGCCCGCCTGGCATTAT<br>GCCCAGTACATGACCTTATGGGACTTTCCTACTTGGCAGTACAT<br>CTACGTATTAGTCATCGCTATTACCATGGTCGAGGTGAGCCCCA<br>CGTTCTGCTTCACTCTCCCCATCTCCCCCCCCTCCCCACCCCCA<br>ATTTTGTATTTATTTATTTTTTAATTATTTTGTGCAGCGATGGG<br>GGCGGGGGGGGGGGGGGGGCGCGCGCCAGGCGGGGCGGGGCGGGG<br>GCGAGGGGCGGGGCGGGGCGAGGCGGAGAGGTGCGGCGGCAGCC<br>AATCAGAGCGGCGCGCTCCGAAAGTTTCCTTTTATGGCGAGGCG<br>GCGGCGGCGGCGGCCCTATAAAAAGCGAAGCGCGCGGCGGGCGG<br>GAGTCGCTGCGCGCTGCCTTCGCCCCGTGCCCCGCTCCGCCGCC<br>GCCTCGCGCCGCCCGCCCCGGCTCTGACTGACCGCGTTACTCCC<br>ACAGGTGAGCGGGCGGGACGGCCCTTCTCCTCCGGGCTGTAATT<br>AGCGCTTGGTTTAATGACGGCTTGTTTCTTTTCTGTGGCTGCGT<br>GAAAGCCTTGAGGGGCTCCGGGAGGGCCCTTTGTGCGGGGGGAG<br>CGGCTCGGGGGGTGCGTGCGTGTGTGTGTGCGTGGGGAGCGCCG<br>CGTGCGGCTCCGCGCTGCCCGGCGGCTGTGAGCGCTGCGGGCGC<br>GGCGCGGGGCTTTGTGCGCTCCGCAGTGTGCGCGAGGGGAGCGC<br>GGCCGGGGGCGGTGCCCCGCGGTGCGGGGGGGGCTGCGAGGGGA<br>ACAAAGGCTGCGTGCGGGGTGTGTGCGTGGGGGGGTGAGCAGGG<br>GGTGTGGGCGCGTCGGTCGGGCTGCAACCCCCCCTGCACCCCCC<br>TCCCCGAGTTGCTGAGCACGGCCCGGCTTCGGGTGCGGGGCTCC<br>GTACGGGGCGTGGCGCGGGGCTCGCCGTGCCGGGGGGGGGGTGG<br>CGGCAGGTGGGGGTGCCGGGCGGGGGGGGCCGCCTCGGGCCCGG<br>GGAGGGCTCGGGGGAGGGGCGCGGCGGCCCCCGGAGCGCCGGCG<br>GCTGTCGAGGCGCGGCGAGCCGCAGCCATTGCCTTTTATGGTAA<br>TCGTGCGAGAGGGCGCAGGGACTTCCTTTGTCCCAAATCTGTGC<br>GGAGCCGAAATCTGGGAGGCGCCGCCGCACCCCCTCTAGCGGGC<br>GCGGGGCGAAGCGGTGCGGCGCCGGCAGGAAGGAAATGGGCGGG<br>GAGGGCCTTCGTGCGTCGCCGCGCCGCCGTCCCCTTCTCCCTCT<br>CCAGCCTCGGGGCTGTCCGCGGGGGGACGGCTGCCTTCGGGGGG<br>GACGGGGCAGGGCGGGGTTCGGCTTCTGGCGTGTGACCGGCGGC<br>TCTAGAGCCTCTGCTAACCATGTTCATGCCTTCTTCTTTTTCCT<br>ACAG |
| CK Promoter | 7 | CCCTGCATGCGAAGATCTTCGAACAAGGCTGTGGGGGACTGAGG<br>GCAGGCTGTAACAGGCTTGGGGGCCAGGGCTTATACGTGCCTGG<br>GACTCCCAAAGTATTACTGTTCCATGTTCCCGGCGAAGGGCCAG<br>CTGTCCCCCGCCAGCTAGACTCAGCACTTAGTTTAGGAACCAGT<br>GAGCAAGTCAGCCCTTGGGGCAGCCCATACAAGGCCATGGGGCT<br>GGGCAAGCTGCACGCCTGGGTCCGGGGTGGGCACGGTGCCCGGG<br>CAACGAGCTGAAAGCTCATCTGCTCTCAGGGGCCCCTCCCTGGG<br>GACAGCCCCTCCTGGCTAGTCACACCCTGTAGGCTCCTCTATAT<br>AACCCAGGGGCACAGGGGCTGCCCTCATTCTACCACCACCTCCA<br>CAGCACAGACAGACACTCAGGAGCCAGCCAGCGTCGA |
| SPc5-12 | 8 | GGCCGTCCGCCCTCGGCACCATCCTCACGACACCCAAATATGGC<br>GACGGGTGAGGAATGGTGGGGAGTTATTTTTAGAGCGGTGAGGA<br>AGGTGGGCAGGCAGCAGGTGTTGGCGCTCTAAAAATAACTCCCG<br>GGAGTTATTTTTAGAGCGGAGGAATGGTGGACACCCAAATATGG |

TABLE 2-continued

| Name | SEQ ID NO: | Nucleic Acid Sequence |
|---|---|---|
| | | CGACGGTTCCTCACCCGTCGCCATATTTGGGTGTCCGCCCTCGG CCGGGGCCGCATTCCTGGGGGCCGGGCGGTGCTCCCGCCCGCCT CGATAAAAGGCTCCGGGGCCGGCGGCGGCCCACGAGCTACCCGG AGGAGCGGGAGGCGCCAAGC |
| minSPc5-12 | 9 | GAATGGTGGACACCCAAATATGGCGACGGTTCCTCACCCGTCGC CATATTTGGGTGTCCGCCCTCGGCCGGGGCCGCATTCCTGGGGG CCGGGCGGTGCTCCCGCCCGCCTCGATAAAAGGCTCCGGGGCCG GCGGCGGCCCACGAGCTACCCGGAGGAGCGGGAGGCGCCAAG |
| CK8 | 10 | CCACTACGGGTTTAGGCTGCCCATGTAAGGAGGCAAGGCCTGGG GACACCCGAGATGCCTGGTTATAATTAACCCAGACATGTGGCTG CCCCCCCCCCCCCCAACACCTGCTGCCTCTAAAAATAACCCTGT CCCTGGTGGATCCCACTACGGGTTTAGGCTGCCCATGTAAGGAG GCAAGGCCTGGGGACACCCGAGATGCCTGGTTATAATTAACCCA GACATGTGGCTGCCCCCCCCCCCCCCAACACCTGCTGCCTCTAA AAATAACCCTGTCCCTGGTGGATCCCACTACGGGTTTAGGCTGC CCATGTAAGGAGGCAAGGCCTGGGGACACCCGAGATGCCTGGTT ATAATTAACCCAGACATGTGGCTGCCCCCCCCCCCCCCAACACC TGCTGCCTCTAAAAATAACCCTGTCCCTGGTGGATCCCCTGCAT GCGAAGATCTTCGAACAAGGCTGTGGGGGACTGAGGGCAGGCTG TAACAGGCTTGGGGGCCAGGGCTTATACGTGCCTGGGACTCCCA AAGTATTACTGTTCCATGTTCCCGGCGAAGGGCCAGCTGTCCCC CGCCAGCTAGACTCAGCACTTAGTTTAGGAACCAGTGAGCAAGT CAGCCCTTGGGGCAGCCCATACAAGGCCATGGGGCTGGGCAAGC TGCACGCCTGGGTCCGGGGTGGGCACGGTGCCCGGGCAACGAGC TGAAAGCTCATCTGCTCTCAGGGGCCCCTCCCTGGGGACAGCCC CTCCTGGCTAGTCACACCCTGTAGGCTCCTCTATATAACCCAGG GGCACAGGGGCTGCCCTCATTCTACCACCACCTCCACAGCACAG ACAGACACTCAGGAGCCAGCCAGCGTCGA |
| mU1a | 11 | ATGGAGGCGGTACTATGTAGATGAGAATTCAGGAGCAAACTGGG AAAAGCAACTGCTTCCAAATATTTGTGATTTTTACAGTGTAGTT TTGGAAAAACTCTTAGCCTACCAATTCTTCTAAGTGTTTTAAAA TGTGGGAGCCAGTACACATGAAGTTATAGAGTGTTTTAATGAGG CTTAAATATTTACCGTAACTATGAAATGCTACGCATATCATGCT GTTCAGGCTCCGTGGCCACGCAACTCATACT |
| EF-1α | 12 | GGGCAGAGCGCACATCGCCCACAGTCCCCGAGAAGTTGGGGGGA GGGGTCGGCAATTGAACGGGTGCCTAGAGAAGGTGGCGCGGGGT AAACTGGGAAAGTGATGTCGTGTACTGGCTCCGCCTTTTTCCCG AGGGTGGGGGAGAACCGTATATAAGTGCAGTAGTCGCCGTGAAC GTTCTTTTTCGCAACGGGTTTGCCGCCAGAACACAG |
| Human desmin | 13 | CTGCAGACATGCTTGCTGCCTGCCCTGGCGTGCCCTGGCGAGGCTT GCCGTCACAGGACCCCCGCTGGCTGACTCAGGGGCGCAGGCTCTTG CGGGGGAGCTGGCCTCCCCGCCCCCACGGCCACGGGCCCTTTCCTGG CAGGACAGCGGGATCTTGCAGCTGTCAGGGGAGGGGATGACGGGGG ACTGATGTCAGGAGGGGATACAAATAGTGCCGAACAAGGACCGGAT TAGATCTACC |
| MHCK7 | 14 | AAGCTTGCAT GTCTAAGCTA GACCCTTCAG ATTAAAAATA ACTGAGGTAA GGGCCTGGGT AGGGGAGGTG GTGTGAGACG CTCCTGTCTC TCCTCTATCT GCCCATCGGC CCTTTGGGGA GGAGGAATGT GCCCAAGGAC TAAAAAAAGG CCATGGAGCC AGAGGGGCGA GGGCAACAGA CCTTTCATGG GCAAACCTTG GGGCCCTGCT GTCTAGCATG CCCCACTACG GGTCTAGGCT GCCCATGTAA GGAGGCAAGG CCTGGGGACA CCCGAGATGC CTGGTTATAA TTAACCCAGA CATGTGGCTG CCCCCCCCCC CCCAACACCT GCTGCCTCTA AAAATAACCC TGTCCCTGGT GGATCCCCTG CATGCGAAGA TCTTCGAACA AGGCTGTGGG GGACTGAGGG CAGGCTGTAA CAGGCTTGGG GGCCAGGGCT TATACGTGCC TGGGACTCCC AAAGTATTAC TGTTCCATGT TCCCGGCGAA GGGCCAGCTG TCCCCCGCCA GCTAGACTCA GCACTTAGTT TAGGAACCAG TGAGCAAGTC AGCCCTTGGG GCAGCCCATA CAAGGCCATG GGGCTGGGCA AGCTGCACGC CTGGGTCCGG GGTGGGCACG GTGCCCGGGC AACGAGCTGA AAGCTCATCT GCTCTCAGGG GCCCCTCCCT GGGGACAGCC CCTCCTGGCT AGTCACACCC TGTAGGCTCC TCTATATAAC CCAGGGGCAC AGGGGCTGCC CTCATTCTAC CACCACCTCC ACAGCACAGA CAGACACTCA GGAGCAGCCA GC |
| hSyn-1 promoter | 15 | AGTGCAAGTGGGTTTTAGGACCAGGATGAGGCGGGGTGGGGGTG CCTACCTGACGACCGACCCCGACCCACTGGACAAGCACCCAACC CCCATTCCCCAAATTGCGCATCCCCTATCAGAGAGGGGGAGGGG AAACAGGATGCGGCGAGGCGCGTGCGCACTGCCAGCTTCAGCAC |

TABLE 2-continued

| Name | SEQ ID NO: | Nucleic Acid Sequence |
|---|---|---|
| | | CGCGGACAGTGCCTTCGCCCCCGCCTGGCGGCGCGCGCCACCGC<br>CGCCTCAGCACTGAAGGCGCGCTGACGTCACTCGCCGGTCCCCC<br>GCAAACTCCCCTTCCCGGCCACCTTGGTCGCGTCCGCGCCGCCG<br>CCGGCCCAGCCGGACCGCACCACGCGAGGCGCGAGATAGGGGGG<br>CACGGGCGCGACCATCTGCGCTGCGGCGCCGGCGACTCAGCGCT<br>GCCTCAGTCTGCGGTGGGCAGCGGAGGAGTCGTGTCGTGCCTGA<br>GAGCGCAG |
| Mecp2 promoter | 16 | AGCTGAATGGGGTCCGCCTCTTTTCCCTGCCTAAACAGACAGGA<br>ACTCCTGCCAATTGAGGGCGTCACCGCTAAGGCTCCGCCCCAGC<br>CTGGGCTCCACAACCAATGAAGGGTAATCTCGACAAAGAGCAAG<br>GGGTGGGGCGCGGGCGCGCAGGTGCAGCAGCACACAGGCTGGTC<br>GGGAGGGCGGGGCGCGACGTCTGCCGTGCGGGGTCCCGGCATCG<br>GTTGCGCGC |
| hGFAP promoter | 17 | GTCTGCAAGCAGACCTGGCAGCATTGGGCTGGCCGCCCCCCAGG<br>GCCTCCTCTTCATGCCCAGTGAATGACTCACCTTGGCACAGACA<br>CAATGTTCGGGGTGGGCACAGTGCCTGCTTCCCGCCGCACCCCA<br>GCCCCCCTCAAATGCCTTCCGAGAAGCCCATTGAGTAGGGGGCT<br>TGCATTGCACCCCAGCCTGACAGCCTGGCATCTTGGGATAAAAG<br>CAGCACAGCCCCCTAGGGGCTGCCCTTGCTGTGTGGCGCCACCG<br>GCGGTGGAGAACAAGGCTCTATTCAGCCTGTGCCCAGGAAAGGG<br>GATCAGGGGATGCCCAGGCATGGACAGTGGGTGGCAGGGGGGGA<br>GAGGAGGGCTGTCTGCTTCCCAGAAGTCCAAGGACACAAATGGG<br>TGAGGGGACTGGGCAGGGTTCTGACCCTGTGGGACCAGAGTGGA<br>GGGCGTAGATGGACCTGAAGTCTCCAGGGACAACAGGGCCCAGG<br>TCTCAGGCTCCTAGTTGGGCCCAGTGGCTCCAGCGTTTCCAAAC<br>CCATCCATCCCCAGAGGTTCTTCCCATCTCTCCAGGCTGATGTG<br>TGGGAACTCGAGGAAATAAATCTCCAGTGGGAGACGGAGGGGTG<br>GCCAGGGAAACGGGGCGCTGCAGGAATAAAGACGAGCCAGCACA<br>GCCAGCTCATGCGTAACGGCTTTGTGGAGCTGTCAAGGCCTGGT<br>CTCTGGGAGAGAGGCACAGGGAGGCCAGACAAGGAAGGGGTGAC<br>CTGGAGGGACAGATCCAGGGGCTAAAGTCCTGATAAGGCAAGAG<br>AGTGCCGGCCCCCTCTTGCCCTATCAGGACCTCCACTGCCACAT<br>AGAGGCCATGATTGACCCTTAGACAAAGGGCTGGTGTCCAATCC<br>CAGCCCCCAGCCCCAGAACTCCAGGGAATGAATGGGCAGAGAGC<br>AGGAATGTGGGACATCTGTGTTCAAGGGAAGGACTCCAGGAGTC<br>TGCTGGGAATGAGGCCTAGTAGGAAATGAGGTGGCCCTTGAGGG<br>TACAGAACAGGTTCATTCTTCGCCAAATTCCCAGCACCTTGCAG<br>GCACTTACAGCTGAGTGAGATAATGCCTGGGTTATGAAATCAAA<br>AAGTTGGAAAGCAGGTCAGAGGTCATCTGGTACAGCCCTTCCTT<br>CCCTTTTTTTTTTTTTTTTTTTTTTGTGAGACAAGGTCTCTCTC<br>TGTTGCCCAGGCTGGAGTGGCGCAAACACAGCTCACTGCAGCCT<br>CAACCTACTGGGCTCAAGCAATCCTCCAGCCTCAGCCTCCCAAA<br>GTGCTGGGATTACAAGCATGAGCCACCCCACTCAGCCCTTTCCT<br>TCCTTTTTAATTGATGCATAATAATTGTAAGTATTCATCATGGT<br>CCAACCAACCCTTTCTTGACCCACCTTCCTAGAGAGAGGGTCCT<br>CTTGATTCAGCGGTCAGGGCCCCAGACCCATGGTCTGGCTCCAG<br>GTACCACCTGCCTCATGCAGGAGTTGGCGTGCCCAGGAAGCTCT<br>GCCTCTGGGCACAGTGACCTCAGTGGGGTGAGGGGAGCTCTCCC<br>CATAGCTGGGCTGCGGCCCAACCCCACCCCCTCAGGCTATGCCA<br>GGGGGTGTTGCCAGGGGCACCCGGGCATCGCCAGTCTAGCCCAC<br>TCCTTCATAAAGCCCTCGCATCCCAGGAGCGAGCAGAGCCAGAG<br>CAT |
| NeuN | 18 | GAGGAGGAGGAGAGAGACCGGGAGGGCGCCCGGGAGGCAGGGCG<br>CGCGCACACTCCGAGG |
| CamKII | 19 | GATGCTGACGAAGGCTCGCGAGGCTGTGAGCAGCCACAGTGCCC<br>TGCTCAGAAGCCCCGG |
| LSPX1 Promoter | 20 | AGGTTAATTTTTAAAAAGCAGTCAAAAGTCCAAGTGGCCCTTGG<br>CAGCATTTACTCTCTCTGTTTGCTCTGGTTAATAATCTCAGGAG<br>CACAAACATTCCAGATCCAGGTTAATTTTTAAAAAGCAGTCAAA |
| | 21 | AGTCCAAGTGGCCCTTGGCAGCATTTACTCTCTCTGTTTGCTCT<br>GGTTAATAATCTCAGGAGCACAAACATTCCAGATCCGGCGCGCC<br>AGGGCTGGAAGCTACCTTTGTCTAGAAGGCTCAGAGGCACACAG<br>GAGTTTCTGGGCTCACCCTGCCCCCTTCCAACCCCTCAGTTCCC<br>ATCCTCCAGCAGCTGTTTGTGTGCTGCCTCTGAAGTCCACACTG<br>AACAAACTTCAGCCTACTCATGTCCCTAAAATGGGCAAACATTG<br>CAAGCAGCAAACAGCAAACACACAGCCCTCCCTGCCTGCTGACC<br>TTGGAGCTGGGGCAGAGGTCAGAGACCTCTCTGGGCCCATGCCA<br>CCTCCAACATCCACTCGACCCCTTGGAATTTCGGTGGAGAGGAG<br>CAGAGGTTGTCCTGGCGTGGTTTAGGTAGTGTGAGAGGGGTACC<br>CGGGGATCTTGCTACCAGTGGAACAGCCACTAAGGATTCTGCAG<br>TGAGAGCAGAGGGCCAGCTAAGTGGTACTCTCCCAGAGACTGTC |

TABLE 2-continued

| Name | SEQ ID NO: | Nucleic Acid Sequence |
|---|---|---|
| | | TGACTCACGCCACCCCCTCCACCTTGGACACAGGACGCTGTGGT<br>TTCTGAGCCAGGTACAATGACTCCTTTCGGTAAGTGCAGTGGAA<br>GCTGTACACTGCCCAGGCAAAGCGTCCGGGCAGCGTAGGCGGGC<br>GACTCAGATCCCAGCCAGTGGACTTAGCCCCTGTTTGCTCCTCC<br>GATAACTGGGGTGACCTTGGTTAATATTCACCAGCAGCCTCCCC<br>CGTTGCCCCTCTGGATCCACTGCTTAAATACGGACGAGGACAGG<br>GCCCTGTCTCCTCAGCTTCAGGCACCACCACTGACCTGGGACAG<br>T |
| LSPX2 | | AGGCTCAGAGGCACACAGGAGTTTCTGGGCTCACCCTGCCCCCT<br>TCCAACCCCTCAGTTCCCATCCTCCAGCAGCTGTTTGTGTGCTG<br>CCTCTGAAGTCCACACTGAACAAACTTCAGCCTACTCATGTCCC<br>TAAAATGGGCAAACATTGCAAGCAGCAAACAGCAAACACACAGC<br>CCTCCCTGCCTGCTGACCTTGGAGCTGGGGCAGAGGTCAGAGAC<br>CTCTCTGGGCCCATGCCACCTCCAACATCCACTCGACCCCTTGG<br>AATTTCGGTGGAGAGGAGCAGAGGTTGTCCTGGCGTGGTTTAGG<br>TAGTGTGAGAGGGTCTAGAAGGCTCAGAGGCACACAGGAGTTTC<br>TGGGCTCACCCTGCCCCCTTCCAACCCCTCAGTTCCCATCCTCC<br>AGCAGCTGTTTGTGTGCTGCCTCTGAAGTCCACACTGAACAAAC<br>TTCAGCCTACTCATGTCCCTAAAATGGGCAAACATTGCAAGCAG<br>CAAACAGCAAACACACAGCCCTCCCTGCCTGCTGACCTTGGAGC<br>TGGGGCAGAGGTCAGAGACCTCTCTGGGCCCATGCCACCTCCAA<br>CATCCACTCGACCCCTTGGAATTTCGGTGGAGAGGAGCAGAGGT<br>TGTCCTGGCGTGGTTTAGGTAGTGTGAGAGGGGTACCCGGGGAT<br>CTTGCTACCAGTGGAACAGCCACTAAGGATTCTGCAGTGAGAGC<br>AGAGGGCCAGCTAAGTGGTACTCTCCCAGAGACTGTCTGACTCA<br>CGCCACCCCCTCCACCTTGGACACAGGACGCTGTGGTTTCTGAG<br>CCAGGTACAATGACTCCTTTCGGTAAGTGCAGTGGAAGCTGTAC<br>ACTGCCCAGGCAAAGCGTCCGGGCAGCGTAGGCGGGCGACTCAG<br>ATCCCAGCCAGTGGACTTAGCCCCTGTTTGCTCCTCCGATAACT<br>GGGGTGACCTTGGTTAATATTCACCAGCAGCCTCCCCCGTTGCC<br>CCTCTGGATCCACTGCTTAAATACGGACGAGGACAGGGCCCTGT<br>CTCCTCAGCTTCAGGCACCACCACTGACCTGGGACAGT |
| LTP1 | 22 | AGGTTAATTTTTAAAAAGCAGTCAAAAGTCCAAGTGGCCCTTGG<br>CAGCATTTACTCTCTCTGTTTGCTCTGGTTAATAATCTCAGGAG<br>CACAAACATTCCAGATCCAGGTTAATTTTTAAAAAGCAGTCAAA<br>AGTCCAAGTGGCCCTTGGCAGCATTTACTCTCTCTGTTTGCTCT<br>GGTTAATAATCTCAGGAGCACAAACATTCCAGATCCGGCGCGCC<br>AGGGCTGGAAGCTACCTTTGACATCATTTCCTCTGCGAATGCAT<br>GTATAATTTCTACAGAACCTATTAGAAAGGATCACCCAGCCTCT<br>GCTTTTGTACAACTTTCCCTTAAAAAACTGCCAATTCCACTGCT<br>GTTTGGCCCAATAGTGAGAACTTTTTCCTGCTGCCTCTTGGTGC<br>TTTTGCCTATGGCCCCTATTCTGCCTGCTGAAGACACTCTTGCC<br>AGCATGGACTTAAACCCCTCCAGCTCTGACAATCCTCTTTCTCT<br>TTTGTTTTACATGAAGGGTCTGGCAGCCAAAGCAATCACTCAAA<br>GTTCAAACCTTATCATTTTTTGCTTTGTTCCTCTTGGCCTTGGT<br>TTTGTACATCAGCTTTGAAAATACCATCCCAGGGTTAATGCTGG<br>GGTTAATTTATAACTAAGAGTGCTCTAGTTTTGCAATACAGGAC<br>ATGCTATAAAAATGGAAAGATGTTGCTTTCTGAGAGGATCTTGC<br>TACCAGTGGAACAGCCACTAAGGATTCTGCAGTGAGAGCAGAGG<br>GCCAGCTAAGTGGTACTCTCCCAGAGACTGTCTGACTCACGCCA<br>CCCCCTCCACCTTGGACACAGGACGCTGTGGTTTCTGAGCCAGG<br>TACAGTGACTCCTTTCGGTAAGTGCAGTGGAAGCTGTACACTGC<br>CCAGGCAAAGCGTCCGGGCAGCGTAGGCGGGCGACTCAGATCCC<br>AGCCAGTGGACTTAGCCCCTGTTTGCTCCTCCGATAACTGGGGT<br>GACCTTGGTTAATATTCACCAGCAGCCTCCCCCGTTGCCCCTCT<br>GGATCCACTGCTTAAATACGGACGAGGACAGGGCCCTGTCTCCT<br>CAGCTTCAGGCACCACCACTGACCTGGGACAGT |
| LTP2 | 23 | AGGCTCAGAGGCACACAGGAGTTTCTGGGCTCACCCTGCCCCCT<br>TCCAACCCCTCAGTTCCCATCCTCCAGCAGCTGTTTGTGTGCTG<br>CCTCTGAAGTCCACACTGAACAAACTTCAGCCTACTCATGTCCC<br>TAAAATGGGCAAACATTGCAAGCAGCAAACAGCAAACACACAGC<br>CCTCCCTGCCTGCTGACCTTGGAGCTGGGGCAGAGGTCAGAGAC<br>CTCTCTGGGCCCATGCCACCTCCAACATCCACTCGACCCCTTGG<br>AATTTCGGTGGAGAGGAGCAGAGGTTGTCCTGGCGTGGTTTAGG<br>TAGTGTGAGAGGGTCTAGAGCCCTTAAGCTAGCAGGTTAATTTT<br>TAAAAAGCAGTCAAAAGTCCAAGTGGCCCTTGGCAGCATTTACT<br>CTCTCTGTTTGCTCTGGTTAATAATCTCAGGAGCACAAACATTC<br>CAGATCCAGGTTAATTTTTAAAAAGCAGTCAAAAGTCCAAGTGG<br>CCCTTGGCAGCATTTACTCTCTCTGTTTGCTCTGGTTAATAATC<br>TCAGGAGCACAAACATTCCAGATCCGGCGCGCCAGGGCTGGAAG<br>CTACCTTTGACATCATTTCCTCTGCGAATGCATGTATAATTTCT<br>ACAGAACCTATTAGAAAGGATCACCCAGCCTCTGCTTTTGTACA<br>ACTTTCCCTTAAAAAACTGCCAATTCCACTGCTGTTTGGCCCAA |

TABLE 2-continued

| Name | SEQ ID NO: | Nucleic Acid Sequence |
|---|---|---|
| | | TAGTGAGAACTTTTTCCTGCTGCCTCTTGGTGCTTTTGCCTATG<br>GCCCCTATTCTGCCTGCTGAAGACACTCTTGCCAGCATGGACTT<br>AAACCCCTCCAGCTCTGACAATCCTCTTTCTCTTTTGTTTTACA<br>TGAAGGGTCTGGCAGCCAAAGCAATCACTCAAAGTTCAAACCTT<br>ATCATTTTTTGCTTTGTTCCTCTTGGCCTTGGTTTTGTACATCA<br>GCTTTGAAAATACCATCCCAGGGTTAATGCTGGGGTTAATTTAT<br>AACTAAGAGTGCTCTAGTTTTGCAATACAGGACATGCTATAAAA<br>ATGGAAAGATGTTGCTTTCTGAGAGGATCTTGCTACCAGTGGAA<br>CAGCCACTAAGGATTCTGCAGTGAGAGCAGAGGGCCAGCTAAGT<br>GGTACTCTCCCAGAGACTGTCTGACTCACGCCACCCCCCTCCACC<br>TTGGACACAGGACGCTGTGGTTTCTGAGCCAGGTACAGTGACTC<br>CTTTCGGTAAGTGCAGTGGAAGCTGTACACTGCCCAGGCAAAGC<br>GTCCGGGCAGCGTAGGCGGGCGACTCAGATCCCAGCCAGTGGAC<br>TTAGCCCCTGTTTGCTCCTCCGATAACTGGGGTGACCTTGGTTA<br>ATATTCACCAGCAGCCTCCCCCGTTGCCCCTCTGGATCCACTGC<br>TTAAATACGGACGAGGACAGGGCCCTGTCTCCTCAGCTTCAGGC<br>ACCACCACTGACCTGGGACAGT |
| LTP3 | 24 | AGGTTAATTTTTAAAAAGCAGTCAAAAGTCCAAGTGGCCCTTGG<br>CAGCATTTACTCTCTCTGTTTGCTCTGGTTAATAATCTCAGGAG<br>CACAAACATTCCAGATCCAGGTTAATTTTTAAAAAGCAGTCAAA<br>AGTCCAAGTGGCCCTTGGCAGCATTTACTCTCTCTGTTTGCTCT<br>GGTTAATAATCTCAGGAGCACAAACATTCCAGATCCGGCGCGCC<br>AGGGCTGGAAGCTACCTTTGACATCATTTCCTCTGCGAATGCAT<br>GTATAATTTCTACAGAACCTATTAGAAAGGATCACCCAGCCTCT<br>GCTTTTGTACAACTTTCCCTTAAAAAACTGCCAATTCCACTGCT<br>GTTTGGCCCAATAGTGAGAACTTTTTCCTGCTGCCTCTTGGTGC<br>TTTTGCCTATGGCCCCTATTCTGCCTGCTGAAGACACTCTTGCC<br>AGCATGGACTTAAACCCCTCCAGCTCTGACAATCCTCTTTCTCT<br>TTTGTTTTACATGAAGGGTCTGGCAGCCAAAGCAATCACTCAAA<br>GTTCAAACCTTATCATTTTTTGCTTTGTTCCTCTTGGCCTTGGT<br>TTTGTACATCAGCTTTGAAAATACCATCCCAGGGTTAATGCTGG<br>GGTTAATTTATAACTAAGAGTGCTCTAGTTTTGCAATACAGGAC<br>ATGCTATAAAAATGGAAAGATGTTGCTTTCTGAGAGGATCTTGC<br>TACCAGTGGAACAGCCACTAAGGATTCTGCAGTGAGAGCAGAGG<br>GCCAGCTAAGTGGTACTCTCCCAGAGACTGTCTGACTCACGCCA<br>CCCCCTCCACCTTGGACACAGGACGCTGTGGTTTCTGAGCCAGG<br>TACAGTGACTCCTTTCGGTAAGTGCAGTGGAAGCTGTACACTGC<br>CCAGGCAAAGCGTCCGGGCAGCGTAGGCGGGCGACTCAGATCCC<br>AGCCAGTGGACTTAGCCCCTGTTTGCTCCTCCGATAACTGGGGT<br>GACCTTGGTTAATATTCACCAGCAGCCTCCCCCGTTGCCCCTCT<br>GGATCCACTGCTTAAATACGGACGAGGACAGGGCCCTGTCTCCT<br>CAGCTTCAGGCACCACCACTGACCTGGGACAGTAAAACAGGTAA<br>GTCCGCTGTTTGTGTGCTGCCTCTGAAGTCCACACTGAACAAAC<br>TTCAGCCTACTCATGTCCCTAAAATGGGCAAACATTGCAAGCAG<br>CAAACAGCAAACACACAGCCCTCCCTGCCTGCTGACCTTGGAGC<br>TGGGGCAGAGGTCAGAGACCTCTCTGGCCTCTACTAACCATGTT<br>CATGTTTTCTTTTTTTTTCTACAGGTCCTGGGTGACGAACAG |
| LMTP6 | 25 | AGGCTCAGAGGCACACAGGAGTTTCTGGGCTCACCCTGCCCCCT<br>TCCAACCCCTCAGTTCCCATCCTCCAGCAGCTGTTTGTGTGCTG<br>CCTCTGAAGTCCACACTGAACAAACTTCAGCCTACTCATGTCCC<br>TAAAATGGGCAAACATTGCAAGCAGCAAACAGCAAACACACAGC<br>CCTCCCTGCCTGCTGACCTTGGAGCTGGGGCAGAGGTCAGAGAC<br>CTCTCTGGGCCCATGCCACCTCCAACATCCACTCGACCCCTTGG<br>AATTTCGGTGGAGAGGAGCAGAGGTTGTCCTGGCGTGGTTTAGG<br>TAGTGTGAGAGGGCCACTACGGGTTTAGGCTGCCCATGTAAGGA<br>GGCAAGGCCTGGGGACACCCGAGATGCCTGGTTATAATTAACCC<br>AGACATGTGGCTGCCCCCCCCCCCCCCAACACCTGCTGCCTCTA<br>AAAATAACCCTGTCCCTGGTGGATCCCACTACGGGTTTAGGCTG<br>CCCATGTAAGGAGGCAAGGCCTGGGGACACCCGAGATGCCTGGT<br>TATAATTAACCCAGACATGTGGCTGCCCCCCCCCCCCCCAACAC<br>CTGCTGCCTCTAAAAATAACCCTGTCCCTGGTGGATCCCACTAC<br>GGGTTTAGGCTGCCCATGTAAGGAGGCAAGGCCTGGGGACACCC<br>GAGATGCCTGGTTATAATTAACCCAGACATGTGGCTGCCCCCCC<br>CCCCCCCAACACCTGCTGCCTCTAAAAATAACCCTGTCCCTGGT<br>GGATCCCCTGCATGCGAAGATCTTCGAACAAGGCTGTGGGGGAC<br>TGAGGGCAGGCTGTAACAGGCTTGGGGGCCAGGGCTTATACGTG<br>CCTGGGACTCCCAAAGTATTACTGTTCCATGTTCCCGGCGAAGG<br>GCCAGCTGTCCCCCGCCAGCTAGACTCAGCACTTAGTTTAGGAA<br>CCAGTGAGCAAGTCAGCCCTTGGGGCAGCCCATACAAGGCCATG<br>GGGCTGGGCAAGCTGCACGCCTGGGTCCGGGTGGGGCACGGTGC<br>CCGGGCAACGAGCTGAAAGCTCATCTGCTCTCAGGGGCCCCTCC<br>CTGGGGACAGCCCCTCCTGGCTAGTCACACCCTGTAGGCTCCTC<br>TATATAACCCAGGGGCACAGGGGCTGCCCTCATTCTACCACCAC<br>CTCCACAGCACAGACAGACACTCAGGAGCCAGCCAGCGTCGAGA |

TABLE 2-continued

| Name | SEQ ID NO: | Nucleic Acid Sequence |
|---|---|---|
| | | TCTTGCTACCAGTGGAACAGCCACTAAGGATTCTGCAGTGAGAG<br>CAGAGGGCCAGCTAAGTGGTACTCTCCCAGAGACTGTCTGACTC<br>ACGCCACCCCCTCCACCTTGGACACAGGACGCTGTGGTTTCTGA<br>GCCAGGTACAGTGACTCCTTTCGGTAAGTGCAGTGGAAGCTGTA<br>CACTGCCCAGGCAAAGCGTCCGGGCAGCGTAGGCGGGCGACTCA<br>GATCCCAGCCAGTGGACTTAGCCCCTGTTTGCTCCTCCGATAAC<br>TGGGGTGACCTTGGTTAATATTCACCAGCAGCCTCCCCCGTTGC<br>CCCTCTGGATCCACTGCTTAAATACGGACGAGGACAGGGCCCTG<br>TCTCCTCAGCTTCAGGCACCACCACTGACCTGGGACAGT |
| Alpha-Mic/Bik Enhancer (Mic/BikE) | 26 | AGGTTAATTTTTAAAAAGCAGTCAAAAGTCCAAGTGGCCCTTGG<br>CAGCATTTACTCTCTCTGTTTGCTCTGGTTAATAATCTCAGGAG<br>CACAAACATTCC |
| Tandem (2) Mic/Bik Enhancers | 27 | AGGTTAATTTTTAAAAAGCAGTCAAAAGTCCAAGTGGCCCTTGG<br>CAGCATTTACTCTCTCTGTTTGCTCTGGTTAATAATCTCAGGAG<br>CACAAACATTCC |
| ApopE Hepatic Control Region containing ApoE Enhancer | 28 | AGGCTCAGAGGCACACAGGAGTTTCTGGGCTCACCCTGCCCCCT<br>TCCAACCCCTCAGTTCCCATCCTCCAGCAGCTGTTTGTGTGCTG<br>CCTCTGAAGTCCACACTGAACAAACTTCAGCCTACTCATGTCCC<br>TAAAATGGGCAAACATTGCAAGCAGCAAACAGCAAACACACAGC<br>CCTCCCTGCCTGCTGACCTTGGAGCTGGGGCAGAGGTCAGAGAC<br>CTCTCTGGGCCCATGCCACCTCCAACATCCACTCGACCCCTTGG<br>AATTTCGGTGGAGAGGAGCAGAGGTTGTCCTGGCGTGGTTTAGG<br>TAGTGTGAGAGGG |
| Tandem (2) ApoE Enhancers | 29 | AGGCTCAGAGGCACACAGGAGTTTCTGGGCTCACCCTGCCCCCT<br>TCCAACCCCTCAGTTCCCATCCTCCAGCAGCTGTTTGTGTGCTG<br>CCTCTGAAGTCCACACTGAACAAACTTCAGCCTACTCATGTCCC<br>TAAAATGGGCAAACATTGCAAGCAGCAAACAGCAAACACACAGC<br>CCTCCCTGCCTGCTGACCTTGGAGCTGGGGCAGAGGTCAGAGAC<br>CTCTCTGGGCCCATGCCACCTCCAACATCCACTCGACCCCTTGG<br>AATTTCGGTGGAGAGGAGCAGAGGTTGTCCTGGCGTGGTTTAGG<br>TAGTGTGAGAGGGTCTAGAAGGCTCAGAGGCACACAGGAGTTTC<br>TGGGCTCACCCTGCCCCCTTCCAACCCCTCAGTTCCCATCCTCC<br>AGCAGCTGTTTGTGTGCTGCCTCTGAAGTCCACACTGAACAAAC<br>TTCAGCCTACTCATGTCCCTAAAATGGGCAAACATTGCAAGCAG<br>CAAACAGCAAACACACAGCCCTCCCTGCCTGCTGACCTTGGAGC<br>TGGGGCAGAGGTCAGAGACCTCTCTG |
| TBG Promoter | 30 | GGGCTGGAAGCTACCTTTGACATCATTTCCTCTGCGAATGCATG<br>TATAATTTCTACAGAACCTATTAGAAAGGATCACCCAGCCTCTG<br>CTTTTGTACAACTTTCCCTTAAAAAACTGCCAATTCCACTGCTG<br>TTTGGCCCAATAGTGAGAACTTTTTCCTGCTGCCTCTTGGTGCT<br>TTTGCCTATGGCCCCTATTCTGCCTGCTGAAGACACTCTTGCCA<br>GCATGGACTTAAACCCCTCCAGCTCTGACAATCCTCTTTCTCTT<br>TTGTTTTACATGAAGGGTCTGGCAGCCAAAGCAATCACTCAAAG<br>TTCAAACCTTATCATTTTTTGCTTTGTTCCTCTTGGCCTTGGTT<br>TTGTACATCAGCTTTGAAAATACCATCCCAGGGTTAATGCTGGG<br>GTTAATTTATAACTAAGAGTGCTCTAGTTTTGCAATACAGGACA<br>TGCTATAAAAATGGAAAGAT |
| hAAT Promoter | 31 | GATCTTGCTACCAGTGGAACAGCCACTAAGGATTCTGCAGTGAG<br>AGCAGAGGGCCAGCTAAGTGGTACTCTCCCAGAGACTGTCTGAC<br>TCACGCCACCCCCTCCACCTTGGACACAGGACGCTGTGGTTTCT<br>GAGCCAGGTACAATGACTCCTTTCGGTAAGTGCAGTGGAAGCTG<br>TACACTGCCCAGGCAAAGCGTCCGGGCAGCGTAGGCGGGCGACT<br>CAGATCCCAGCCAGTGGACTTAGCCCCTGTTTGCTCCTCCGATA<br>ACTGGGGTGACCTTGGTTAATATTCACCAGCAGCCTCCCCCGTT<br>GCCCCTCTGGATCCACTGCTTAAATACGGACGAGGACAGGGCCC<br>TGTCTCCTCAGCTTCAGGCACCACCACTGACCTGGGACAGT |
| Mck Enhancer (MckE) | 32 | CCACTACGGGTTTAGGCTGCCCATGTAAGGAGGCAAGGCCTGGG<br>GACACCCGAGATGCCTGGTTATAATTAACCCAGACATGTGGCTG<br>CCCCCCCCCCCCCCAACACCTGCTGCCTCTAAAAATAACCCTGT<br>CCCTGGTGGATC |
| Tandem (2) Mck Enhancers | 33 | CCACTACGGGTTTAGGCTGCCCATGTAAGGAGGCAAGGCCTGGG<br>GACACCCGAGATGCCTGGTTATAATTAACCCAGACATGTGGCTG<br>CCCCCCCCCCCCCCAACACCTGCTGCCTCTAAAAATAACCCTGT<br>CCCTGGTGGATCCCACTACGGGTTTAGGCTGCCCATGTAAGGAG<br>GCAAGGCCTGGGGACACCCGAGATGCCTGGTTATAATTAACCCA<br>GACATGTGGCTGCCCCCCCCCCCCCCAACACCTGCTGCCTCTAA<br>AAATAACCCTGTCCCTGGTGGATC |

TABLE 2-continued

| Name | SEQ ID NO: | Nucleic Acid Sequence |
|---|---|---|
| Tandem Mck (3) Enhancers | 34 | CCACTACGGGTTTAGGCTGCCCATGTAAGGAGGCAAGGCCTGGG<br>GACACCCGAGATGCCTGGTTATAATTAACCCAGACATGTGGCTG<br>CCCCCCCCCCCCCCAACACCTGCTGCCTCTAAAAATAACCCTGT<br>CCCTGGTGGATCCCACTACGGGTTTAGGCTGCCCATGTAAGGAG<br>GCAAGGCCTGGGGACACCCGAGATGCCTGGTTATAATTAACCCA<br>GACATGTGGCTGCCCCCCCCCCCCCCAACACCTGCTGCCTCTAA<br>AAATAACCCTGTCCCTGGTGGATCCCACTACGGGTTTAGGCTGC<br>CCATGTAAGGAGGCAAGGCCTGGGGACACCCGAGATGCCTGGTT<br>ATAATTAACCCAGACATGTGGCTGCCCCCCCCCCCCCCAACACC<br>TGCTGCCTCTAAAAATAACCCTGTCCCTGGTGGATC |
| Chicken beta actin intron (CpG depleted) | 35 | GTGAGCGGCGGATGCCCTTCTCCTCTGGCTGTAATTAGTCTTGG<br>TTTACTTGTTTCTTTTCTGTGGCTGTTGAAAGCCTTGAGGGGCT<br>CTGGAGGGCCCTTTGTGTGGGGGAGTGCTTGGGGGTGTTGTTGT<br>GTGTGTGTTGGGGAGTCTTTGTGCTCTTCTGCCTGTGCTGTGAG<br>TCTGTGGTTGTTGGGCTTTGTGTCTCTCAGTGTGTTAGGGGAGT<br>TGCTGGGGTGTGCCCTTGTGTGGGGGGGCTGTAGGGGAACAAAG<br>GCTGTTGTGGGTGTGTGTTGGGGGGGTGAGCAGGGGGTGTGGGT<br>TTTGTTGGCTGCAACCCCCCCTGCACCCCCCTCCCTAGTTGCTG<br>AGCATGCCTGCTTTGGTGTGGGCTCTTATGGGTTGGTTGGGCTT<br>CTTGCTGGTGGGGGTGGTGCAGGTGGGGGTGCTGGTGGGTGGGC<br>TCCTTGGCTGGGAGGGCTTGGGGAGGGGTTGTGCCCCTGAGTCT<br>GTGCTGTTAGGTTGTAGCTCAGCCATTGCCTTTTTTGTAGAGGG<br>TCAGGGACTTCCTTTGTCCCAAATCTGTGTGAGCTAAATCTGGG<br>AGGTCTCTCACCCCCTCTAGTGGTTGGGTAAGTGTGTGTCTGCA<br>GGAAGGAAAGGGTGGGAGGGCCTTTTGTTTCTTCTCTTCCCCTT<br>CTCCCTCTCCAGCCTTGGGCTGTCTTGGGGGATGCTGCCTTTGG<br>GGGGATGGGCAGGGTGGGTTTGCTTCTGGTTGTGACTGTGCTCT<br>AGAGCCTCTGCTAACCTGTTCTGCCTTCTTCTTTTTCCTACAGC<br>TCCTGGGCAATTGCTGGTTATTGTGCTGTCTCTATTTTGGCAAA<br>G |
| VH4 intron | 36 | GTGAGTATCTCAGGGATCCAGACATGGGGATATGGGAGGTGCCT<br>CTGATC<br>CCAGGGCTCACTGTGGGTCTCTCTGTTCACAG |
| Chimeric intron | 37 | GTAAGTATCAAGGTTACAAGACAGGTTTAAGGAGACCAATAGAA<br>ACTGGGCTTGTCGAGACAGAGAAGACTCTTGCGTTTCTGATAGG<br>CACCTATTGGTCTTACTGACATCCACTTTGCCTTTCTCTCCACA<br>G |
| SV40 intron | 38 | GTAAGTTTAGTCTTTTTGTCTTTTATTTCAGGTCCCGGATCCGG<br>TGGTGGTGCAAATCAAAGAACTGCTCCTCAGTGGATGTTGCCTT<br>TACTTCTAG |
| β-globin/Ig Intron | 39 | GTAAGTATCAAGGTTACAAGACAGGTTTAAGGAGACCAATAGAA<br>ACTGGGCTTGTCGAGACAGAGAAGACTCTTGCGTTTCTGATAGG<br>CACCTATTGGTCTTACTGACATCCACTTTGCCTTTCT |
| Rabbit globin polyA | 40 | GATCTTTTTCCCTCTGCCAAAAATTATGGGGACATCATGAAGCC<br>CCTTGAGCATCTGACTTCTGGCTAATAAAGGAAATTTATTTTCA<br>TTGCAATAGTGTGTTGGAATTTTTTGTGTCTCTCACTCG |
| polyA | 41 | AGGCCTAATAAAGAGCTCAGATGCATCGATCAGAGTGTGTTGGT<br>TTTTTG |
| 5'-ITR | 42 | CGCGCGCTCGCTCGCTCACTGAGGCCGCCCGGGCAAAGCCCGGG<br>CGTCGGGCGACCTTTGGTCGCCCGGCCTCAGTGAGCGAGCGAGC<br>GCGCAGAGAGGGAGTGGCCAACTCCATCACTAGGGGTTCCT<br>REP PROTEIN BINDING SITE (RPS) IS<br>UNDERLINED. |
| 3'-ITR | 43 | AGGAACCCCTAGTGATGGAGTTGGCCACTCCCTCTCTGCGCGCT<br>CGCTCGCTCACTGAGGCCGGGCGACCAAAGGTCGCCCGACGCCC<br>GGGCTTTGCCCGGGCGGCCTCAGTGAGCGAGCGAGCGCGCAG<br>REP PROTEIN BINDING SITE (RPS) IS<br>UNDERLINED. |
| modified IL-2 leader (signal) peptide | 44 | ATGTACAGAATGCAGCTGCTGCTGCTCATTGCCCTGTCTCTGGC<br>CCTGGTCACCAATTCT |

In one embodiment, an expression cassette for use in an AAV vector is provided. In certain embodiments, a single-stranded AAV (ssAAV) may be used. The AAV genome is packaged as a linear ssDNA molecule with the palindromic inverted terminal repeat (ITR) sequences which form dsDNA hairpin structures at each end. These serve as replication origins during productive infection and as priming sites for host-cell DNA polymerase to begin synthesis of a complementary strand.

In that embodiment, the AAV expression cassette includes at least one AAV inverted terminal repeat (ITR) sequence. In another embodiment, the expression cassette comprises 5' ITR sequences and 3' ITR sequences. In one embodiment, the 5' and 3' ITRs flank the codon optimized nucleic acid sequence that encodes the transgene. Thus, as described herein, an AAV expression cassette is meant to describe an expression cassette as described above flanked on its 5' end by a 5' AAV inverted terminal repeat sequence (ITR) and on its 3' end by a 3' AAV ITR. Thus, this rAAV genome contains the minimal sequences required to package the expression cassette into an AAV viral particle, i.e., the AAV 5' and 3' ITRs. The AAV ITRs may be obtained from the ITR sequences of any AAV, such as described herein. These ITRs may be of the same AAV origin as the capsid employed in the resulting recombinant AAV, or of a different AAV origin (to produce an AAV pseudotype). In one embodiment, the ITR sequences from AAV2, or the deleted version thereof (AITR), are used for convenience and to accelerate regulatory approval. However, ITRs from other AAV sources may be selected. Where the source of the ITRs is from AAV2 and the AAV capsid is from another AAV source, the resulting vector may be termed pseudotyped. Typically, the AAV vector genome comprises an AAV 5' ITR, the coding sequences and any regulatory sequences, and an AAV 3' ITR. However, other configurations of these elements may be suitable. A shortened version of the 5' ITR, termed AITR, has been described in which the D-sequence and terminal resolution site (trs) are deleted. In other embodiments, the full-length AAV 5' and 3' ITRs are used. Each rAAV genome can be then introduced into a production plasmid.

In certain embodiments, a self-complementary vector, e.g., scAAV, may be used (see, e.g., Wu, 2007, Human Gene Therapy, 18(2): 171-82, McCarty et al, 2001, Gene Therapy, Vol 8, Number 16, Pages 1248-1254; and U.S. Pat. Nos. 6,596,535; 7,125,717; and 7,456,683, each of which is incorporated herein by reference in its entirety). "Self-complementary AAV" refers a plasmid or vector having an expression cassette in which a coding region carried by a recombinant AAV nucleic acid sequence has been designed to form an intra-molecular double-stranded DNA template. Unlike ssDNA genomes, the scAAV genome is not subject to host-cell DNA polymerase and does not require synthesis of a complementary strand. Upon infection, rather than waiting for cell mediated synthesis of the second strand, the two complementary halves of scAAV will associate to form one double stranded DNA (dsDNA) unit that is ready for immediate replication and transcription. Sec, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

Vectors for Gene Delivery

Another aspect of the present invention relates to the genetic engineering of nucleic acid sequences in a vector expression system. In one embodiment, the vector is a viral vector, including but not limited to recombinant adeno-associated viral (rAAV) vectors (e.g. Gao G., et al 2003 *Proc. Natl. Acad. Sci. U.S.A.* 100(10):6081-6086), lentiviral vectors (e.g. Matrai, J, et al. 2011, *Hepatology* 53, 1696-707), retroviral vectors (e.g. Axelrod, J H, et al. 1990. *Proc Natl Acad Sci USA;* 87, 5173-7), adenoviral vectors (e.g. Brown et al., 2004 *Blood* 103, 804-10), herpes-simplex viral vectors (Marconi, P. et al. *Proc Natl Acad Sci USA.* 1996 93(21): 11319-11320; Bacz, M V, et al. Chapter 19—Using Herpes Simplex Virus Type 1-Based Amplicon Vectors for Neuroscience Research and Gene Therapy of Neurologic Diseases, Ed.: Robert T. Gerlai, *Molecular-Genetic and Statistical Techniques for Behavioral and Neural Research*, Academic Press, 2018: Pages 445-477), and retrotransposon-based vector systems (e.g. Soifer, 2004, *Current Gene Therapy* 4(4):373-384). In another embodiment, the vector is a non-viral vector. rAAV vectors have limited packaging capacity of the vector particles (i.e. approximately 4.7 kb), constraining the size of the transgene expression cassette to obtain functional vectors (Jiang et al., 2006 *Blood.* 108:107-15).

The length of the heterologous gene and the length of the regulatory nucleic acid sequences comprising, but not limited to promoter(s) and polyA elements are taken into consideration when selecting a stuffer region suitable for a transgene and target tissue.

In another aspect, the expression cassettes are suitable for packaging in an AAV capsid, as such the cassette comprises (1) AAV inverted terminal repeats (ITRs) flank the expression cassette; (2) regulatory control elements, a) promoter/enhancers, such as any one of, but not limited to promoters described in Table 2, b) a poly A signal, and c) optionally an intron; and (3) a heterologous gene providing (e.g., coding for) one or more RNA or protein products of interest.

In certain embodiments, the transgene comprises a gene selected from Tables 3A-3C. In other embodiments for expressing an intact or substantially intact mAb, the constructs described herein comprise the following components: (1) AAV2 inverted terminal repeats that flank the expression cassette; (2) regulatory control elements, a) promoter/enhancers, such as any one of, but not limited to promoters described in Table 2, b) a poly A signal, and c) optionally an intron; and (3) nucleic acid sequences coding for a heavy chain Fab and/or a light chain Fab of a therapeutic antibody. Some embodiments provide for nucleic acid sequences coding for the heavy chain Fab of an anti-VEGF (e.g., sevacizumab, ranibizumab, bevacizumab, and brolucizumab), anti-EpoR (e.g., LKA-651), anti-ALK1 (e.g., ascrinvacumab), anti-C5 (e.g., tesidolumab and cculizumab), anti-CD105 (e.g., carotuximab), anti-CCIQ (e.g., ANX-007), anti-TNFα (e.g., adalimumab, infliximab, and golimumab), anti-RGMa (e.g., elezanumab), anti-TTR (e.g., NI-301 and PRX-004), anti-CTGF (e.g., pamrevlumab), anti-IL6R (e.g., satralizumab and sarilumab), anti-IL4R (e.g., dupilumab), anti-IL17A (e.g., ixekizumab and secukinumab), anti-IL-5 (e.g., mepolizumab), anti-IL12/IL23 (e.g., ustekinumab), anti-CD19 (e.g., inebilizumab), anti-ITGF7 mAb (e.g., ctrolizumab), anti-SOST mAb (e.g., romosozumab), anti-pKal mAb (e.g., lanadelumab), anti-ITGA4 (e.g., natalizumab), anti-ITGA4B7 (e.g., vedolizumab), anti-BLyS (e.g., belimumab), anti-PD-1 (e.g., nivolumab and pembrolizumab), anti-RANKL (e.g., denosomab), anti-PCSK9 (e.g., alirocumab and evolocumab), anti-ANGPTL3 (e.g., evinacumab*), anti-OxPL (e.g., E06), anti-fD (e.g., lampalizumab), or anti-MMP9 (e.g., andecaliximab); optionally an Fc polypeptide or fragment of the same isotype as the native form of the therapeutic antibody, such as an IgG isotype amino acid sequence IgG1, IgG2 or IgG4 or modified Fc thereof; and the light chain of an anti-VEGF (e.g., sevacizumab, ranibizumab, bevacizumab, and brolucizumab), anti-EpoR (e.g., LKA-651), anti-ALK1 (e.g., ascrinvacumab), anti-C5 (e.g., tesidolumab and eculizumab), anti-CD105 or anti-ENG (e.g., carotuximab), anti-CCIQ (e.g., ANX-007), anti-TNFα (e.g., adalimumab, infliximab, and golimumab), anti-RGMa (e.g., clezanumab), anti-TTR (e.g., NI-301 and PRX-004), anti-CTGF (e.g., pamrevlumab), anti-IL6R (e.g., satralizumab and sarilumab), anti-IL4R (e.g., dupilumab), anti-IL17A (e.g., ixckizumab and secukinumab), anti-IL-5 (e.g., mepolizumab), anti-IL12/IL23 (e.g., ustekinumab), anti-CD19 (e.g., inebilizumab), anti-ITGF7 mAb (e.g., etrolizumab), anti-SOST mAb (e.g., romosozumab), anti-pKal mAb (e.g., lanadelumab), anti-ITGA4 (e.g., natalizumab), anti-ITGA4B7 (e.g., vedolizumab), anti-BLyS (e.g., belimumab), anti-PD-1 (e.g., nivolumab and pembrolizumab), anti-RANKL (e.g., densomab), anti-PCSK9 (e.g., alirocumab and evolocumab), anti-ANGPTL3 (e.g., evinacumab), anti-OxPL (e.g., E06), anti-fD (e.g., lampalizumab), or anti-MMP9 (e.g., andecaliximab); wherein the heavy chain (Fab and Fc region) and the light chain are separated by a self-cleaving furin (F)/F2A or flexible linker, ensuring expression of approximately equal amounts of the heavy and the light chain polypeptides.

In the various embodiments, the target tissue may be neural tissue, bone, kidney, liver, muscle, spleen, lung or endothelial tissue, or a particular receptor or tumor, and the regulatory agent is derived from a heterologous protein or domain that specifically recognizes and/or binds that tissue, particularly liver and muscle. The transgenes expressed in liver and muscle are considered systemic expression, since enhanced delivery of liver-expressed protein may be sufficient to cross into other tissues including crossing the blood brain barrier to the CNS and delivering therapeutics for treating neurological disorders or neurological symptoms of a systemic disorder.

rAAV Particles

The provided methods are suitable for use in the production of any isolated recombinant AAV particles, in the production of a composition comprising any isolated recombinant AAV particles, or in the method for treating a disease or disorder in a subject in need thereof comprising the administration of any isolated recombinant AAV particles. As such, the rAAV can be of any serotype, modification, or derivative, known in the art, or any combination thereof (e.g., a population of rAAV particles that comprises two or more serotypes, e.g., comprising two or more of AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B. AAV.PHP.cB, AAV2.5, AAV2YF, AAV3B, AAV.LK03, AAV.HSC1. AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 or other rAAV particles, or combinations of two or more thereof.

In some embodiments, rAAV particles have a capsid protein from an AAV serotype selected from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B. AAV.PHP.cB. AAV2.5, AAV2tYF. AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10. AAV.HSC11, AAV.HSC12, AAV.HSC13, AAV.HSC14, AAV.HSC15, or AAV.HSC16 or a derivative, modification, or pseudotype thereof. In some embodiments, rAAV particles comprise a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to e.g., VP1, VP2 and/or VP3 sequence of an AAV capsid serotype selected from AAV1. AAV2. AAV3, AAV4, AAV5, AAV6, AAV7, AAV8, AAV9, AAV10, AAV11, AAV12. AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, rAAV.Anc80L65, AAV.7m8, AAV.PHP.B. AAV.PHP.cB, AAV2.5, AAV2YF, AAV3B, AAV.LK03, AAV.HSC1, AAV.HSC2. AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16.

In some embodiments, rAAV particles comprise a capsid protein from an AAV capsid serotype selected from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B. AAV.PHP.cB, AAV2.5, AAV2ŁYF. AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16, or a derivative, modification, or pseudotype thereof. In some embodiments, rAAV particles comprise a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to e.g., VP1, VP2 and/or VP3 sequence of an AAV capsid serotype selected from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39. AAV.Rh74, AAV.RHM4-1, AAV.hu37, AAV.Anc80, AAV.Anc80L65, AAV.7m8, AAV.PHP.B. AAV.PHP.cB. AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16.

In some embodiments, rAAV particles comprise the capsid of Anc80 or Anc80L65, as described in Zinn et al., 2015, Cell Rep. 12(6): 1056-1068, which is incorporated by reference in its entirety. In certain embodiments, the rAAV particles comprise the capsid with one of the following amino acid insertions: LGETTRP or LALGETTRP, as described in U.S. Pat. Nos. 9,193,956; 9,458,517; and 9,587,282 and US patent application publication no. 2016/0376323, each of which is incorporated herein by reference in its entirety. In some embodiments, rAAV particles comprise the capsid of AAV.7m8, as described in U.S. Pat. Nos. 9,193,956; 9,458,517; and 9,587,282 and US patent application publication no. 2016/0376323, each of which is incorporated herein by reference in its entirety. In some embodiments, rAAV particles comprise any AAV capsid disclosed in U.S. Pat. No. 9,585,971, such as AAVPHP.B. In some embodiments, rAAV particles comprise any AAV capsid disclosed in U.S. Pat. No. 9,840,719 and WO 2015/013313, such as AAV.Rh74 and RHM4-1, each of which is incorporated herein by reference in its entirety. In some embodiments. rAAV particles comprise any AAV capsid disclosed in WO 2014/172669, such as AAV rh.74, which is incorporated herein by reference in its entirety. In some embodiments, rAAV particles comprise the capsid of AAV2/5, as described in Georgiadis et al., 2016, Gene Therapy 23: 857-862 and Georgiadis et al., 2018, Gene Therapy 25: 450, each of which is incorporated by reference in its entirety. In some embodiments, rAAV particles comprise any AAV capsid disclosed in WO 2017/070491, such as AAV2tYF, which is incorporated herein by reference in its entirety. In some embodiments, rAAV particles comprise the capsids of AAVLK03 or AAV3B, as described in Puzzo et al., 2017, Sci. Transl. Med. 29(9): 418, which is incorporated by reference in its entirety. In some embodiments, rAAV particles comprise any AAV capsid disclosed in U.S. Pat. Nos. 8,628,966; 8,927,514; 9,923,120 and WO 2016/049230, such as HSC1, HSC2, HSC3, HSC4, HSC5, HSC6, HSC7, HSC8, HSC9, HSC10, HSC11, HSC12, HSC13, HSC14, HSC15, or HSC16, each of which is incorporated by reference in its entirety.

In some embodiments, rAAV particles comprise an AAV capsid disclosed in any of the following patents and patent applications, each of which is incorporated herein by reference in its entirety: U.S. Pat. Nos. 7,282,199; 7,906,111; 8,524,446; 8,999,678; 8,628,966; 8,927,514; 8,734,809; 9,284,357; 9,409,953; 9,169,299; 9,193,956; 9,458,517; and 9,587,282; US patent application publication nos. 2015/0374803; 2015/0126588; 2017/0067908; 2013/0224836; 2016/0215024; 2017/0051257; and International Patent Application Nos. PCT/US2015/034799; PCT/EP2015/053335. In some embodiments, rAAV particles have a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of an AAV capsid disclosed in any of the following patents and patent applications, each of which is incorporated herein by reference in its entirety: U.S. Pat. Nos. 7,282,199; 7,906,111; 8,524,446; 8,999,678; 8,628,966; 8,927,514; 8,734,809; 9,284,357; 9,409,953; 9,169,299; 9,193,956; 9,458,517; and 9,587,282; US patent application publication nos. 2015/0374803; 2015/0126588; 2017/0067908; 2013/0224836; 2016/0215024; 2017/0051257; and International Patent Application Nos. PCT/US2015/034799; PCT/EP2015/053335.

In some embodiments, rAAV particles have a capsid protein disclosed in Intl. Appl. Publ. No. WO 2003/052051 (see, e.g., SEQ ID NO: 2 of '501), WO 2005/033321 (see, e.g., SEQ ID NOs: 123 and 88 of '321), WO 03/042397 (see, e.g., SEQ ID NOs: 2, 81, 85, and 97 of '397), WO 2006/068888 (see, e.g., SEQ ID NOs: 1 and 3-6 of '888), WO 2006/110689, (see, e.g., SEQ ID NOs: 5-38 of '689) WO2009/104964 (see, e.g., SEQ ID NOs: 1-5, 7, 9, 20, 22, 24 and 31 of '964), WO 2010/127097 (see, e.g., SEQ ID NOs: 5-38 of '097), and WO 2015/191508 (see, e.g., SEQ ID NOs: 80-294 of '508), and U.S. Appl. Publ. No. 20150023924 (see, e.g., SEQ ID NOs: 1, 5-10 of '924), the contents of each of which is herein incorporated by reference in its entirety. In some embodiments, rAAV particles have a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of an AAV capsid disclosed in Intl. Appl. Publ. No. WO 2003/052051 (see, e.g., SEQ ID NO: 2 of '051), WO 2005/033321 (see, e.g., SEQ ID NOs: 123 and 88 of '321), WO 03/042397 (see, e.g., SEQ ID NOs: 2, 81, 85, and 97 of '397), WO 2006/068888 (see, e.g., SEQ ID NOs: 1 and 3-6 of '888), WO 2006/110689 (see, e.g., SEQ ID NOs: 5-38 of '689) WO2009/104964 (see, e.g., SEQ ID NOs: 1-5, 7, 9, 20, 22, 24 and 31 of '964), WO 2010/127097 (see, e.g., SEQ ID NOs: 5-38 of '097), and WO 2015/191508 (see, e.g., SEQ ID NOs: 80-294 of '508), and U.S. Appl. Publ. No. 20150023924 (see, e.g., SEQ ID NOs: 1, 5-10 of '924).

Nucleic acid sequences of AAV based viral vectors and methods of making recombinant AAV and AAV capsids are taught, for example, in U.S. Pat. Nos. 7,282,199; 7,906,111; 8,524,446; 8,999,678; 8,628,966; 8,927,514; 8,734,809; 9,284,357; 9,409,953; 9,169,299; 9,193,956; 9,458,517; and 9,587,282; US patent application publication nos. 2015/0374803; 2015/0126588; 2017/0067908; 2013/0224836; 2016/0215024; 2017/0051257; International Patent Application Nos. PCT/US2015/034799; PCT/EP2015/053335; WO 2003/052051, WO 2005/033321, WO 03/042397, WO 2006/068888, WO 2006/110689, WO2009/104964, WO 2010/127097, and WO 2015/191508, and U.S. Appl. Publ. No. 20150023924.

The provided methods are suitable for use in the production of recombinant AAV encoding a transgene. In certain embodiments, the transgene comprises a gene selected from Tables 3A-3C. In some embodiments, the rAAV genome comprises a vector comprising the following components: (1) AAV inverted terminal repeats that flank an expression cassette; (2) regulatory control elements, such as a) promoter/enhancers (see exemplary promoters/enhancers of Table 2), b) a poly A signal, and c) optionally an intron; and (3) nucleic acid sequences coding for a heterologous gene, such as a gene of Tables 3A-3C. In other embodiments for expressing an intact or substantially intact monoclonal antibody (mAb), the rAAV genome comprises a vector comprising the following components: (1) AAV inverted terminal repeats that flank an expression cassette; (2) regulatory control elements, such as a) promoter/enhancers, b) a poly A signal, and c) optionally an intron; and (3) nucleic acid sequences coding for the light chain Fab and heavy chain Fab of the antibody, such as the antibody of Tables 3B or 3C, or at least the heavy chain or light chain Fab, and optionally a heavy chain Fc region. In still other embodiments for expressing an intact or substantially intact mAb, the rAAV genome comprises a vector comprising the following components: (1) AAV inverted terminal repeats that flank an expression cassette; (2) regulatory control elements, such as a) promoter/enhancers, b) a poly A signal, and c) optionally an intron; and (3) nucleic acid sequences coding for the heavy chain Fab of an anti-VEGF (e.g., sevacizumab, ranibizumab, bevacizumab, and brolucizumab), anti-EpoR (e.g., LKA-651), anti-ALK1 (e.g., ascrinvacumab), anti-C5 (e.g., tesidolumab and eculizumab), anti-CD105 (e.g., carotuximab), anti-CCIQ (e.g., ANX-007), anti-TNFα (e.g., adalimumab, infliximab, and golimumab), anti-RGMa (e.g., elezanumab), anti-TTR (e.g., NI-301 and PRX-004), anti-CTGF (e.g., pamrevlumab), anti-IL6R (e.g., satralizumab and sarilumab), anti-IL4R (e.g., dupilumab), anti-IL17A (e.g., ixckizumab and secukinumab), anti-IL-5 (e.g., mepolizumab), anti-IL12/IL23 (e.g., ustekinumab), anti-CD19 (e.g., inebilizumab), anti-ITGF7 mAb (e.g., etrolizumab), anti-SOST mAb (e.g., romosozumab), anti-pKal mAb (e.g., lanadelumab), anti-ITGA4 (e.g., natalizumab), anti-ITGA4B7 (e.g., vedolizumab), anti-BLyS (e.g., belimumab), anti-PD-1 (e.g., nivolumab and pembrolizumab), anti-RANKL (e.g., densomab), anti-PCSK9 (e.g., alirocumab and evolocumab), anti-ANGPTL3 (e.g., cvinacumab*), anti-OxPL (e.g., E06), anti-fD (e.g., lampalizumab), or anti-MMP9 (e.g., andecaliximab); optionally an Fc polypeptide of the same isotype as the native form of the therapeutic antibody, such as an IgG isotype amino acid sequence IgG1, IgG2 or IgG4 or modified Fc thereof; and the light chain of an anti-VEGF (e.g., sevacizumab, ranibizumab, bevacizumab, and brolucizumab), anti-EpoR (e.g., LKA-651), anti-ALK1 (e.g., ascrinvacumab), anti-C5 (e.g., tesidolumab and eculizumab), anti-CD105 or anti-ENG (e.g., carotuximab), anti-CCIQ (e.g., ANX-007), anti-TNFα (e.g., adalimumab, infliximab, and golimumab), anti-RGMa (e.g., clezanumab), anti-TTR (e.g., NI-301 and PRX-004), anti-CTGF (e.g., pamrevlumab), anti-IL6R (e.g., satralizumab and sarilumab), anti-IL4R (e.g., dupilumab), anti-IL17A (e.g., ixckizumab and secukinumab), anti-IL-5 (e.g., mepolizumab), anti-IL12/IL23 (e.g., ustekinumab), anti-CD19 (e.g., inebilizumab), anti-ITGF7 mAb (e.g., ctrolizumab), anti-SOST mAb (e.g., romosozumab), anti-pKal mAb (e.g., lanadelumab), anti-ITGA4 (e.g., natalizumab), anti-ITGA4B7 (e.g., vedolizumab), anti-BLyS (e.g., belimumab), anti-PD-1 (e.g., nivolumab and pembrolizumab), anti-RANKL (e.g., densomab), anti-PCSK9 (e.g., alirocumab and evolocumab), anti-ANGPTL3 (e.g., evinacumab), anti-OxPL (e.g., E06), anti-fD (e.g., lampalizumab), or anti-MMP9 (e.g., andecaliximab); wherein the heavy chain (Fab and optionally Fc region) and the light chain are separated by a self-cleaving furin (F)/F2A or flexible linker, ensuring expression of equal amounts of the heavy and the light chain polypeptides.

In some embodiments, the rAAV genome comprises a vector comprising the following components: (1) AAV inverted terminal repeats that flank an expression cassette; (2) regulatory control elements, such as a) promoter/enhancers (see exemplary promoters/enhancers of Table 2), b) a poly A signal, and c) optionally an intron; and (3) nucleic acid sequences coding for a pri-microRNA gene, such as a pri-miR-30a, pri-miR-218-1, pri-miR-124-3, or pri-miR-155.

Single-stranded AAV (ssAAV) vectors, wherein the coding sequence and complementary sequence of the transgene expression cassette are on separate strands, are packaged in separate viral capsids. For ssAAV, after transduction occurs and genome enters the nucleus, the single-to-double stranded conversion of the DNA undergoes inter-molecular annealing or second-strand synthesis. In certain embodiments, a single-stranded AAV (ssAAV) can be used. For self-complementary AAV (scAAV) vectors, both the coding and complementary sequence of the transgene expression cassette are present on each plus- and minus-strand genome. In contrast, a scAAV vector with half the size of the ssAAV genome has a mutation in the terminal resolution site (TRS) to form a vector genome with wild-type ITRs at both ends and mutated ITR at the center of symmetry. After uncoating in the target cell nucleus, this DNA structure can readily fold into transcriptionally active double-stranded form through intra-molecular annealing. In certain embodiments, a self-complementary vector, e.g., scAAV, can be used (see, e.g., Wu, 2007, Human Gene Therapy, 18(2): 171-82, McCarty et al, 2001, Gene Therapy, Vol. 8, Number 16, Pages 1248-1254; and U.S. Pat. Nos. 6,596,535; 7,125,717; and 7,456, 683, each of which is incorporated herein by reference in its entirety).

In some embodiments, provided herein are rAAV viral vectors encoding a heterologous gene selected from Tables 3A-3C. In some embodiments, provided herein are rAAV viral vectors encoding an anti-VEGF Fab. In specific embodiments, provided herein are rAAV8-based viral vectors encoding an anti-VEGF Fab. In more specific embodiments, provided herein are rAAV8-based viral vectors encoding ranibizumab. In some embodiments, provided herein are rAAV viral vectors encoding iduronidase (IDUA). In specific embodiments, provided herein are rAAV9-based viral vectors encoding IDUA. In some embodiments, provided herein are rAAV viral vectors encoding iduronate 2-sulfatase (IDS). In specific embodiments, provided herein are rAAV9-based viral vectors encoding IDS. In some embodiments, provided herein are rAAV viral vectors encoding a low-density lipoprotein receptor (LDLR). In specific embodiments, provided herein are rAAV8-based viral vectors encoding LDLR. In some embodiments, provided herein are rAAV viral vectors encoding tripeptidyl peptidase 1 (TPP1) protein. In specific embodiments, provided herein are rAAV9-based viral vectors encoding TPP1. In some embodiments, provided herein are rAAV viral vectors encoding non-membrane associated splice variant of VEGF receptor 1 (sFlt-1). In some embodiments, provided herein are rAAV viral vectors encoding microRNA or shRNA. In some embodiments, provided herein are rAAV viral vectors encoding gamma-sarcoglycan, Rab Escort Protein 1 (REP1/CHM), retinoid isomerohydrolase (RPE65), cyclic nucleotide gated channel alpha 3 (CNGA3), cyclic nucleotide gated channel beta 3 (CNGB3), aromatic L-amino acid decarboxylase (AADC), lysosome-associated membrane protein 2 isoform B (LAMP2B), Factor VIII, Factor IX, retinitis pigmentosa GTPase regulator (RPGR), retinoschisin (RS1), sarcoplasmic reticulum calcium ATPase (SERCA2a), aflibercept, battenin (CLN3), transmembrane ER protein (CLN6), glutamic acid decarboxylase (GAD), Glial cell line-derived neurotrophic factor (GDNF), aquaporin 1 (AQP1), dystrophin, myotubularin 1 (MTM1), follistatin (FST), glucose-6-phosphatase (G6Pase), apolipoprotein A2 (APOA2), uridine diphosphate glucuronosyl transferase 1A1 (UGT1A1), arylsulfatase B (ARSB), N-acetyl-alpha-glucosaminidase (NAGLU), alpha-glucosidase (GAA), alpha-galactosidase (GLA), beta-galactosidase (GLB1), lipoprotein lipase (LPL), alpha 1-antitrypsin (AAT), phosphodiesterase 6B (PDE6B), ornithine carbamoyltransferase 90TC), survival motor neuron (SMN1), survival motor neuron (SMN2), neurturin (NRTN), Neurotrophin-3 (NT-3/NTF3), porphobilinogen deaminase (PBGD), nerve growth factor (NGF), mitochondrially encoded NADH:ubiquinone oxidoreductase core subunit 4 (MT-ND4), protective protein cathepsin A (PPCA), dysferlin, MER proto-oncogene, tyrosine kinase (MERTK), cystic fibrosis transmembrane conductance regulator (CFTR), or tumor necrosis factor receptor (TNFR)-immunoglobulin (IgG1) Fc fusion.

In additional embodiments, rAAV particles comprise a pseudotyped AAV capsid. In some embodiments, the pseudotyped AAV capsids are rAAV2/8 or rAAV2/9 pseudotyped AAV capsids. Methods for producing and using pseudotyped rAAV particles are known in the art (see, e.g., Duan et al., J. Virol., 75:7662-7671 (2001); Halbert et al., J. Virol., 74:1524-1532 (2000); Zolotukhin et al., Methods 28:158-167 (2002); and Auricchio et al., Hum. Molec. Genet. 10:3075-3081, (2001).

In additional embodiments, rAAV particles comprise a capsid containing a capsid protein chimeric of two or more AAV capsid serotypes. In some embodiments, the capsid protein is a chimeric of 2 or more AAV capsid proteins from AAV serotypes selected from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B. AAV.PHP.eB. AAV2.5. AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16.

In certain embodiments, a single-stranded AAV (ssAAV) can be used. In certain embodiments, a self-complementary vector, e.g., scAAV, can be used (see, e.g., Wu, 2007, Human Gene Therapy, 18(2): 171-82, McCarty et al, 2001, Gene Therapy, Vol. 8, Number 16, Pages 1248-1254; and U.S. Pat. Nos. 6,596,535; 7,125,717; and 7,456,683, each of which is incorporated herein by reference in its entirety).

In some embodiments, rAAV particles comprise a capsid protein from an AAV capsid serotype selected from AAV8 or AAV9. In some embodiments, the rAAV particles comprise a capsid protein from an AAV capsid serotype selected from the group consisting of AAV7, AAV8, AAV9, AAV.rh8, AAV.rh10, AAV.rh20, AAV.rh39, AAV.Rh74, AAV.RHM4-1, AAV.hu37, AAV.PHP.B, AAV.PHP.eB, and AAV.7m8. In some embodiments, the rAAV particles comprise a capsid protein with high sequence homology to AAV8 or AAV9 such as, AAV.rh10, AAV.rh20, AAV.rh39, AAV.Rh74, AAV.RHM4-1, and AAV.hu37. In some embodiments, the rAAV particles have an AAV capsid serotype of AAV1 or a derivative, modification, or pseudotype thereof. In some embodiments, the rAAV particles have an AAV capsid serotype of AAV4 or a derivative, modification, or pseudotype thereof. In some embodiments, the rAAV particles have an AAV capsid serotype of AAV5 or a derivative, modification, or pseudotype thereof. In some embodiments, the rAAV particles have an AAV capsid serotype of AAV8 or a derivative, modification, or pseudotype thereof. In some embodiments, the rAAV particles have an AAV capsid serotype of AAV9 or a derivative, modification, or pseudotype thereof.

In some embodiments, rAAV particles comprise a capsid protein that is a derivative, modification, or pseudotype of AAV8 or AAV9 capsid protein. In some embodiments, rAAV particles comprise a capsid protein that has an AAV8 capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of AAV8 capsid protein.

In some embodiments, rAAV particles comprise a capsid protein that is a derivative, modification, or pseudotype of AAV9 capsid protein. In some embodiments, rAAV particles comprise a capsid protein that has an AAV8 capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of AAV9 capsid protein.

In some embodiments, the rAAV particles comprise a capsid protein that has at least 80% or more identity, e.g., 85%, 85%, 87%, 88%, 89%, 90%, 91%, 92%, 93%, 94%, 95%, 96%, 97%, 98%, 99%, 99.5%, etc., i.e. up to 100% identity, to the VP1, VP2 and/or VP3 sequence of AAV7, AAV8, AAV9, AAV.rh8, AAV.rh10, AAV.rh20, AAV.rh39, AAV.Rh74, AAV.RHM4-1, AAV.hu37, AAV.PHP.B, AAV.PHP.eB, or AAV.7m8 capsid protein. In some embodiments, the rAAV particles comprise a capsid protein that has at least 80% or more identity, e.g., 85%, 85%, 87%, 88%, 89%, 90%, 91%, 92%, 93%, 94%, 95%, 96%, 97%, 98%, 99%, 99.5%, etc., i.e. up to 100% identity, to the VP1, VP2 and/or VP3 sequence of an AAV capsid protein with high sequence homology to AAV8 or AAV9 such as, AAV.rh10, AAV.rh20, AAV.rh39, AAV.Rh74, AAV.RHM4-1, and AAV.hu37.

In additional embodiments, rAAV particles comprise a mosaic capsid. Mosaic AAV particles are composed of a mixture of viral capsid proteins from different serotypes of AAV. In some embodiments, rAAV particles comprise a mosaic capsid containing capsid proteins of a serotype selected from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV.PHP.eB, AAV2.5, AAV2YF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16.

In some embodiments, rAAV particles comprise a mosaic capsid containing capsid proteins of a serotype selected from AAV1, AAV2, AAV5, AAV6, AAV7, AAV8, AAV9, AAV10, AAVrh.8, and AAVrh.10.

In additional embodiments, rAAV particles comprise a pseudotyped rAAV particle. In some embodiments, the pseudotyped rAAV particle comprises (a) a nucleic acid vector comprising AAV ITRs and (b) a capsid comprised of capsid proteins derived from AAVx (e.g., AAV1. AAV3, AAV4, AAV5, AAV6, AAV7, AAV8, AAV9, AAV10 AAV11, AAV12, AAV13, AAV14, AAV15 and AAV16). In additional embodiments, rAAV particles comprise a pseudotyped rAAV particle comprised of a capsid protein of an AAV serotype selected from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B. AAV.PHP.cB, AAV2.5, AAV2YF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In additional embodiments, rAAV particles comprise a pseudotyped rAAV particle containing AAV8 capsid protein. In additional embodiments, rAAV particles comprise a pseudotyped rAAV particle is comprised of AAV9 capsid protein. In some embodiments, the pseudotyped rAAV8 or rAAV9 particles are rAAV2/8 or rAAV2/9 pseudotyped particles. Methods for producing and using pseudotyped rAAV particles are known in the art (see, e.g., Duan et al., J. Virol., 75:7662-7671 (2001); Halbert et al., J. Virol., 74:1524-1532 (2000); Zolotukhin et al., Methods 28:158-167 (2002); and Auricchio et al., Hum. Molec. Genet. 10:3075-3081, (2001).

In additional embodiments, rAAV particles comprise a capsid containing a capsid protein chimeric of two or more AAV capsid serotypes. In further embodiments, the capsid protein is a chimeric of 2 or more AAV capsid proteins from AAV serotypes selected from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B. AAV.PHP.cB. AAV2.5, AAV2YF, AAV3B, rAAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In further embodiments, the capsid protein is a chimeric of 2 or more AAV capsid proteins from AAV serotypes selected from AAV1, AAV2, AAV5, AAV6, AAV7, AAV8, AAV9, AAV10, AAVrh.8, and AAVrh.10.

In some embodiments, the rAAV particles comprise an AAV capsid protein chimeric of AAV8 capsid protein and one or more AAV capsid proteins from an AAV serotype selected from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B. AAV.PHP.cB, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In some embodiments, the rAAV particles comprise an AAV capsid protein chimeric of AAV8 capsid protein and one or more AAV capsid proteins from an AAV serotype selected from AAV1, AAV2, AAV5, AAV6, AAV7, AAV9, AAV10, AAVrh.8, and AAVrh.10.

In some embodiments, the rAAV particles comprise an AAV capsid protein chimeric of AAV9 capsid protein the capsid protein of one or more AAV capsid serotypes selected from AAV1, AAV2, AAV3, AAV4, AAV5, AAV6, AAV7, AAV8, AAV9, AAV10, AAV11, AAV12, AAV13, AAV14, AAV15 and AAV16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B. AAV.PHP.cB. AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16.

In some embodiments, the rAAV particles comprise an AAV capsid protein chimeric of AAV9 capsid protein the capsid protein of one or more AAV capsid serotypes selected from AAV1, AAV2, AAV3, AAV4, AAV5, AA6, AAV7, AAV8, AAV9, AAVrh.8, and AAVrh.10.

Methods of Making rAAV Molecules

Another aspect of the present invention involves making molecules disclosed herein. In some embodiments, a molecule according to the invention is made by providing a nucleotide comprising the nucleic acid sequence encoding an AAV capsid protein; and using a packaging cell system to prepare corresponding rAAV particles with capsid coats made up of the capsid protein. In some embodiments, the nucleic acid sequence encodes a sequence having at least 60%, 70%, 80%, 85%, 90%, or 95%, preferably 96%, 97%, 98%, 99% or 99.9%, identity to the sequence of a capsid protein molecule described herein, and retains (or substantially retains) biological function of the capsid protein and the inserted peptide from a heterologous protein or domain thereof. In some embodiments, the nucleic acid encodes a sequence having at least 60%, 70%, 80%, 85%. 90%, or 95%, preferably 96%, 97%, 98%, 99% or 99.9%, identity to a particular sequence of the AAV capsid protein, while retaining (or substantially retaining) biological function of the AAV capsid protein.

The capsid protein, coat, and rAAV particles may be produced by techniques known in the art. In some embodiments, the viral genome comprises at least one inverted terminal repeat to allow packaging into a vector. In some embodiments, the viral genome further comprises a cap gene and/or a rep gene for expression and splicing of the cap gene. In certain embodiments, the cap and rep genes are provided by a packaging cell and not present in the viral genome.

In some embodiments, the nucleic acid encoding the capsid protein is cloned into an AAV Rep-Cap helper plasmid in place of the existing capsid gene. When introduced together into host cells, this plasmid helps package an rAAV genome into the capsid protein as the capsid coat. Packaging cells can be any cell type possessing the genes necessary to promote AAV genome replication, capsid assembly, and packaging. Nonlimiting examples include 293 cells or derivatives thereof, HELA cells, or insect cells.

Standard techniques can be used for recombinant DNA, oligonucleotide synthesis, and tissue culture and transformation (e.g., electroporation, lipofection). Enzymatic reactions and purification techniques can be performed according to manufacturer's specifications or as commonly accomplished in the art or as described herein. The foregoing techniques and procedures can be generally performed according to conventional methods well known in the art and as described in various general and more specific references that are cited and discussed throughout the present specification. See, e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose. Unless specific definitions are provided, the nomenclatures utilized in connection with, and the laboratory procedures and techniques of, analytical chemistry, synthetic organic chemistry, and medicinal and pharmaceutical chemistry described herein are those well-known and commonly used in the art. Standard techniques can be used for chemical syntheses, chemical analyses, pharmaceutical preparation, formulation, and delivery, and treatment of patients. Nucleic acid sequences of AAV-based viral vectors, and methods of making recombinant AAV and AAV capsids, are taught, e.g., in U.S. Pat. Nos. 7,282,199; 7,790,449; 8,318,480; 8,962,332; and PCT/EP2014/076466, each of which is incorporated herein by reference in its entirety.

In preferred embodiments, the rAAVs provide transgene delivery vectors that can be used in therapeutic and prophylactic applications, as discussed in more detail below. In some embodiments, the rAAV vector also includes the regulatory control elements discussed supra to influence the expression of the RNA and/or protein products encoded by nucleic acids (heterologous genes) within target cells of the subject. Regulatory control elements and may be tissue-specific, that is, active (or substantially more active or significantly more active) only in the target cell/tissue and are operably linked to the transgene that allows for expression in target tissues.

Provided in particular embodiments are AAV vectors comprising a viral genome comprising an expression cassette for expression of the transgene, under the control of regulatory elements, and flanked by ITRs and an engineered viral capsid as described herein or is at least 95%, 96%, 97%, 98%, 99% or 99.9% identical to the amino acid sequence of the AAV capsid protein.

The recombinant adenovirus can be a first generation vector, with an E1 deletion, with or without an E3 deletion, and with the expression cassette inserted into either deleted region. The recombinant adenovirus can be a second generation vector, which contains full or partial deletions of the E2 and E4 regions. A helper-dependent adenovirus retains only the adenovirus inverted terminal repeats and the packaging signal (phi). The transgene generally is inserted between the packaging signal and the 3'ITR, with or without stuffer sequences to keep the genome close to wild-type size of approximately 36 kb. An exemplary protocol for production of adenoviral vectors may be found in Alba et al., 2005, "Gutless adenovirus: last generation adenovirus for gene therapy," *Gene Therapy* 12:S18-S27, which is incorporated by reference herein in its entirety.

The rAAV vector for delivering the transgene to target tissues, cells, or organs, may also have a tropism for that particular target tissue, cell, or organ, e.g. liver, muscle, brain, or any other organ of cell. The construct can further include additional expression control elements such as introns that enhance expression of the transgene (e.g., introns such as the chicken β-actin intron, minute virus of mice (MVM) intron, human factor IX intron (e.g., FIX truncated intron 1), β-globin splice donor/immunoglobulin heavy chain splice acceptor intron, adenovirus splice donor/immunoglobulin splice acceptor intron, SV40 late splice donor/splice acceptor (19S/16S) intron, and hybrid adenovirus splice donor/IgG splice acceptor intron and polyA signals such as the rabbit β-globin polyA signal, human growth hormone (hGH) polyA signal, SV40 late polyA signal, synthetic polyA (SPA) signal, and bovine growth hormone (bGH) polyA signal. See, e.g., Powell and Rivera-Soto, 2015, Discov. Med., 19(102):49-57.

In certain embodiments, nucleic acids sequences disclosed herein may be codon-optimized, for example, via any codon-optimization technique known to one of skill in the art (see, e.g., review by Quax et al., 2015, Mol Cell 59:149-161).

The viral vectors provided herein may be manufactured using host cells, e.g., mammalian host cells, including host cells from humans, monkeys, mice, rats, rabbits, or hamsters. Nonlimiting examples include: A549, WEHI, 10T1/2, BHK, MDCK, COS1, COS7, BSC 1, BSC 40, BMT 10, VERO, W138, HeLa, 293, Saos, C2C12, L, HT1080, HepG2, primary fibroblast, hepatocyte, and myoblast cells. Typically, the host cells are stably transformed with the sequences encoding the transgene and associated elements (i.e., the vector genome), and genetic components for producing viruses in the host cells, such as the replication and capsid genes (e.g., the rep and cap genes of AAV). For a method of producing recombinant AAV vectors with AAV8 capsids, see Section IV of the Detailed Description of U.S. Pat. No. 7,282,199 B2, which is incorporated herein by reference in its entirety. Genome copy titers of said vectors may be determined, for example, by TAQMAN® analysis. Virions may be recovered, for example, by $CsCl_2$ sedimentation. Alternatively, baculovirus expression systems in insect cells may be used to produce AAV vectors. For a review, see Aponte-Ubillus et al., 2018, *Appl. Microbiol. Biotechnol.* 102:1045-1054, which is incorporated by reference herein in its entirety for manufacturing techniques.

In vitro assays, e.g., cell culture assays, can be used to measure transgene expression from a vector described herein, thus indicating, e.g., potency of the vector. For example, the PER.C6® Cell Line (Lonza), a cell line derived from human embryonic retinal cells, or retinal pigment epithelial cells, e.g., the retinal pigment epithelial cell line hTERT RPE-1 (available from ATCC®), can be used to assess transgene expression. Alternatively, cell lines derived from liver or muscle or other cell types may be used, for example, but not limited, to HuH-7, HEK293, fibrosarcoma HT-1080, HKB-11, C2C12 myoblasts, and CAP cells. Once expressed, characteristics of the expressed product (transgene product) can also be determined, including serum half-life, functional activity of the protein (e.g. enzymatic activity or binding to a target), determination of the glycosylation and tyrosine sulfation patterns, and other assays known in the art for determining protein characteristics.

Therapeutic and Prophylactic Uses

Another aspect relates to therapies which involve administering a transgene via a rAAV vector according to the invention to a subject in need thereof, for delaying, preventing, treating, and/or managing a disease or disorder, and/or ameliorating one or more symptoms associated therewith. A subject in need thereof includes a subject suffering from the disease or disorder, or a subject pre-disposed thereto, e.g., a subject at risk of developing or having a recurrence of the disease or disorder. Generally, a rAAV carrying a particular transgene will find use with respect to a given disease or disorder in a subject where the subject's native gene, corresponding to the transgene, is defective in providing the correct gene product, or correct amounts of the gene product. The transgene then can provide a copy of a gene that is defective in the subject. In other embodiments, the transgene comprises a functional gene that provides a particular function, such as an inhibitory, activating or gene editing function.

Generally, the transgene comprises cDNA that restores protein function to a subject having a genetic mutation(s) in the corresponding native gene. In other embodiments, the cDNA encodes a heterologous protein such as an antibody or antigen-binding molecule for activating or inhibiting cellular surface or intracellular moieties. In other embodiments, the cDNA encodes associated RNA for performing genomic engineering, such as genome editing via homologous recombination. In some embodiments, the transgene encodes a therapeutic RNA, such as a shRNA, artificial miRNA, or element that influences splicing.

Tables 3A-3C below provides a list of heterologous genes that may be used in any of the rAAV vectors described herein, in particular, operably linked to the novel nucleotides described herein, and in particular, may be used in rAAV vectors to treat or prevent the disease with which it is associated, also listed in Tables 3A-3C. As described herein, the rAAV vector may be engineered as described herein using tissue-specific or ubiquitous promoters to express preferentially in the appropriate tissue(s) for delivery of the transgene to effect the therapeutic or prophylactic use. The appropriate AAV serotype may be chosen to optimize the tissue tropism and transduction of the vector suitable for the desired therapeutic or prophylactic use.

TABLE 3A

| Disease | Transgene | UniProtKb No. (or ID No.) | Exemplary GenBank or NCBI RefSeq No. (cDNA size/kb) |
|---|---|---|---|
| MPS I | alpha-L-iduronidase (IDUA) | P35475 | NM_000203.4 (1.962) |
| MPS II (Hunter Syndrome) | iduronate-2-sulfatase (IDS) | P22304 | NM_000202.7 (1.653) |

TABLE 3A-continued

| Disease | Transgene | UniProtKb No. (or ID No.) | Exemplary GenBank or NCBI RefSeq No. (cDNA size/kb) |
|---|---|---|---|
| ceroid lipofuscinosis (Batten disease) | Tripeptidyl peptidase 1 (TPP1) (also known as CLN2) | O14773 | NM_000391.3 (1.692) |
| MPS IIIa (Sanfilippo type A Syndrome) | heparan sulfate sulfatase (also called N-sulfoglucosamine sulfohydrolase (SGSH)) | P22304 | NM_000202.7 (1.653) |
| MPS IIIB (Sanfilippo type B Syndrome) | N-acetyl-alpha-D-glucosaminidase (NAGLU) | P54802 | NM_000263.3 (2.231) |
| MPS VI (Maroteaux-Lamy Syndrome) | arylsulfatase B | P15848 | NM_000046.3 (1.602) |
| Gaucher disease (type 1, II and III) | Glucocerebrosidase, GBA1 | P04062 | D13286 (1.611) |
| Parkinson's Disease | dopamine decarboxylase (DDC)(also known as AADC) | P20711 | |
| Pompe | acid maltase; GAA | P10253 | |
| Metachromatic leukodystrophy | Aryl sulfatase A | | |
| MPS VII (Sly syndrome) | beta-glucuronidase | | |
| MPS VIII | glucosamine-6-sulfate sulfatase | | |
| MPS IX | Hyaluronidase | | |
| Niemann-Pick disease | Sphingomyelinase | | |
| Niemann-Pick disease without sphingomyelinase deficiency | a npc1 gene encoding a cholesterol metabolizing enzyme | | |
| Tay-Sachs disease | Alpha subunit of beta-hexosaminidase | | |
| Sandhoff disease | both alpha and beta subunit of beta-hexosaminidase | | |
| Fabry Disease | alpha-galactosidase | | |
| Fucosidosis | Fucosidase (FUCA1 gene) | | |
| Alpha-mannosidosis | alpha-mannosidase | | |
| Beta-mannosidosis | Beta-mannosidase | | |
| Wolman disease | cholesterol ester hydrolase | | |
| Parkinson's disease | Neurturin | | |
| Parkinson's disease | glial derived growth factor (GDGF) | | |
| Parkinson's disease | tyrosine hydroxylase | | |
| Parkinson's disease | glutamic acid decarboxylase. | | |
| Spinal Muscular Atrophy (SMA) | SMN | | |
| Friedreich's ataxia | Frataxin | | |
| Amyotrophic lateral sclerosis (ALS) | SOD1 | | |
| Glycogen Storage Disease 1a | Glucose-6-phosphatase | | |
| XLMTM | MTM1 | | |
| Crigler Najjar | UGT1A1 | | |
| CPVT | CASQ2 | | |
| Rett syndrome | MECP2 | | |
| Achromatopsia | CNGB3, CNGA3, GNAT2, PDE6C | | |
| Choroidermia | CDM | | |
| Danon Disease | LAMP2 | | |
| Limb Girdle Muscular Dystrophy Type 2C\|Gamma-sarcoglycanopathy | human-alpha-sarcoglycan | Q16586 | |
| Advanced Heart Failure | SERCA2a | | |
| Rheumatoid Arthritis | TNFR:Fc Fusion Gene | | |
| Leber Congenital Amaurosis | GAA | | |
| Limb Girdle Muscular Dystrophy Type 2C\|Gamma-sarcoglycanopathy | gamma-sarcoglycan | | |
| Retinitis Pigmentosa | hMERTK | | |
| Age-Related Macular Degeneration | sFLT01 | | |
| Becker Muscular Dystrophy and Sporadic Inclusion Body Myositis | huFollistatin344 | | |
| Parkinson's Disease | GDNF | | |
| Metachromatic Leukodystrophy (MLD) | cuARSA | | |
| Hepatitis C | anti-HCV shRNA | | |
| Limb Girdle Muscular Dystrophy Type 2D | hSGCA | | |
| Human Immunodeficiency Virus Infections; HIV Infections (HIV-1) | PG9DP | | |
| Acute Intermittant Porphyria | PBGD | | |
| Leber's Hereditary Optical Neuropathy | PIND4v2 | | |
| Alpha-1 Antitrypsin Deficiency | alpha1AT | | |
| Pompe Disease | hGAA | | |
| X-linked Retinoschisis | RS1 | | |
| Choroideremia | hCHM | | |

TABLE 3A-continued

| Disease | Transgene | UniProtKb No. (or ID No.) | Exemplary GenBank or NCBI RefSeq No. (cDNA size/kb) |
|---|---|---|---|
| Giant Axonal Neuropathy | JeT-GAN | | |
| Duchenne Muscular Dystrophy | rmicro-Dystrophin | | |
| X-linked Retinoschisis | hRS1 | | |
| Squamous Cell Head and Neck Cancer; Radiation Induced Xerostomia | hAQP1 | | |
| Hemophilia B | Factor IX | | |
| Homozygous FH | hLDLR | | |
| Dysferlinopathies | rAAVrh74.MHCK7.DYSF.DV | | |
| Hemophilia B | AAV6 ZFP nuclease | | |
| MPS I | AAV6 ZFP nuclease | | |
| Rheumatoid Arthritis | NF-KB.IFN-β | | |
| Batten/CLN6 | CLN6 | | |
| Sanfilippo Disease Type A | hSGSH | | |
| Osteoarthritis | 5IL-1Ra | | |
| Achromatopsia | CNGA3 | | |
| Achromatopsia | CNGB3 | | |
| Ornithine Transcarbamylase (OTC) Deficiency | OTC | | |
| Hemophilia A | Factor VIII | | |
| Mucopolysaccharidosis II | ZFP nuclease | | |
| Hemophilia A | ZFP nuclease | | |
| Wet AMD | anti-VEGF | | |
| X-Linked Retinitis Pigmentosa | RPGR | | |
| Mucopolysaccharidosis Type VI | hARSB | | |
| Leber Hereditary Optic Neuropathy | ND4 | | |
| X-Linked Myotubular Myopathy | MTM1 | | |
| Crigler-Najjar Syndrome | UGT1A1 | | |
| Achromatopsia | CNGB3 | | |
| Retinitis Pigmentosa | hPDE6B | | |
| X-Linked Retinitis Pigmentosa | RPGR | | |
| Mucopolysaccharidosis Type 3 B | hNAGLU | | |
| Inhibitory functions of antisense RNA | Pri-miR-30a scaffold (containing guide and passenger RNA) | | |
| Inhibitory functions of antisense RNA | Pri-miR-124-3 scaffold (containing guide and passenger RNA) | | |
| Inhibitory functions of antisense RNA | Pri-miR-155 scaffold (containing guide and passenger RNA) | | |
| Inhibitory functions of antisense RNA | Pri-miR-218-1 scaffold (containing guide and passenger RNA) | | |

TABLE 3B

| | ANTIGENS | | ANTIBODIES | INDICATIONS |
|---|---|---|---|---|
| 1. | Nervous System Targets | Amyloid beta (Aβ or Abeta) peptides derived from APP | Solanezumab GSK933776 | Alzheimer's Disease |
| | | Sortilin | AL-001 | Frontotemporal dementia (FTD) |
| | | Tau protein | ABBV-8E12 UCB-0107 NI-105 (BIIB076) | Alzheimer's, Progressive supranuclear palsy, frontotemporal demential, chronic traumatic encephalopathy, Pick's complex, primary age-related taupathy |
| | | Semaphorin-4D (SEMA4D) | VX15/2503 | Huntington's disease, juvenile Huntington's disease |
| | | alpha-synuclein | Prasinezumab NI-202 (BIIB054) MED-1341 | Parkinson's disease, synucleinopathies |
| | | superoxide dismutase-1 (SOD-1) | NI-204 | ALS, Alzheimer's Disease |

TABLE 3B-continued

| | ANTIGENS | | ANTIBODIES | INDICATIONS |
|---|---|---|---|---|
| | | CGRP Receptor | eptinezumab, fremanezumab galcanezumab | Migraines, Cluster headaches |
| 2. | Ocular Anti-Angiogenic Targets | VEGF | Sevacizumab | diabetic retinopathy (DR), myopic choroidal neovascularization (mCNV), age-related macular degeneration (AMD), macular edema |
| | | erythropoietin receptor | LKA-651 | retinal vein occlusion (RVO), wet AMD, macular edema |
| | | Amyloid beta (Aβ or Abeta) peptides derived from APP | Solanezumab GSK933776 | Dry AMD |
| | | activin receptor like kinase 1 (ALK1) | ascrinvacumab | neovascular age-related macular degeneration |
| | | complement component 5 (C5) | tesidolumab | dry AMD, uveitis |
| | | endoglin (END or CD105) | carotuximab | wet AMD and other retinal disorders caused by increased vascularization |
| | | complement component 1Q (C1Q) | ANX-007 | glaucoma |
| 3. | TNF-alpha | | adalimumab (HUMIRA ®) infliximab (REMICADE ®) golimumab | uveitis |
| 4. | Repulsive guidance molecule-A | | elezanumab | multiple sclerosis |
| 5. | Transthyretin (TTR) | | NI-301 PRX-004 | amyloidosis |
| 6. | Connective tissue growth factor (CTGF) | | pamrevlumab | fibrotic diseases, e.g. diabetic nephropathy, liver fibrosis, idiopathic pulmonary fibrosis |
| 7. | Neuromyelitis optica (NMO)/Uveitis targets | interleukin receptor 6 (IL6R) | Satralizumab sarilumab | NMO, DR, DME, uveitis |
| | | CD19 | inebilizumab | NMO |
| 8. | Integrin beta 7 | | etrolizumab | ulcerative colitis, Crohn's disease |
| 9. | Sclerostin | | romosozumab (EVENITY ®) | Osteoporosis, abnormal bone loss or weakness |

TABLE 3C

| | ANTIGENS | | ANTIBODIES | INDICATIONS |
|---|---|---|---|---|
| 1. | Nervous System Targets | Amyloid beta (Aβ or Abeta) peptides | Aducanumab crenezumab gantenerumab | Alzheimer's Disease |
| | | Tau protein | anti-TAU | Alzheimer's, Progressive supranuclear palsy, frontotemporal demential, chronic traumatic encephalopathy, Pick's complex, primary age-related taupathy |
| | | CGRP Receptor | erenumab (AIMOVIG ™) | Migraine |

TABLE 3C-continued

| ANTIGENS | | ANTIBODIES | INDICATIONS |
|---|---|---|---|
| 2. Interleukins or interleukin receptors | IL-17A | ixekizumab (TALTZ ® secukinumab (COSENTYX ®) | Plaque psoriasis, psoriatic arthritis, ankylosing sponylitis |
| | IL-5 | mepolizumab (NUCALA ®) | Asthma |
| | IL-12/IL-23 | ustekinumab (STELARA ®) | Psoriasis & Crohn's disease |
| | IL-4R | dupilumab | Atopic dermatitis |
| 3. | Integrin | vedolizumab (ENTYVIO ®) | Ulcerative colitis & Crohn's disease |
| | | Natalizumab (anti-integrin alpha 4) | Multiple sclerosis & Crohn's disease |
| 4. Cardiovascular Targets | PCSK9 | alirocumab (PRALUENT ®) evolucomab (REPATHA ®) | HeFH & HoFH |
| | ANGPTL3 | evinacumab | HoFH & severe forms of dyslipidema |
| | Proinflammatory/ proatherogenic phospholipids | E06-scFv | Cardiovascular diseases such as atherosclerosis |
| 5. | RANKL | denosumab (XGEVA ® and PROLIA ®) | Osteoporosis, increasing bone mass in breast and prostate cancer patients, & preventing skeletal-related events due to bone metastasis |
| 6. | PD-1, or PD-L1 or PD-L2 | nivolumab (OPDIVO ®) pembrolizumab (KEYTRUDA ®) | Metastatic melanoma, lymphoma, non-small cell lung carcinoma |
| 7. | BLyS (B-lymphocyte stimulator, also known as B-cell activating factor (BAFF)) | belimumab (BENLYSTA ®) | Systemic lupus erythromatosis |
| 8. Ocular Targets | VEGF | ranibizumab (LUCENTIS ®) bevacizumab (AVASTIN ®) brolucizumab | Wet AMD |
| | Factor D | lampalizumab | Dry AMD |
| | MMP9 | andecaliximab | |
| 9. | TNF-alpha | adalimumab (HUMIRA ®) and infliximab (REMICADE ®) | Rheumatoid arthritis, psoriatic arthritis, askylosing spondylitis, Crohn's disease, plaque psoriasis, ulcerative colitis |
| 10. Plasma Protein targets | C5, C5a | eculizumab (SOLIRIS ®) | Paroxysmal nocturnal hemoglobinuria, atypical hemolytic uremic syndrome, complement-mediated thrombotic microangiopathy |
| | Plasma kallikrein | lanadelumab | Hereditary angioedema (HAE) |

Generally, the rAAV vector is administered systemically, and following transduction, the vector's production of the protein product is enhanced by an expression cassette employing engineered liver-specific nucleic acid regulatory elements. For example, the rAAV vector may be provided by intravenous, intramuscular, subcutaneous and/or intra-peritoneal administration. In other examples, the rAAV vector may be administered intrathecal, cisterna magna, intranasal, or intravitreal, subretinally, or suprachoroidally.

In some aspects, the rAAVs of the present invention find use in delivery to target tissues associated with the disorder or disease to be treated/prevented. A disease or disorder associated with a particular tissue or cell type is one that largely affects the particular tissue or cell type, in comparison to other tissue of cell types of the body, or one where the effects or symptoms of the disorder appear in the particular tissue or cell type. Methods of delivering a transgene to a target tissue of a subject in need thereof involve administering to the subject an rAAV where the expression cassette comprises a stuffer polynucleotide sequence, such as in Table 1, or a fragment or fragments thereof.

Following transduction of target cells, the expression of the protein product is enhanced by employing such liver-specific expression cassettes. Such enhancement may be measured by the following non-limiting list of determinations such as 1) protein titer by assays known to the skilled person, not limited to sandwich ELISA, Western Blot, histological staining, and liquid chromatography tandem mass spectrometry (LC-MS/MS); 2) protein activity, by assays such as binding assays, functional assays, enzymatic assays and/or substrate detection assays; and/or 3) serum half-life or long-term expression. Enhancement of transgene expression may be determined as efficacious and suitable for human treatment (Hintze, J. P. et al, Biomarker Insights 2011:6 69-78). Assessment of the quantitative and functional properties of a transgene using such in vitro and in vivo cellular, blood and tissue studies have been shown to correlate to the efficacy of certain therapies (Hintze, J. P. et al, 2011, supra), and are utilized to evaluate response to gene therapy treatment of the transgene with the vectors described herein.

rAAV vectors of the invention also can facilitate delivery, in particular, targeted delivery, of transgenes operably linked to the chimeric regulatory sequences described herein, including but not limited to oligonucleotides, drugs, imaging agents, inorganic nanoparticles, liposomes, antibodies to target cells or tissues. The rAAV vectors also can facilitate delivery, in particular, targeted delivery, of non-coding DNA, RNA, or oligonucleotides to target tissues.

The agents may be provided as pharmaceutically acceptable compositions as known in the art and/or as described herein. In some embodiments, the rAAV molecule may be administered alone or in combination with other prophylactic and/or therapeutic agents.

The dosage amounts and frequencies of administration provided herein are encompassed by the terms therapeutically effective and prophylactically effective. The dosage and frequency will typically vary according to factors specific for each patient depending on the specific therapeutic or prophylactic agents administered, the severity and type of disease, the route of administration, as well as age, body weight, response, and the past medical history of the patient, and should be decided according to the judgment of the practitioner and each patient's circumstances. Suitable regimens can be selected by one skilled in the art by considering such factors and by following, for example, dosages reported in the literature and recommended in the Physician's Desk Reference ($56^{th}$ ed., 2002). Prophylactic and/or therapeutic agents can be administered repeatedly. Several aspects of the procedure may vary such as the temporal regimen of administering the prophylactic or therapeutic agents, and whether such agents are administered separately or as an admixture.

The amount of an agent of the invention that will be effective can be determined by standard clinical techniques. Effective doses may be extrapolated from dose-response curves derived from in vitro or animal model test systems. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

Prophylactic and/or therapeutic agents, as well as combinations thereof, can be tested in suitable animal model systems prior to use in humans. Such animal model systems include, but are not limited to, rats, mice, chicken, cows, monkeys, pigs, dogs, rabbits, etc. Any animal system well-known in the art may be used. Such model systems are widely used and well known to the skilled artisan. In some preferred embodiments, animal model systems for a CNS condition are used that are based on rats, mice, or other small mammal, other than a primate.

Once the prophylactic and/or therapeutic agents of the invention have been tested in an animal model, they can be tested in clinical trials to establish their efficacy. Establishing clinical trials will be done in accordance with common methodologies known to one skilled in the art, and the optimal dosages and routes of administration as well as toxicity profiles of agents of the invention can be established. For example, a clinical trial can be designed to test a rAAV molecule of the invention for efficacy and toxicity in human patients.

Toxicity and efficacy of the prophylactic and/or therapeutic agents of the instant invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

A rAAV molecule of the invention generally will be administered for a time and in an amount effective for obtain a desired therapeutic and/or prophylactic benefit. The data obtained from the cell culture assays and animal studies can be used in formulating a range and/or schedule for dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized.

A therapeutically effective dosage of an rAAV vector for patients is generally from about 0.1 ml to about 100 ml of solution containing concentrations of from about $1\times10^{9}$ to about $1\times10^{16}$ genomes rAAV vector, or about $1\times10^{10}$ to about $1\times10^{15}$, about $1\times10^{12}$ to about $1\times10^{16}$, or about $1\times10^{14}$ to about $1\times10^{16}$ AAV genomes. Levels of expression of the transgene can be monitored to determine/adjust dosage amounts, frequency, scheduling, and the like.

Treatment of a subject with a therapeutically or prophylactically effective amount of the agents of the invention can include a single treatment or can include a series of treatments. For example, pharmaceutical compositions comprising an agent of the invention may be administered once a day, twice a day, or three times a day. In some embodiments, the agent may be administered once a day, every other day, once a week, twice a week, once every two weeks, once a month, once every six weeks, once every two months, twice a year, or once per year. It will also be appreciated that the effective dosage of certain agents, e.g., the effective dosage of agents comprising a dual antigen-binding molecule of the invention, may increase or decrease over the course of treatment.

Methods of administering agents of the invention include, but are not limited to, parenteral administration (e.g., intradermal, intramuscular, intraperitoneal, intravenous, and subcutaneous, including infusion or bolus injection), epidural, and by absorption through epithelial or mucocutaneous or mucosal linings (e.g., intranasal, oral mucosa, rectal, and intestinal mucosa, etc.). In certain embodiments, the transgene is administered intravenously even if intended to be expressed in the CNS. In other embodiments, the transgene is administered intrathecally, intracranially.

In certain embodiments, the agents of the invention are administered intravenously and may be administered together with other biologically active agents.

In addition, the rAAVs can be used for in vivo delivery of transgenes for various genetic modification systems such as gene knock-down with miRNAs, recombinase delivery for conditional gene deletion, gene editing with CRISPRs, and the like.

Pharmaceutical Compositions and Kits

The invention further provides a pharmaceutical composition comprising a pharmaceutically acceptable carrier and an agent of the invention, said agent comprising a rAAV molecule of the invention comprising a transgene cassette wherein the transgene expression is driven by the chimeric regulatory elements described herein. In preferred embodiments, the pharmaceutical composition comprises rAAV combined with a pharmaceutically acceptable carrier for administration to a subject. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's complete and incomplete adjuvant), excipient, or vehicle with which the agent is administered. Such pharmaceutical carriers can be sterile liquids, such as water and oils, including those of petroleum, animal, vegetable, or synthetic origin, including, e.g., peanut oil, soybean oil, mineral oil, sesame oil and the like. Water is a common carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Additional examples of pharmaceutically acceptable carriers, excipients, and stabilizers include, but are not limited to, buffers such as phosphate, citrate, and other organic acids; antioxidants including ascorbic acid; low molecular weight polypeptides; proteins, such as serum albumin and gelatin; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™ as known in the art. The pharmaceutical composition of the present invention can also include a lubricant, a wetting agent, a sweetener, a flavoring agent, an emulsifier, a suspending agent, and a preservative, in addition to the above ingredients. These compositions can take the form of solutions, suspensions, emulsion, tablets, pills, capsules, powders, sustained-release formulations and the like.

In certain embodiments of the invention, pharmaceutical compositions are provided for use in accordance with the methods of the invention, said pharmaceutical compositions comprising a therapeutically and/or prophylactically effective amount of an agent of the invention along with a pharmaceutically acceptable carrier.

In other embodiments, the agent of the invention is substantially purified (i.e., substantially free from substances that limit its effect or produce undesired side-effects). In a specific embodiment, the host or subject is an animal, preferably a mammal such as non-primate (e.g., cows, pigs, horses, cats, dogs, rats etc.) and a primate (e.g., monkey such as, a cynomolgous monkey and a human). In a preferred embodiment, the host is a human.

The invention provides further kits that can be used in the above methods. In one embodiment, a kit comprises one or more agents of the invention, e.g., in one or more containers. In another embodiment, a kit further comprises one or more other prophylactic or therapeutic agents useful for the treatment of a condition, in one or more containers.

The invention also provides agents of the invention packaged in a hermetically sealed container such as an ampoule or sachette indicating the quantity of the agent or active agent. In one embodiment, the agent is supplied as a dry sterilized lyophilized powder or water free concentrate in a hermetically sealed container and can be reconstituted, e.g., with water or saline, to the appropriate concentration for administration to a subject. Typically, the agent is supplied as a dry sterile lyophilized powder in a hermetically sealed container at a unit dosage of at least 5 mg, more often at least 10 mg, at least 15 mg, at least 25 mg, at least 35 mg, at least 45 mg, at least 50 mg, or at least 75 mg. The lyophilized agent should be stored at between 2 and 8° C. in its original container and the agent should be administered within 12 hours, usually within 6 hours, within 5 hours, within 3 hours, or within 1 hour after being reconstituted. In an alternative embodiment, an agent of the invention is supplied in liquid form in a hermetically sealed container indicating the quantity and concentration of agent or active agent. Typically, the liquid form of the agent is supplied in a hermetically sealed container at least 1 mg/ml, at least 2.5 mg/ml, at least 5 mg/ml, at least 8 mg/ml, at least 10 mg/ml, at least 15 mg/kg, or at least 25 mg/ml.

The compositions of the invention include bulk drug compositions useful in the manufacture of pharmaceutical compositions (e.g., impure or non-sterile compositions) as well as pharmaceutical compositions (i.e., compositions that are suitable for administration to a subject or patient). Bulk drug compositions can be used in the preparation of unit dosage forms, e.g., comprising a prophylactically or therapeutically effective amount of an agent disclosed herein or a combination of those agents and a pharmaceutically acceptable carrier.

The invention further provides a pharmaceutical pack or kit comprising one or more containers filled with one or more of the agents of the invention. Additionally, one or more other prophylactic or therapeutic agents useful for the treatment of the target disease or disorder can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use, or sale for human administration.

Generally, the ingredients of compositions of the invention are supplied either separately or mixed together in unit dosage form, for example, as a dry lyophilized powder or water-free concentrate in a hermetically sealed container such as an ampoule or sachette indicating the quantity of agent or active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

EXAMPLES

Example 1—Construction of Expression Cassettes with Stuffers

FIG. 1 depicts various arrangements of tandem nucleic acid elements for use with transgenes that include stuffer sequences. Several transgene cassettes were rationally designed to express a gene of interest and evaluate properties of cis plasmids or AAV vectors carrying the transgene.

Example 2—Analysis of Non-Coding Vector in Cynomolgous Monkeys

This study included an animal group dosed with an AAV9 "null" vector (AAV9.null) that was designed to mimic an AAV9 capsid that contains a genome that does not produce mRNA or protein. As such, the vector transgene includes SEQ ID NO:1 (1.6 kb of non-coding "stuffer" cDNA). The AAV9.null vector transgene contains 5' ITR. RBG polyA, CpG-depleted chicken β-actin intron, Stuffer (SEQ ID NO:1 cDNA), and 3' ITR. The upstream RBG polyA allows accurate ddPCR titer comparison with other AAV9 vectors and eliminates any potential transcription from ITR. This animal group was observed for impact of cells transduced with a vector containing non-coding DNA, as well as the effect of capsid on AAV-mediated changes within the brain tissue, particularly the dorsal root ganglia (DRG).

Groups of cynomolgus monkeys (2/sex/group) were administered a single dose of 1) AAV9.null vector (containing the stuffer sequence of SEQ ID NO: 1, and no coding sequence), 2) AAV9.CNS vector (delivers a transgene encoding a CNS protein) or 3) vehicle via cisterna magna puncture (1 mL/animal) to investigate the toxicity of the test articles over 4 weeks. During this study, multiple endpoints were observed. There were no test article-related clinical observations, such as effects on body weight or food intake in animals receiving either vector.

Biodistribution within spinal cord, DRG, sciatic nerve and peripheral tissues (lymph nodes, kidney, heart, ovary, retina/choroid, sclera and testes): At necropsy, samples of tissue were collected and vector DNA measured by qPCR. The resulting copy numbers per μg DNA for each tissue were calculated based on standard calibration curve included in each plate with control plasmid DNA. The results are normalized to one microgram of DNA, with results less than 50 copies/μg DNA (the LLOQ) reported as below the limit of quantitation (BLQ). The upper limit of quantification was 5×108 vector copies/μg DNA.

For animals that were administered AAV9.null vector, vector DNA was detected in all regions of the brain and spinal cord at similar levels or greater to that seen with AAV9.CNS vector-treated animals. Vector DNA was also confirmed in the DRG (cervical, thoracic and lumbar) for AAV9.null-treated cynomolgus monkeys at equivalent or greater levels than seen in AAV9.CNS vector-treated animals. No neuronal degeneration (minimal in the hippocampus and/or midbrain) and/or necrosis (minimal in the cerebellum) was observed in the brains of AAV9.null vector-treated animals.

This study observed that cells transduced with a vector containing non-coding DNA produced no significant treatment-related findings or toxicity, including no DRG-related toxicity in AAV9.null-treated animals.

Example 3—Analysis of Vector Genome Multiplicity of Packaging

Microcapillary-based gel electrophoresis experiments were done for AAV genomes isolated from AAV vector preps made with the cis plasmids of Table 4. Genomes were extracted by Dnase/proteinase K treatment of capsids (~4e11 GCs), phenol/chloroform extracted to isolate genomes, the ethanol precipitated. DNA was resuspended in TE buffer and evaluated on the Agilent 2200 TapeStation system, which is an automated platform for DNA sizing and quantification. Analysis of the DNA molecules was performed according to the manufacturer's recommended protocols for High Sensitivity (HS) D5000 ScreenTape (Agilent #5067-5592) using D5000 Reagents (Agilent #5067-5593). TapeStation measures dsDNA (rather than ssDNA) and TapeStation evaluation relies on the annealing of two complementary ssAAV genomes to form an equivalent approximation of a dsAAV genome length in base pairs. In cases where annealing takes place but with imperfect alignments (such as can occur for longer sequences), base pair lengths indicated in the readouts may not be absolute, but still provide an approximation of whether recombination of multiple genomes does occur (e.g. 1×, 2×, 3× in FIG. 2A).

TABLE 4

| Plasmid (for vector production) | Construction (5' ITR to 3' ITR) | Genome size (kb) |
|---|---|---|
| P1 | ITR-promoter-miR1-polyA-minimal Stuffer(30 bp of SEQ ID NO: 5) -ITR | 1.5 |
| P2 | ITR-promoter-miR2-polyA-minimal Stuffer(30 bp of SEQ ID NO: 5) -ITR | 1.5 |
| P3 | ITR-promoter-miR1-polyA-Stuffer(SEQ ID NO: 1) + minimal stuffer(30 bp of SEQ ID NO: 5) -ITR | 3.1 |
| P4 | ITR-promoter-miR2-polyA-Stuffer(SEQ ID NO: 1) + minimal stuffer(30 bp of SEQ ID NO: 5) -ITR | 3.1 |
| P5 | ITR-promoter-miR1-miR2-polyA- Stuffer(SEQ ID NO: 1)-ITR | 3.45 |

Figure 2A:
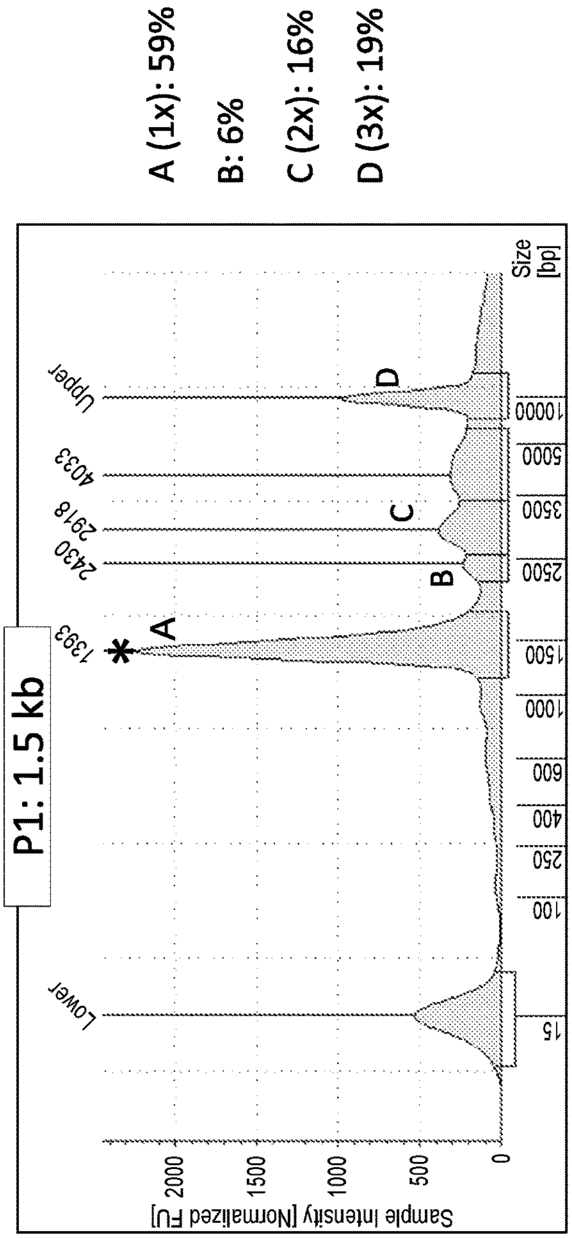
FIGS. 2A-2E depict P1-P5 vector genome sizes as evaluated by electrophoresis using the TapeStation method. 2A depicts single and multiple packaging from a 1.5 kb genome analysis of P1 vectors; 2B depicts single and multiple packaging from a 1.5 kb genome analysis of P2 vectors; 2C depicts primarily single packaging from a 3.1 kb genome analysis of vector P3; 2D depicts primarily single packaging from a 3.1 kb genome analysis of vector P4; 2E depicts primarily single packaging from a 3.1 kb genome analysis of vector P5.
Figure 2B:
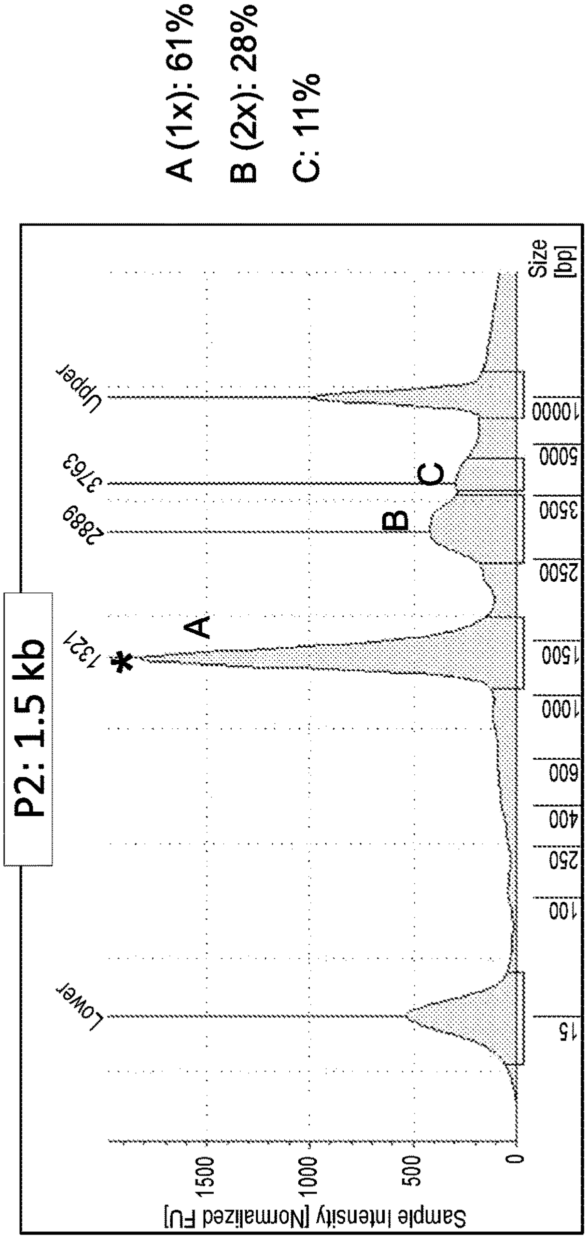
Figure 2C:
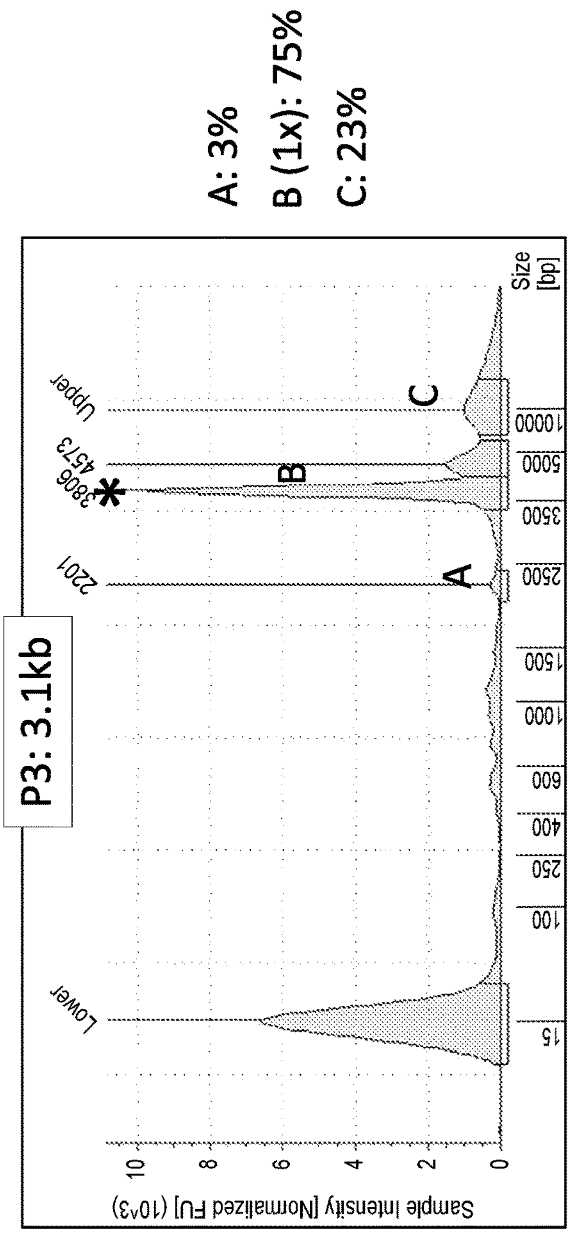
Figure 2D:
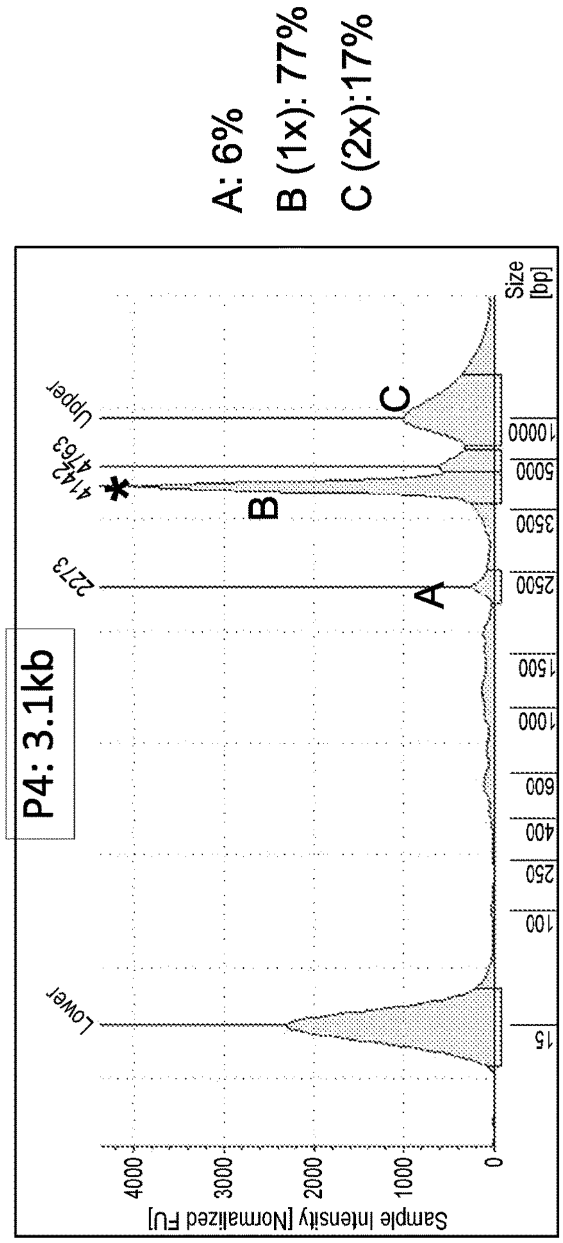
Figure 2E:
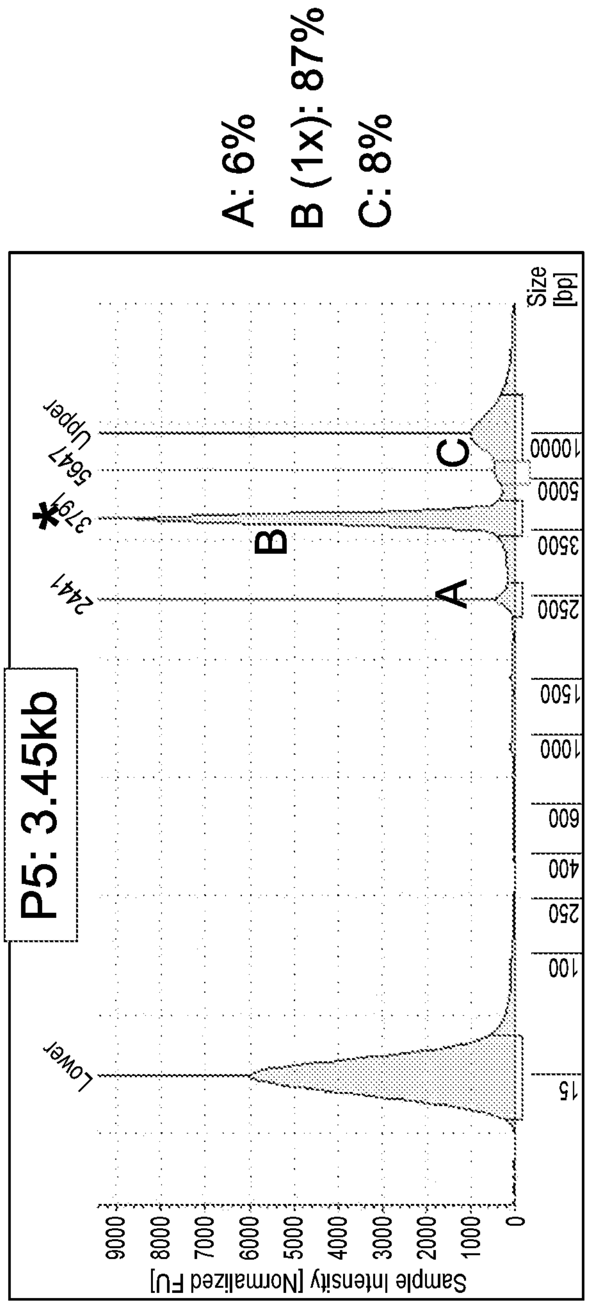

Vectors packaged with transgenes from cis plasmids P1 and P2, each having a genome length of 1.5 kb, were subject to more multiples of genomes as detected by electrophoresis. For example, FIG. 2A shows multiples of 2× genome accounted for 16% and 3× genome accounted for 19% of the total DNA. As noted, imperfect annealing due to the technique does occur (when creating dsDNA) and is likely causing the observed additional DNA species that do not run true to size on the gel, and this imperfect annealing is unlikely to have implications for specifically related to packaging. Notably, the genomes of P1 and P2 (FIGS. 2A-2B) are similar to P3 and P4 which contain additional stuffer sequence (FIGS. 2C-2D) whereas multiple genomes are reduced in P3 and P4. P5 (FIG. 2E) depicts a further reduction in multiply packaged genomes for an AAV genome ~3.45 kb in length, with single packaged genomes reaching 87% of total DNA extracted.

EQUIVALENTS

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims. Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference in their entireties.

The discussion herein provides a better understanding of the nature of the problems confronting the art and should not be construed in any way as an admission as to prior art nor should the citation of any reference herein be construed as an admission that such reference constitutes "prior art" to the instant application.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

We claim:

1. A recombinant expression cassette comprising a polynucleotide stuffer sequence of (i) SEQ ID NO: 1 or a fragment of SEQ ID NO: 1 between 1,000 and 1,601 nucleotides in length, (ii) SEQ ID NO:2, (iii) SEQ ID NO:3, (iv) SEQ ID NO:4, or (v) SEQ ID NO:5 or a fragment of SEQ ID NO: 5 between 1,000 and 2,001 nucleotides in length.

2. The recombinant expression cassette of claim 1 further comprising a heterologous gene encoding a microRNA, a short hairpin RNA, an antibody, an antibody-binding antibody fragment, a Fc-fusion protein, or an enzyme.

3. A recombinant adeno-associated viral vector comprising the recombinant expression cassette of claim 1, wherein the stuffer sequence comprises SEQ ID NO:1 or a fragment of SEQ ID NO: 1 between 1,000 and 1,601 nucleotides in length.

4. A recombinant adeno-associated viral vector comprising the recombinant expression cassette of claim 1, wherein the stuffer sequence comprises SEQ ID NO:2.

5. A recombinant adeno-associated viral vector comprising the recombinant expression cassette of claim 1, wherein the stuffer sequence comprises SEQ ID NO:3.

6. A recombinant adeno-associated viral vector comprising the recombinant expression cassette of claim 1, wherein the stuffer sequence comprises SEQ ID NO:4.

7. A recombinant adeno-associated viral vector comprising the recombinant expression cassette of claim 1, wherein the stuffer sequence comprises SEQ ID NO:5 or a fragment of SEQ ID NO: 5 between 1,000 and 2,001 nucleotides in length.

* * * * *